(12) United States Patent
Moreau et al.

(10) Patent No.: US 11,860,169 B2
(45) Date of Patent: Jan. 2, 2024

(54) METHOD OF TREATING AND PROGNOSING SCOLIOTIC PATIENT SUBGROUPS

(71) Applicant: Chu Sainte-Justine, Montreal (CA)

(72) Inventors: Alain Moreau, Montreal (CA); Marie-Yvonne Akoume Ndong, Montreal (CA)

(73) Assignee: CHU SAINTE-JUSTINE, Montreal (CA)

( * ) Notice: Subject to any disclaimer, the term of this patent is extended or adjusted under 35 U.S.C. 154(b) by 156 days.

(21) Appl. No.: 17/015,006

(22) Filed: Sep. 8, 2020

(65) Prior Publication Data

US 2021/0109112 A1    Apr. 15, 2021

Related U.S. Application Data

(60) Continuation of application No. 15/910,586, filed on Mar. 2, 2018, now abandoned, which is a division of application No. 14/917,786, filed as application No. PCT/CA2014/050852 on Sep. 9, 2014, now abandoned.

(60) Provisional application No. 61/879,314, filed on Sep. 18, 2013, provisional application No. 61/875,162, filed on Sep. 9, 2013.

(51) Int. Cl.
| | |
|---|---|
| *G01N 33/68* | (2006.01) |
| *G01N 33/487* | (2006.01) |
| *G01N 33/53* | (2006.01) |
| *A61F 5/02* | (2006.01) |
| *A61K 31/4045* | (2006.01) |
| *A61K 33/04* | (2006.01) |
| *A61K 45/06* | (2006.01) |
| *A61K 31/713* | (2006.01) |
| *A61K 38/19* | (2006.01) |
| *C12N 15/113* | (2010.01) |
| *A61K 38/08* | (2019.01) |

(52) U.S. Cl.
CPC .......... *G01N 33/6893* (2013.01); *A61F 5/02* (2013.01); *A61F 5/026* (2013.01); *A61K 31/4045* (2013.01); *A61K 31/713* (2013.01); *A61K 33/04* (2013.01); *A61K 38/19* (2013.01); *A61K 45/06* (2013.01); *C12N 15/1138* (2013.01); *G01N 33/48728* (2013.01); *A61K 38/08* (2013.01); *C12N 2310/14* (2013.01); *C12N 2320/30* (2013.01); *G01N 33/53* (2013.01); *G01N 2333/04* (2013.01); *G01N 2333/726* (2013.01); *G01N 2800/10* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,015,837 A | 1/2000 | Etlinger et al. | |
| 6,025,155 A | 2/2000 | Hadlaczky et al. | |
| 6,077,677 A | 6/2000 | Hodgson et al. | |
| 6,204,023 B1 | 3/2001 | Robinson et al. | |
| 7,967,767 B2 | 6/2011 | Ogilvie | |
| 7,989,175 B2 | 8/2011 | Moreau | |
| 9,029,094 B2 | 5/2015 | Moreau et al. | |
| 2001/0036921 A1* | 11/2001 | Ashkar | A61L 27/38 530/329 |
| 2002/0160970 A1 | 10/2002 | Hadlaczky et al. | |
| 2003/0083293 A1 | 5/2003 | Hadlaczky et al. | |
| 2009/0137934 A1 | 5/2009 | Seon | |
| 2009/0275871 A1 | 11/2009 | Liu | |
| 2010/0075333 A1 | 3/2010 | Moreau | |
| 2011/0195436 A1* | 8/2011 | Moreau | G01N 33/5008 435/7.24 |
| 2012/0088809 A1 | 4/2012 | Falco et al. | |

FOREIGN PATENT DOCUMENTS

| | | |
|---|---|---|
| WO | 2003073102 A1 | 9/2003 |
| WO | 2004040236 A2 | 5/2004 |
| WO | 2006068459 A1 | 6/2006 |
| WO | 2008119170 A1 | 10/2008 |
| WO | WO 2008/119170 A1 * | 10/2008 |
| WO | 2009155159 A2 | 12/2009 |
| WO | 2010040234 A1 | 4/2010 |
| WO | 2010044796 A1 | 4/2010 |
| WO | 2010048670 A1 | 5/2010 |
| WO | WO 2010/048670 A1 * | 5/2010 |
| WO | 2012045176 A1 | 4/2012 |

(Continued)

OTHER PUBLICATIONS

Feldman, 2002, Molecular Pharmacology. 61(4): 707-709.*

(Continued)

*Primary Examiner* — Elizabeth C. Kemmerer

(74) *Attorney, Agent, or Firm* — Lavery, de Billy, L.L.P.; Julie Gauvreau

(57) ABSTRACT

The present invention provides a method of treating a subject in need thereof comprising classifying the subject into functional group FG1, FG2 or FG3, wherein i) when the subject is classified into the FG1 functional group, (A) the level of OPN or the activity of OPN in said subject is increased; (B) the subject is not treated with a brace; or (C) a combination of (A) and (B); and ii) when the subject is classified into the FG2 or FG3 functional group, (A) the level of OPN or the activity of OPN in said subject is decreased; (B) the subject is treated with a brace; or (C) a combination of (A) and (B).

7 Claims, 26 Drawing Sheets

Specification includes a Sequence Listing.

(56) References Cited

FOREIGN PATENT DOCUMENTS

| WO | 2014201557 A1 | 12/2014 |
| WO | 2014201560 A1 | 12/2014 |
| WO | 2014201561 A1 | 12/2014 |
| WO | 2015032004 A1 | 3/2015 |
| WO | 2015032005 A1 | 3/2015 |

OTHER PUBLICATIONS

Janigro (2008, Epilepsy Currents 8(1): 23-24).*
Breit et al. (2012, Nephrol. Dial. Transplant. 27:70-75).*
Ho et al. (2013, Clin. Chem. 59:1613-1620).*
Abulizi et al. (2017, Sci. Rep. 7(1):1037; pp. 1-10).*
Zimmers et al. (2005, Shock 23(6):543-548).*
Mazagova et al. (2013, Am. J. Physiol. Renal Physiol. 305:F1249-F1264).*
Kempf et al. (2006, Cir. Res. 98:351-350).*
Wong et al., "Idiopathic scoliosis in Singapore schoolchildren: a prevalence study 15 years into the screening program", Spine (Phila Pa 1976). vol. 30, No. 10, pp. 1188-1196 (2005).
Wong Guoruey, "Étude de la mécanotransduction dans la scoliose idiopathique de l'adolescence (SIA)", Département de Sciences Biomédicales Faculté de Médecine, Dec. 2011, 172 pages.
Xu et al., "Potential genetic markers predicting the outcome of brace treatment in patients with adolescent idiopathic scoliosis" Eur Spine J (2011) 20:1757-1764.
European Office Action in EP14842237.1 dated Dec. 21, 2017.
Final Office Action in U.S. Appl. No. 14/917,757 dated Dec. 6, 2017.
European Office Action in EP14842898.0 dated Feb. 8, 2018.
U.S. Office Action in U.S. Appl. No. 14/917,757 dated Mar. 28, 2018.
Notice of Allowance for U.S. Appl. No. 14/917,757, dated Nov. 15, 2018.
Akoume et al., "A Differential Hypofunctionality of Gαi Proteins Occurs in Adolescent Idiopathic Scoliosis and Correlates with the Risk of Disease Progression" Scientific Reports, (2019) 9:10074 | https://doi.org/10.1038/s41598-019-46325-2.
Akoume et al., "A Differential Hypofunctionality of Gαi Proteins Occurs in Adolescent Idiopathic Scoliosis and Correlates with the Risk of Disease Progression" Scientific Reports, (2019) supplementary Information.
Lonstein et al., "The Milwaukee brace for the treatment of adolescent idiopathic scoliosis. A review of one thousand and twenty patients" J. Bone Joint Surg. Am. (1994) 76(8): 1207-1221. (Abstract).
Feldman "Deactivation of Vasodilator Responses by GRK2 Overexpression: A Mechanism or the Mechanism for Hypertension?" Molecular Pharmacology (2002) 61(4): 707-709.
Janigro "Gene Expression in Temporal Lobe Epilepsy" Epilepsy Currents (2008) 8(1): 23-24.
Breit et al., Nephrol. Dial. Transplant. (2012) 27: 70-75.
Ho et al. "Biomarkers of Cardiovascular Stress and Incident Chronic Kidney Disease" Clin. Chem. (2013) 59(11):1613-1620.
Abulizi et al. "Growth Differentiation Factor-15 Deficiency Augments Inflammatory Response and Exacerbates Septic Heart and Renal Injury Induced by Lipopolysaccharide" Sci. Rep. (2017) 7(1)1037:pp. 1-10.
Zimmers et al. "Growth differentiation factor-15/macrophage inhibitory cytokine-1 induction after kidney and lung injury" Shock (2005) 23(6): 543-548.
Mazagova et al. "Genetic deletion of growth differentiation factor 15 augments renal damage in both type 1 and type 2 models of diabetes" Am. J. Physiol. Renal Physiol. (2013) 305(9): F1249-F1264.
Kempf et al. "The transforming growth factor-beta superfamily member growth-differentiation factor-15 protects the heart from ischemia/reperfusion injury" Cir. Res. (2006) 98(3):351-360.
Akoume et al., "Disrupted Gi-coupled receptor signaling occurs in adolescent idiopathic scoliosis", J. clin. Invest., (2013) (submitted).
Akoume, M.Y. et al., "Cell-based assay protocol for the prognostic prediction of idiopathic scoliosis using cellular dielectric spectroscopy", Journal of Visualized Experiments [URL: http://jove.com/video/50768] (2013) Oct. 2013, vol. 80, e50768, pp. 1-9. No ISSN.
Akoume, M.Y. et al., "Cell-based screening test for idiopathic scoliosis using cellular dialectric spectroscopy", Spine Jun. 2010, vol. 35, No. 13, pp. E601-608, ISSN: 1528-1159.
Akoume, M.Y. et al., "From melatonin to systemic Gi signaling defect: a hopeful odyssey for adolescent idiopathic scoliosis", Scoliosis vol. 5 (suppl. 1), p. 017, May 20-22, 2010, ISSN: 1748-7161, Canada.
Asher et al., "Adolescent idiopathic scoliosis: natural history and long term treatment effects", Scoliosis, 1:2, published: Mar. 31, 2006, pp. 1-10.
Azeddine et al., "Molecular determinants of melatonin signaling dysfunction in adolescent idiopathic scoliosis", Clinical Orthopaedics and Related Research, No. 462, pp. 45-52, Sep. 2007.
Bunnell, W.P., "Selective screening for scoliosis", Clinical Orthopaedics and Related Research, No. 434, pp. 40-45, May 2005.
Campbell, "Monoclonal Antibody Technology: The production and characterization of Rodent and Human Hybridomas", Elsevier Science Publisher, 2000, Amsterdam, The Netherlands.
Chalmers et al., "Predicting the outcome of brace treatment for scoliosis using conditional fuzzy clustering", IEEE, Sep. 2013, pp. 837-842.
Chowanska et al., "School screening for scoliosis: can surface topography replace examination with scoliometer? Scoliosis", 7(9), 1748-7161 (2012).
Donzeau et al., Methods in Molecular Biology: vol. 378, 2007, pp. 15-31.
Enneking et al., "Pathological changes in scoliosis", The Journal of Bone and Joint Surgery, vol. 51, No. 1, Jan. 1969, pp. 165-184.
Fong et al., "A meta-analysis of the clinical effectiveness of school scoliosis screening", Spine, vol. 35, No. 10, pp. 1061-1071, 2010.
Huang et. al., Analyst, 2008, 133(5): 643-648.
International Search Report for Application No. PCT/CA2014/050852 dated Dec. 4, 2014.
International Search Report for Application No. PCT/CA2014/050853 dated Dec. 5, 2014.
Julien et al., "Towards a comprehensive diagnostic assay for scoliosis", Personnalized Medecine, 2013, 10(1), 97-103.
Kane, W.J., "Scoliosis Prevalence: a call for a statement of terms", Clinical Orthopaedics and Related Research, 126, 43-46, Feb. 28, 1977, Chicago, Illinois.
Kim et al., "Scoliosis imaging: what radiologists should know", Radiographics, 30(7), 1823-1842, Nov.-Dec. 2010.
Kohler et al., "Continuous cultures of fused cells secreting antibody of predefined specificity", Nature, 256: 495-497, Aug. 7, 1975.
Letellier et al., "Estrogen cross-talk with the melatonin signaling pathway in human osteoblasts derived from adolescent idiopathic scoliosis patients", Journal of Pineal Research 45(4): 383-393, Accepted: Apr. 29, 2008, Canada.
Letellier, K. et al., "Récent progrès dans l'étiopathogénie de la scoliose idiopathique de l'adolescent et nouveaux concepts moléculaires", Medecine/Science Nov. 2007, vol. 23, pp. 910-916, ISSN: 0767-0974 (English translation of Summary provided).
Medhurst et al., "Pharmacological and immunohistochemical characterization of the APJ receptor and its endogeneous ligand apelin", 2003, Journal of Neurochemistry, 84, pp. 1162-1172.
Miller, N.H., "Cause and natural history of adolescent idiopathic scoliosis", Orthopedic Clinics of North America, vol. 30, No. 3, pp. 343-352, Jul. 1999, Baltimore, Maryland.
Moreau, A. et al., "Melatonin signaling dysfunction in adolescent idiopathic scoliosis", Spine vol. 29, No. 16, pp. 1772-1781, ISSN: 1528-1159, 2004.
Moreau, A. et al., "Pediatric scoliosis predictive blood tests: progress and challenges for clinicians", Scoliosis (2010), vol. 5 (Suppl 1) p. 03, ISSN: 1748-7161.
Nachemson et al., "Effectiveness of treatment with a brace in girls who have adolescent indiopathic scoliosis", The Journal of Bone and Joint Surgery, vol. 77-A, No. 6, Jun. 1995, pp. 815-822.

(56) References Cited

OTHER PUBLICATIONS

Nachemson, Alf, "A long term follow-up study of non-treated scoliosis", Acta Orthopaedica Scandina, 39 (4), 466-476 (1968), DOI: 10.3109/17453676808989664, Gothenburg, Sweden.
Nagao, M. et al., "Sympathetic control of bone mass regulated by osteopontin", P.NA.S., vol. 108, No. 43, pp. 17767-17772, Oct. 25, 2011, ISSN: 1091-6490.
Nash et al., "Risks of exposure to X-rays in patients undergoing long-term treatment for scoliosis", J Bone Joint Surg Am, 61 (3), 371-400, Apr. 1979 (providing Abstract only.).
Niswender et. al., "A novel assay of Gi/o-linked G protein-coupled receptor coupling to potassium channels provides new insights into the pharmacology of the group III metabotropic glutamate receptors", Molecular Pharmacology, 2008, 73(4), pp. 1213-1224.
Peters et. al., "Evaluation of cellular dielectric spectroscoy, a Whole-Cell, Label-Free Technology for Drug Discovery on Gi-Coupled GPCRs", Published online on Feb. 16, 2007, Journal of Biomolecular Screening 12(3): 312-319.
Richards et al., "Standardization of criteria for adolescent idiopathic scoliosis brace studies: SRS Committee on Bracing and Nonoperative Management", Spine (Phila Pa 1976), Sep. 15, 2005; 30(18):2068-2075.
Riobo et. al., "Activation of heterotrimeric G proteins by smoothened", Aug. 15, 2006, Proc Natl Acad Sci USA, 103(33):12607-12612.
Saugstad et. al., "Metabotropic glutamate receptors activate G-Protein-Coupled inwardly rectifying potassium channels in Xenopus Oocytes", Oct. 1, 1996. The Journal of Neuroscience 16(19):5979-5985.
Solly et. al., Assay Drug Dev. Technol., 2004, 2(4): 363-372.
U.S. Appl. No. 61/875,162, filed Sep. 9, 2013.
U.S. Appl. No. 61/879,314, filed Sep. 18, 2013.
Upadhyay et al., "New prognostic factors to predict the final outcome of brace treatment in adolescent idiopathic scoliosis", Spine, 20(5), Mar. 1, 1995 (Mar. 1, 1995), pp. 537-545 (providing Abstract only.).
Verdonk et al., "Cellular dielectric spectroscopy: a label-free comprehensive platform for functional evaluation of endogenous receptors", Assay Drug Development Technologies, vol. 4, No. 5, 609-619 (2006).
Crouch M F et al.: "Gialpha and Gibeta are part of a signalling complex in Balb/c3T3 cells: Phosphorylation of Gibeta in growth factor-activated fibroblasts", Cellular Signalling Elsevier Science Ltd, GB, vol. 5, No. 1, Jan. 1, 1993 (Jan. 1, 1993), pp. 41-52 XP025582056, ISSN: 0898-6568, DOI: 10.1016/0898-6568(93)90006-8 retrieved on Jan. 1, 1993] * abstract *_.
Evans G A et al.: "Functional classification and orthopaedic management of spinal muscular atrophy", Journal of Bone and Joint Surgery, British Volume, Livingstone, London, GB, [Online] vol. 63B, No. 4, Jan. 1, 1981 (Jan. 1, 1981), pp. 516-522, XP008183256, ISSN: 0301-620X * the whole document *in particular: abstract par. Orthotic programme for scoliosis; p. 521-p. 522.
Kon S et al.: "Mapping of functional epitopes of osteopontin by monoclonal antibodies raised against defined internal sequences", Journal of Cellular Biochemistry, Wiley-Liss Inc, US, vol. 84, No. 2, Oct. 15, 2001 Oct. 15, 2001), pp. 420-432, XP002961001, ISSN: 0730-2312, DOI: 10.1002/JCB.10039 * abstract *.
Supplementary European Search Report for Application No. 14842237.1, dated Feb. 24, 2017.
Elbakry, Mohamed, Déterminants moléculairs de la scoliose idiopathique de l'adolescent, Université de Montréal Faculté de médecine, May 2013, pp. 1-255, Retrieved from the internet: URL: https://papyrus.bib.umontreal.ca/kmlui/bitstream/handle/1866/11338/Elbakry_Mohamed_2013_these.pdf?sequence=2[retrieved on Apr. 10, 2017]. (submitted with English translation of Abstract only.).
Schack et al., Considerable variation in the concentration of osteopontin in human milk, bovine milk, and infant formulas, Journal of Diary Science, Nov. 2009, pp. 5378-5385, vol. 92, No. 11. (Submitted with abstract only.).
Supplementary European Search Report for Application No. EP14842898 dated Apr. 24, 2017.

\* cited by examiner

| Functional group | Effect of OPN | Initial Circulating [OPN] | Brace treatment | Other treatment options (See also Figure 1B) |
|---|---|---|---|---|
| FG1 | Protective | high | No | Increase OPN level or activity (e.g., OPN, OPN agonist, Treatment and preventive measures which increase OPN levels ) |
| | | low | Generally, no. | Increase OPN level or activity (e.g., OPN, OPN agonist, Treatment and preventive measures which increase OPN levels) |
| FG2 | Risk factor | high | Yes | Decrease OPN level or activity (e.g., OPN antagonist Treatment and preventive measures which decrease OPN levels) |
| | | low | Yes, | Decrease OPN level or activity (e.g., OPN antagonist, treatment and preventive measures which decrease OPN levels) |
| FG3 | Risk factor | high | Yes | Decrease OPN level or activity (e.g., OPN antagonist, treatment and preventive measures which decrease OPN levels) |
| | | low | Yes | Decrease OPN level or activity (e.g., OPN antagonist, treatment and preventive measures which decrease OPN levels ) |

FIG. 1A

| Treatment or preventive measure | Functional group | | | Comments |
|---|---|---|---|---|
| | FG1 | FG2 | FG3 | |
| Increase sCD44 level | no | yes | yes | Decreases OPN's bioavailability to integrins (e.g., $\alpha_5\beta_1$) |
| Increase HA level (e.g., supplements or HA-rich diet) | yes | avoid | avoid | HA increases OPN's bioavailability |
| Decrease HA level (e.g., HA-poor diet) | avoid | yes | yes | HA increases OPN's bioavailability |
| Massages (e.g., pulsative compressive pressure, LIPUS) | yes | avoid | avoid | Increase OPN level (see US 13/822,982) |
| accupoint heat sensitive moxibustion; heat therapy with pad; electroacupuncture, thermal bath | no | yes | yes | Decrease plasma OPN levels |
| Src inhibitors | -- | yes | yes | Involved in the activation of PIPK1γ |
| FAK inhibitors | -- | yes | yes | Involved in the activation of PIPK1γ |
| RGD peptides | -- | yes | yes | Inhibit the binding of OPN to integrins |
| Decreasing PIPK1γ level or activity (e.g., inhibitors) | -- | yes | yes | Increases bniding of integrins to OPN |
| Increasing the level or activity of PTPμ | -- | yes | yes | Involves in the dephosphorylation (inhibition) of PIPK1γ |
| Early corrective surgery (before reaching 45 degree Cobb angle) | no | yes, | no | Especially if OPN levels are high and/or remain high. FG2 subjects have an increased risk of severe scoliosis. |

FIG. 1B

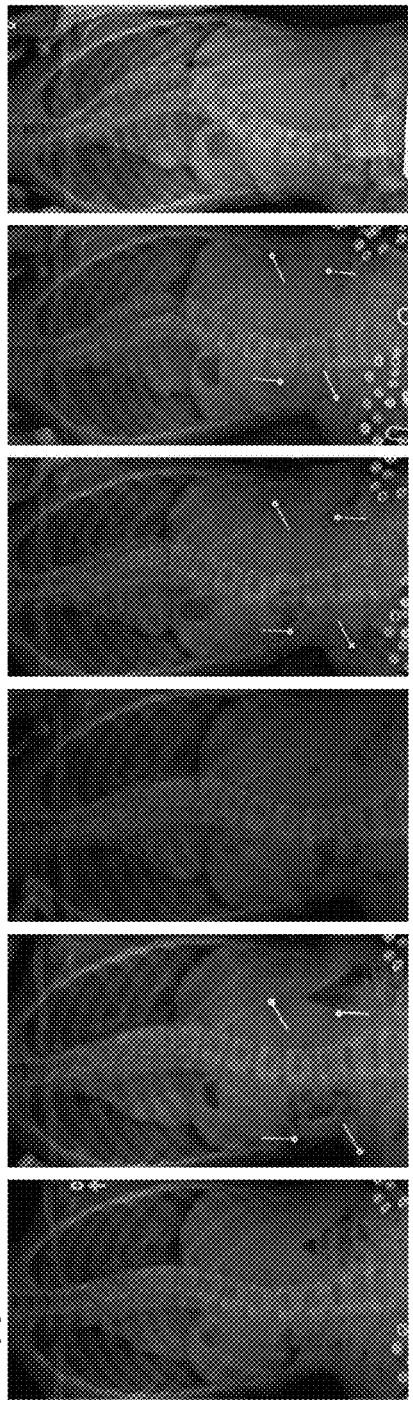
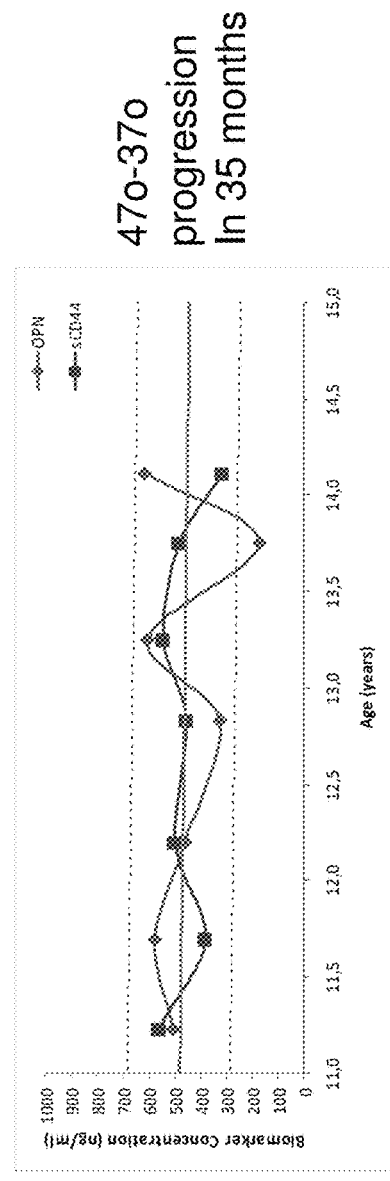
FIG. 4

*Drop in OPN, progression over 5 years*

*Drop in OPN, progression over 34 months*

*Drop in OPN, progression over 42 months*

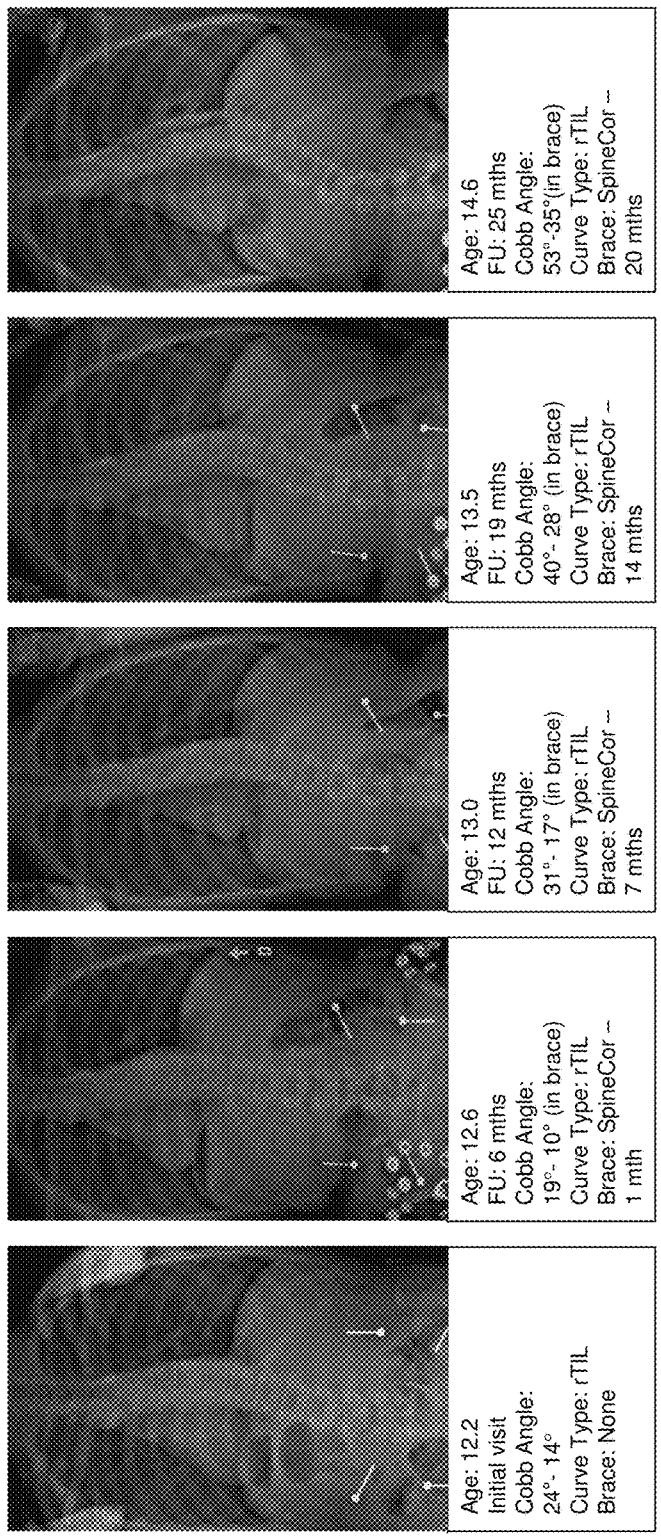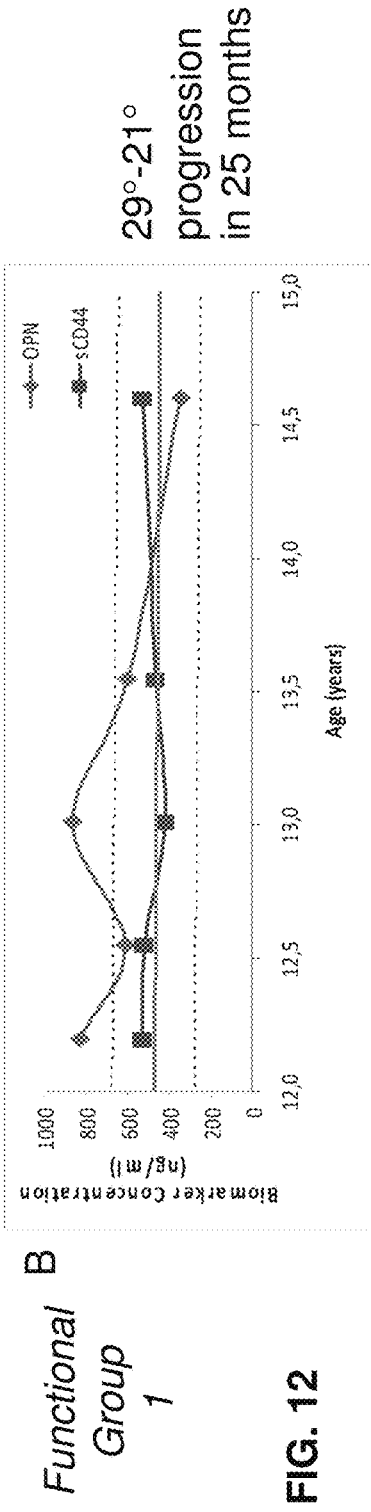
FIG. 12

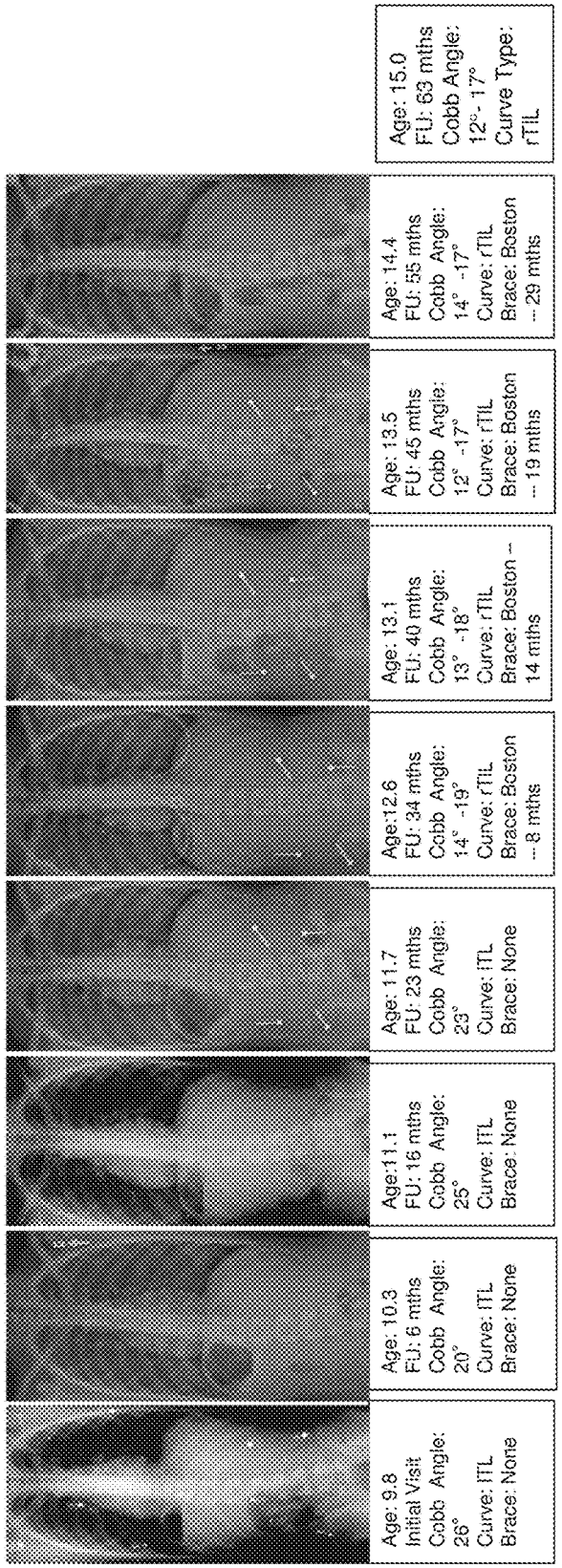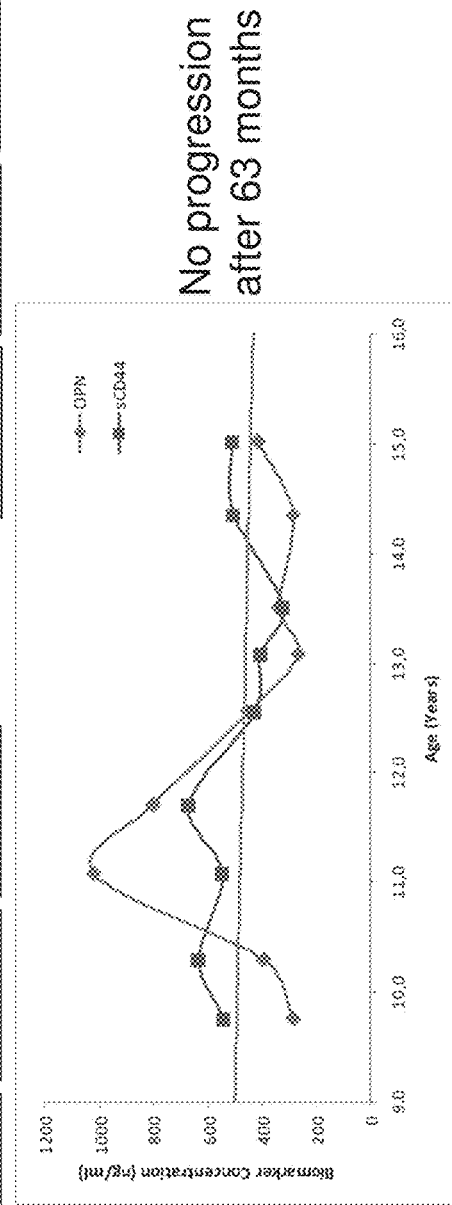
FIG. 16

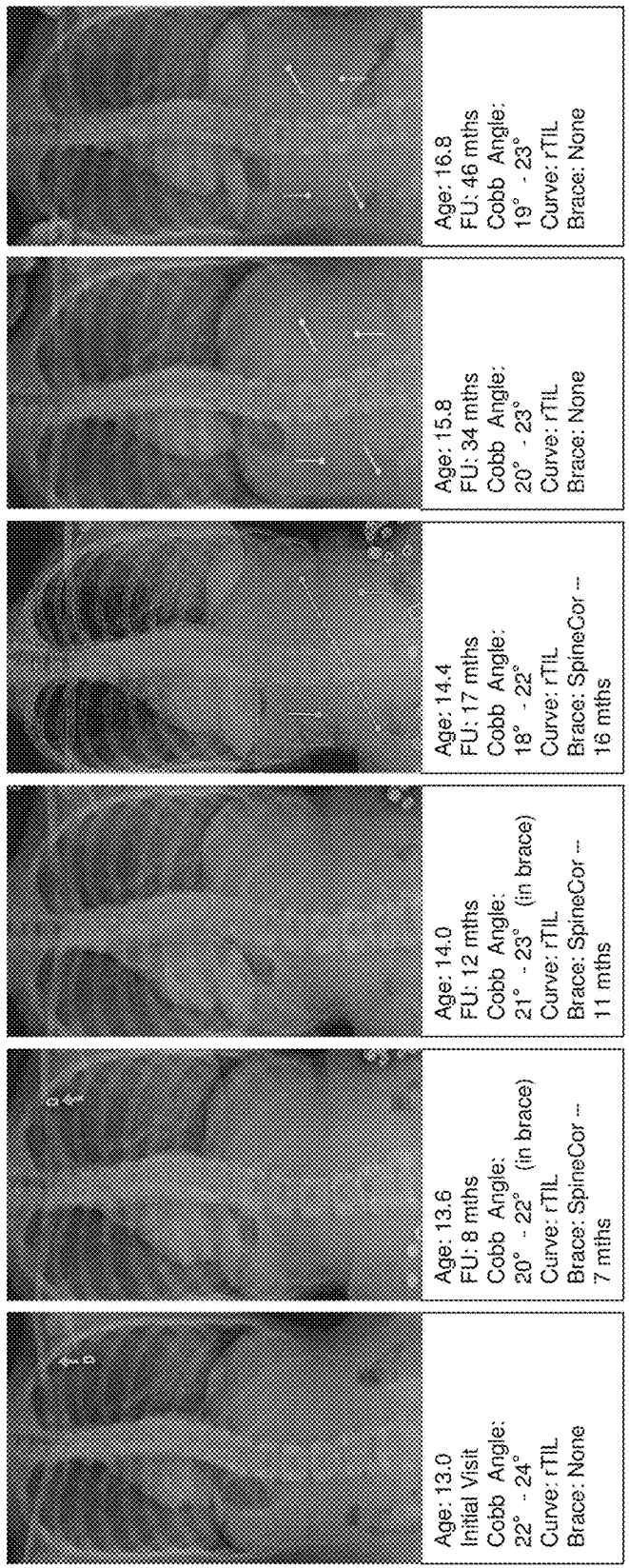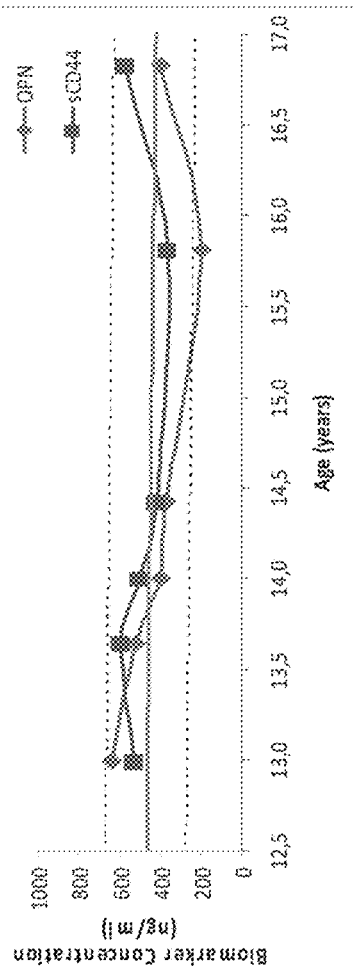
FIG. 18

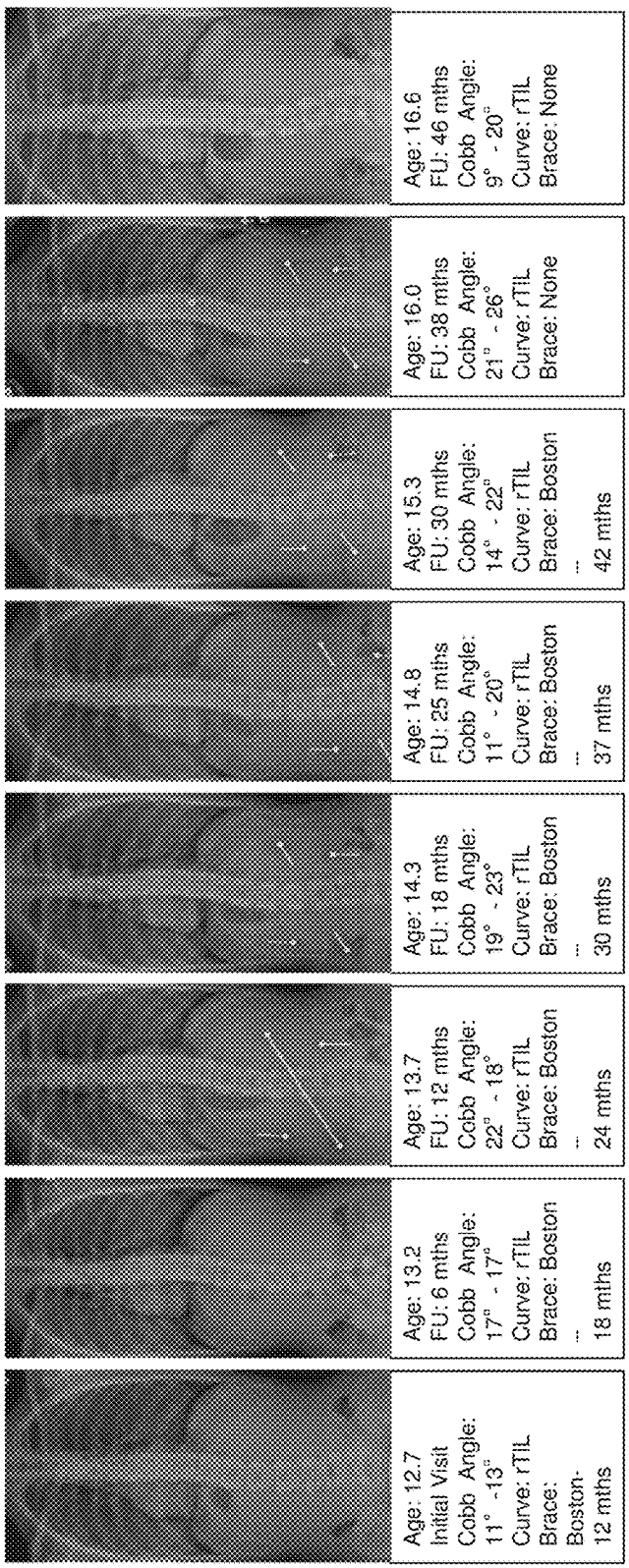
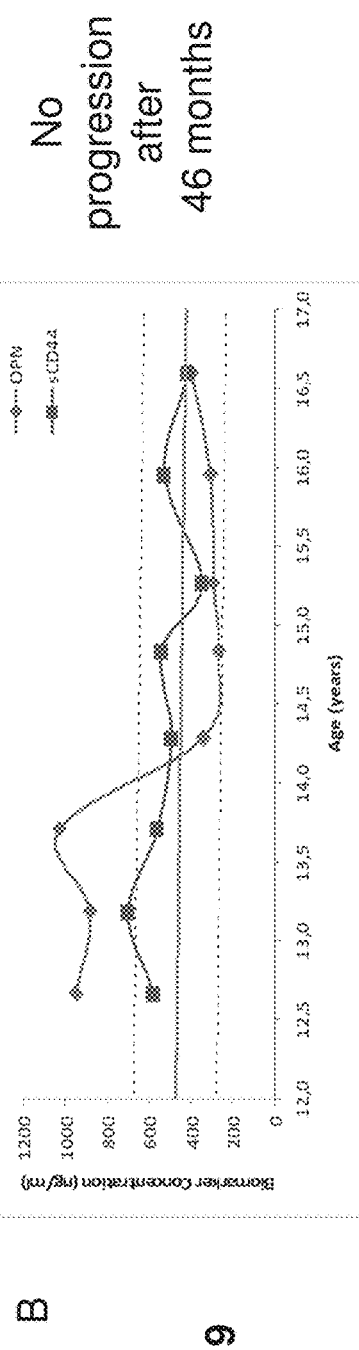
FIG. 19

METHOD OF TREATING AND PROGNOSING SCOLIOTIC PATIENT SUBGROUPS

CROSS REFERENCE TO RELATED APPLICATIONS

This application is a continuation of U.S. patent application Ser. No. 15/910,586, now abandoned, which is a divisional of U.S. patent application Ser. No. 14/917,786, now abandoned, which is a national phase entry under 35 U.S.C. § 371 of International Application No. PCT/CA2014/050852 filed Sep. 9, 2014 and published as International Publication No. WO 2015/032004A1, which claims priority from U.S. Provisional Application No. 61/875,162, filed Sep. 9, 2013 and U.S. Provisional Application No. 61/879,314, filed Sep. 18, 2013, all of which are incorporated herein by reference.

FIELD OF THE INVENTION

The present invention relates to Idiopathic Scoliosis (IS). More specifically, the present invention is concerned with endogenous osteopontin (OPN) levels, biological endophenotypes and IS treatment and prognostic.

REFERENCE TO SEQUENCE LISTING

This application contains a Sequence Listing in computer readable form entitled 14033_180_ST25, created on Sep. 8, 2020 having a size of 71 kilobytes, which is incorporated herein by reference.

BACKGROUND OF THE INVENTION

IS (e.g., Infantile Idiopathic scoliosis, Juvenile Idiopathic scoliosis or Adolescent Idiopathic scoliosis (AIS)) is a spine deformity of unknown cause generally defined as a lateral curvature greater than 10 degrees accompanied by a vertebral rotation 7. The condition affects 4% of the pediatric population and is most commonly diagnosed between the ages of 9 to 13 years 8, 9, 10.

Today in the United States there are approximately one million children between ages 10 and 16 with some degree of IS and about 100,000 children in Canada are diagnosed with IS. The total cost of diagnosis and monitoring of the scoliotic children by X-ray exposure is over $2.5 billion dollars annually in North America. Approximately, 10% of children diagnosed with idiopathic scoliosis have curve progression requiring corrective surgery [11]. About 29,000 scoliosis surgeries are done every year in North America, resulting in significant psychological and physical morbidity.

At the clinical level, the heterogeneity of IS is clearly illustrated by the variability of curve patterns, localisations and curve magnitude even in families with multiple affected members. In this regard, Applicants have previously discovered that scoliotic patients and subjects at risk of developing scoliosis are less responsive to Gi protein (inhibitory guanine nucleotide binding protein in G protein coupled receptors (GPCRs) also known as $G_i$ alpha subunit) stimulation when compared with healthy control subjects. The presence of a general differential Gi-signaling dysfunction allowed to stratify patients into three functional groups (FG1, FG2 and FG3) representing distinct biological endophenotypes. This impairment was measured in all cell types tested including bone-forming cells; muscle-forming cells and blood cells. Furthermore, because the Gi cellular response impairment is generalized and not specific to a particular receptor, any Gi-PCR ligand (e.g., agonist) can be used to classify subjects.

A first classification method is based on the percentage of degree of reduction (inhibitory response) relative to control group. The classification ranges were fixed between about 10 and 40% (or below 40%) of reduction of response relative to control group for FG3, about 40 and 60% for FG2 and above about 60% (e.g., between about 60% and 90%) for FG1. The same the classification ranges can be expressed as the percentage of maximal response relative to the control (as opposed to the % of reduction of response relative to the control). In such a case, the ranges are fixed between about 10-40% for FG1, about 40 and 60% for FG2 and about 60-90% for FG3. Both classification ranges can be used interchangeably (see, Moreau et al., 2004; Akoume et al., 2010; Akoume et al., 2013, Azeddine et al., 2007; Letellier et al., 2008; WO2003/073102, WO2010/040234 to Moreau, which are incorporated herein by reference in their entirety).

More recently, Applicants have modified this approach by demonstrating that the three functional groups can clearly be distinguished according to the profile of imbalance between response to Gi and Gs stimulation (i.e., Gi response minus Gs response or ratio between Gi/Gs stimulation or Gi/Gs-see PCT/CA2014/050562, which is incorporated herein by reference). It was found that the response to Gi stimulation predominated in FG3, while no apparent (i.e., no substantial or a very small) imbalance was observed in FG2. In contrast, FG1 subjects exhibited predominance for response to Gs stimulation. In addition, evidence was provided to the effect that patients belonging to the FG2 endophenotype are more at risk of progressing to the point of needing surgery (Julien et al., (2013)).

The differences in Gi-mediated cellular response observed among the three endophenotypes is a consequence of differences observed at the level of Gi protein phosphorylation. When $Gi\alpha$ proteins are phosphorylated they become inactive. The inventors have shown that the degree of serine phosphorylation of $Gi\alpha$ proteins can alternatively be used to classify subjects into a specific functional group. In FG1 subjects, all $Gi\alpha$ proteins ($Gi\alpha 1$-3) are phosphorylated and their level of serine phosphorylation is substantially higher than in control subjects. In FG2 subjects, $Gi\alpha 1$ and $Gi\alpha 2$ are phosphorylated, the level of $Gi\alpha 1$ and $Gi\alpha 2$ phosphorylation is higher than in control subjects and most $Gi\alpha 3$ proteins are not phosphorylated and thus, remain functional. Finally, in FG3 subjects $Gi\alpha 2$ and $Gi\alpha 3$ are phosphorylated, their level of phosphorylation is higher than in control subjects and most $Gi\alpha 1$ are not phosphorylated and thus remain functional 16.

The assessment of an imbalance between Gi and Gs coupled receptor signaling (as opposed to the assessment of a Gi-coupled receptor signaling impairment), greatly simplifies the risk assessment and endophenotype (functional group) assessment by eliminating the need of a reference signal from a control subject (see for example co-pending International Publication WO2014/201557, and co-pending International Publication WO2015/032005 to Moreau). The establishment of a reference signal is often difficult and may sometimes constitute an obstacle because the control subject(s) from whom the reference signal is derived should preferably match with age, gender, and medication, if any. Lifestyle (e.g., exercises and food) may also have some influence on the level of impairment, scoliosis marker level and individual cellular responses.

Finally, in International Publication WO2015/032005, Applicants further describe novel alternative methods of identifying subjects at risk of developing IS and of classifying IS subjects into a specific IS functional group. These methods improve current classification methods by providing distinct (unique) cellular responses for the specific functional groups thereby enabling to classify borderline subjects, which may not otherwise be identified as belonging to a specific functional group with sufficient confidence (high specificity) using other known methods.

In particular, Applicants have demonstrated that borderline subjects which cannot be unambiguously classified into a particular endophenotype subgroup using one or more of the above methods can be distinguished by assessing the effect of osteopontin (OPN) on the cellular response following Gi-stimulation (see International Publication WO2015/032005). Hence, subjects having a scoliosis or at risk of developing scoliosis can be identified by detecting an impairment in their cellular response following Gi stimulation and classified according to their Gi functional status (FG1, FG2 and FG3) without ambiguity.

A second method disclosed therein takes advantage of unique cellular impedance profiles following Gi-protein stimulation in four GiPCR clusters (I, II, Ill and IV). The impedance profile for each cluster has a different shape. In addition, in the case of GiPCR cluster II, only FG1 subject show an impedance profile comprising a characteristic negative impedance phase followed by a positive phase, thereby enabling to easily distinguish FG1 subjects from FG2 and FG3 subjects. Finally, a third classification method is based on the demonstration that FG1 subjects can further be distinguished over FG2 and FG3 subjects based on their cellular response to GiPCR cluster I and/or II stimulation in the presence of high concentration of PTX. Following GiPCR cluster I or cluster II agonist stimulation, the cellular response curve in the presence of PTX is characterized by a first phase in which the response decreases with increasing amounts of PTX followed by a second phase where the response increases with increasing amounts of PTX (V shape curve). In the second phase of the response, the % of response relative to administration of a control vehicle is above that of the corresponding % of response for control (subjects not having IS or not at risk of developing IS), FG2 and FG3 subjects. Hence, a magnitude of cellular response in the presence of high concentration of PTX that is above that of a control (subjects not having IS or not at risk of developing IS as well as FG2 and FG3 subjects) indicates that the subjects belongs to the FG1 functional group.

Once diagnosed, the primary concern for physicians in managing scoliotic children is whether the curve will progress. Indeed, the curve progression is often unpredictable and is more frequently observed among girls than in boys 12. If untreated, the curve can progress dramatically, creating significant physical deformity and even cardiopulmonary problems. These manifestations become life threatening when the curve exceeds 70 degrees 13,14. The current treatment options to prevent or stop curve progression include bracing and surgery. In general, bracing is recommended for curves between 25 and 40 degrees, while surgery is reserved for curve greater than 45 degrees or curves that are unresponsive to bracing.

All diagnosed IS children are subjected to multiple radiographs over several years, usually until they reach skeletal maturity. Patients with a curve that is between 20 to 30 degrees will usually be observed at 4 to 6 months intervals with an x-ray test to measure the curve. Any progression that is less than 5 degrees is not considered significant. If the curve progresses more than 5 degrees, then the curve will need treatment. In general, treatment with a back brace will be recommended for patients: i) having a curve of about 25 to 40 degrees, and; ii) who are still growing i.e. patients who are skeletally immature (e.g., girls who are about 11 to 13 years old, and boys who are about 12 to 14 years, Risser between 0 and 3). Brace treatment is typically used in girls up to one/-two years after menarche, the onset of the female menstrual cycle. Brace treatment will often be maintained after menarche until curve progression has stabilized for 1-2 years, but may be stopped when skeletal maturity is reached. If an older child has a curve greater than 30 degrees and is almost mature (Risser of 4-5), his or her curvature will often be treated with observation only, as there is little growth left and bracing is unlikely to be as effective. The only curves that tend to progress after skeletal maturity are those that are greater than 50 degrees in angulation, so the treatment objective with the back brace is to try to bring the child into adulthood with less than a 50-degree curvature.

Typically, if the curve continues to progress to 40-45 degrees or more, a spinal fusion surgery will usually be recommended. However, even if surgery eventually becomes necessary, the back brace can still be beneficial by helping delay the progression of the curvature and allowing optimal growth for the child before undergoing spinal fusion (which ends the spine growth).

Unfortunately, some patients do not respond or respond poorly to bracing, and their spinal curves continue to progress. Currently, there is no approved method or test available to predict which affected individuals are likely to benefit from bracing and which individuals are likely to experience a curve progression requiring surgery, despite brace treatment.

It would be advantageous to identify prior to treatment subjects likely to benefit from brace treatment (or other scoliosis treatment) from those unlikely to benefit from it or likely to worsen following treatment. Curves that progress can require fusion surgery and/or lead to potential long-term health problems. Even for patients unlikely to worsen after brace treatment, it would be advantageous to avoid the treatment if it is unnecessary or ineffective: while it is non-invasive, bracing for scoliosis is in itself a very difficult treatment option for many patients and may have a significant psychological impact. Early knowledge of bracing treatment outcome could therefore help IS treatment by avoiding unnecessary bracing and by enabling the selection of the most appropriate treatment for a given individual early on during the course of the disease.

The present description refers to a number of documents, the content of which is herein incorporated by reference in their entirety.

SUMMARY OF THE INVENTION

Mechanotransduction (biomechanics and bodily responses to mechanical stimuli) is involved in IS development as well as its non-surgical treatments (i.e., bracing, physical therapies). Mechanotransduction is a relatively new and emerging angle of research in the field of IS (e.g., AIS) study that holds many possibilities for novel personalized therapeutic options. Knowledge of the specific genes and biochemical pathways that are altered because of mechanotransduction differences in scoliosis could significantly change the diagnosis and treatment of IS.

In this context, the present invention identified that certain mechanotransductive genes (e.g., SSP1 encoding OPN; SPP1-Gene ID: 6696, OPNa: NP_001035147.1, OPNb:

NP_000573.1, OPNc: NP_001035149.1, OPN Isoform 4: NP_001238758.1, OPN Isoform 5: NP_001238759.1, NM_001251829.1, GI_352962173) and pathways are distinctive between FG1 and the two other IS functional groups (FG2 and FG3). The present invention is based in part on the discovery that depending on their Gi functional status (FG1, FG2 or FG3), subjects suffering from IS do not equally respond to bracing and OPN.

The present inventors have found that subjects of the FG3 functional group are more likely than those of the FG2 functional group to have successful brace treatment, while subjects belonging to the FG1 group are the least likely to have successful brace treatment and their condition could even be aggravated by brace treatment. They have also found that OPN has a protective effect in subjects belonging to the FG1 functional group while it is a risk factor in the subjects of the FG2 and FG3 functional groups. Indeed, it was unexpectedly found that OPN increases the Gi-mediated response in FG1 subjects while it further decreases (aggravates) the impairment observed in the Gi-mediated response of FG2 and FG3 functional groups. This illustrates the heterogeneity of mechanical response on a biological level among IS patients and could explain why some patients are considered as brace-responders while for others, bracing cannot stop curve progression.

Accordingly, the present invention provides a method of predicting brace treatment outcome in a subject in need thereof comprising classifying the subject into functional group FG1, FG2 or FG3, wherein the classification enables the prediction of brace treatment outcome.

In a specific embodiment, the classification of the subject into the FG2 or FG3 functional group is indicative that the subject is likely to benefit from brace treatment. In another specific embodiment, the classification of the subject into the FG1 functional group is indicative that the subject is unlikely to benefit from brace treatment. In another specific embodiment, the classification of the subject into the FG2 or FG3 functional group is indicative that the subject is likely to have a successful brace treatment. In another specific embodiment, the classification of the subject into the FG1 functional group is indicative that the subject is unlikely to have a successful brace treatment. In another specific embodiment, the classification of the subject into the FG2 or FG3 functional group is indicative that the subject has a decreased risk of curve progression following brace treatment. In another specific embodiment, the classification of the subject into the FG1 functional group is indicative that the subject has an increased risk of curve progression following brace treatment. In another specific embodiment, the classification of the subject into the FG2 or FG3 functional group is indicative that the subject has a decreased risk of requiring surgery following brace treatment. In another specific embodiment, the classification of the subject into the FG1 functional group is indicative that the subject has an increased risk of requiring surgery following brace treatment. In another specific embodiment, the method further comprises measuring the level of OPN in a blood sample from the subject prior to the beginning of brace treatment. In another specific embodiment, the classification of the subject into the FG1 functional group and a high level of OPN in the blood sample from the subject is indicative that the subject is further unlikely to benefit from brace treatment. In another specific embodiment, the classification of the subject into the FG1 functional group and a low level of OPN level in the blood sample from the subject is indicative that the subject may benefit from a short brace treatment. In another specific embodiment, the classification of the subject into the FG2 or FG3 functional group and a high level of OPN in the blood sample from the subject is indicative that the subject is further likely to benefit from brace treatment.

In another specific embodiment, the brace treatment comprises treatment with a Thoraco-Lumbo-Sacral-Orthosis (TLSO) brace, a Milwaukee brace, a Charleston brace, a SpineCor™ brace or any combination thereof. In another specific embodiment, the brace treatment comprises treatment with a Thoraco-Lumbo-Sacral-Orthosis (TLSO) brace.

In accordance with another aspect of the present invention, there is provided a method of predicting the risk of developing idiopathic scoliosis in a subject in need thereof comprising: classifying the subject into functional group FG1, FG2 or FG3; measuring the level of OPN in a blood sample from the subject, wherein a classification of the subject into the FG1 functional group and a low level of OPN or a classification of the subject into the FG2 or FG3 functional group and a high level of OPN is indicative that the subject has an increased risk of developing idiopathic scoliosis. In a specific embodiment, the risk of developing scoliosis is a risk of curve progression.

In accordance with yet another aspect of the present invention, there is provided a method of treating a subject suffering from an idiopathic scoliosis or at risk of developing an idiopathic scoliosis comprising classifying the subject into functional group FG1, FG2 or FG3, wherein when the subject is classified into the FG1 functional group, the subject is not treated with a brace; and when the subject is classified into the FG2 or FG3 functional group, the subject is treated with a brace.

In accordance with yet another aspect of the present invention, there is provided a method of treating a subject in need thereof comprising classifying the subject into functional group FG1, FG2 or FG3, wherein when the subject is classified into the FG1 functional group, the subject is treated with OPN or an OPN agonist or with treatment or preventive measures which increase the level or activity of circulating OPN; and when the subject is classified into the FG2 or FG3 functional group, the subject is treated with an OPN antagonist or with treatment or preventive measures which decrease the level or activity of circulating OPN.

In accordance with yet another aspect of the present invention, there is provided a method of treating a subject in need thereof comprising a) classifying the subject into functional group FG1, FG2 or FG3; and b) determining the level of OPN in a blood sample from the subject, wherein when the subject is classified into the FG1 functional group and the level of OPN is high, the subject is not treated with a brace; when the subject is classified into the FG1 functional group and the level of OPN is low, the subject is optionally treated with a brace for a short period of time; and when the subject is classified into the FG2 or FG3 functional group the subject is treated with a brace.

In a specific embodiment, when the subject is classified into functional group FG1, the subject is further treated with OPN or an OPN agonist or with treatment or preventive measures which increase the level or activity of circulating OPN. In another specific embodiment, when the subject is classified into functional group FG2 or FG3, the subject is further treated with an OPN antagonist or with treatment or preventive measures which decrease the level or activity of circulating OPN.

In a related aspect, the present invention provides a method of treating a subject in need thereof comprising classifying the subject into functional group FG1, FG2 or FG3, wherein (i) when the subject is classified into the FG1 functional group, the level of OPN or the activity of OPN in said subject is increased; and (ii) when the subject is classified into the FG2 or FG3 functional group, the level of OPN or the activity of OPN in said subject is decreased. In an embodiment, i) comprises treating said subject with: (a) OPN; (b) an OPN agonist;(c) a treatment or preventive measure which increases the level of circulating OPN; (d) an inhibitor of CD44 expression or activity; or (e) a combination of at least two of (a) to (d). In an embodiment, ii) comprises treating said subject with: (f) an OPN antagonist; (g) a treatment or preventive measure which decreases the level of circulating OPN; (h) an inhibitor of integrin expression or activity; (i) sCD44 or a stimulator of CD44 expression; or (j) a combination of at least two of (f) to (i).

In an embodiment, the OPN agonist is (b i) HA; (b ii) an OPN functional fragment; (b iii) an OPN functional derivative; or (b iv) a combination of at least two of (b i) to (b iii). In an embodiment the treatment or preventive measure which increases the level of circulating OPN comprises applying pulsative compressive pressure for 15-90 minutes on at least one body part of said subject. In an embodiment the treatment or preventive measure which increases the level of circulating OPN comprises applying low intensity pulse ultrasound (LIPUS). In an embodiment the inhibitor of CD44 expression or activity is an antibody which binds to CD44 or a siRNA or antisense specific for CD44. In an embodiment the OPN antagonist is (f i) melatonin; (f ii) selenium; (f iii) an antibody which binds to OPN; (f iv) an siRNA or antisense specific for OPN; (f v) a molecule that blocks the binding of OPN to integrins; or (f vi) a combination of at least two of (f i) to (f vi). In an embodiment the treatment or preventive measure which decreases the level of circulating OPN is:(g i) brace treatment; (g ii) acupoint heat sensitive moxibustion; (g iii) heat therapy with pad; (g iv) electroacupuncture; (g v) thermal bath; or (g vi) a combination of at least two of (g i) to (g v). In an embodiment the molecule that blocks the binding of OPN to integrins is a RGD peptide or derivative thereof. In an embodiment the molecule that blocks the binding of OPN to integrins is a peptide fragment of OPN comprising a RGD motif. In an embodiment the peptide fragment of OPN comprises the amino acid sequence GRGDSVVYGLRS (SEQ ID NO: 13). In an embodiment the inhibitor of integrin activity is (h i) an antibody that binds specifically to integrin subunit $\alpha_5$; (h ii) an antibody that binds specifically to integrin subunit $\beta_1$; (h iii) an antibody that binds specifically to integrin subunit $\beta_3$; (h iv) an antibody that binds specifically to integrin subunit $\beta_5$; (h v) an antibody that binds specifically to integrin subunits $\alpha_5\beta_1$; or (h vi) a combination of at least two of (h i) to (h v). In an embodiment the inhibitor of integrin activity is volociximab™; ATN-161, etaratuzumab™, etaracizzumab™, Vitaxin™, MEDI-522, CNT095 or Cilengitide™. In a particular embodiment the inhibitor of integrin activity is volociximab™ or Cilengitide™. In a particular embodiment of the methods of the present invention, integrin is $\alpha_5\beta_1$. In an embodiment, the inhibitor of integrin expression is (h i) an siRNA or antisense specific to integrin subunit $\alpha5$; (h ii) an siRNA or antisense specific to integrin subunit $\beta1$; (h iii) an siRNA or antisense specific to integrin subunit $\beta3$; (h iv) an siRNA or antisense specific to integrin subunit $\beta5$; (v) a combination of at least two of (h i) to (h vi).

In a particular aspect, the above treatment methods further comprise treating the subject with a brace.

In another specific embodiment, the above methods of the present invention further comprise measuring the level of OPN in a blood sample from the subject periodically. In another specific embodiment, the level of OPN is measured once a month.

In another specific embodiment, the high level of OPN in the blood sample of the subject is between about 600-1000 ng/ml. In another specific embodiment, the low level of OPN in the blood sample of the subject is ≤500 ng/ml.

In another specific embodiment, the subject is a pediatric subject.

In another specific embodiment, the classification comprises determining changes in cellular impedance following Gi-stimulation in a cell sample from the subject. In another specific embodiment, the cellular impedance is measured by cellular dielectric spectroscopy (CDS). In another specific embodiment, the classification comprises measuring changes in cAMP concentration following Gi-stimulation in a cell sample from the subject. In another specific embodiment, the classification comprises determining the phosphorylation pattern of Giα proteins in a cell sample from the subject. In another specific embodiment, the classification comprises determining cellular proliferation of a cell sample from the subject.

In another specific embodiment, the subject is a subject diagnosed with Idiopathic Scoliosis (IS). In another specific embodiment, the Idiopathic Scoliosis is Adolescent Idiopathic Scoliosis (AIS).

In accordance with another aspect of the present invention, there is provided a kit for predicting brace treatment outcome in a subject suffering from Idiopathic Scoliosis or for predicting the risk of developing severe Idiopathic Scoliosis comprising reagents for classifying a subject into functional group FG1, FG2 or FG3. In a specific embodiment of the kit, the kit comprises at least two of (i) a ligand for Gi stimulation; (ii) a ligand for detecting Giα proteins phosphorylation; and/or (iii) reagents for detecting cellular proliferation. In a specific embodiment of the kit, the kit further comprises: (i) a ligand for Gs stimulation; (ii) reagents for detecting the level of OPN; and/or (iii) instructions for predicting brace treatment outcome.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 1A and 1B presents possible treatment options depending on the functional status of the subject and the level of circulating OPN in the blood sample of the subject. FIG. 1A. Brace treatment options depending on the subject's functional group and on the circulating level of OPN. FIG. 1B. Complementary/alternative treatment options according to the functional status of the subject;

FIG. 3A shows OPN circulating levels variation in blood samples of AIS subjects having low initial OPN circulating levels (e.g., below about 600 ng/ml) and FIG. 3B shows OPN circulating levels variation in blood samples of AIS subjects having high initial OPN circulating levels (e.g., at or above about 600 ng/ml);

FIGS. 4A-4B shows curve progression and subject's clinical information (FIG. 4A) and OPN and sCD44 levels variation (FIG. 4B) with time in blood samples from a female FG1 AIS subject (#593);

FIG. 5A shows OPN and sCD44 levels variation; and FIG. 5B shows curve progression and subject's clinical information with time in blood samples from a female FG1 AIS subject (#148);

FIG. 6A shows OPN and sCD44 levels variation; and FIG. 6B shows curve progression and subject's clinical information with time in blood samples from a male FG1 AIS subject (#393);

FIG. 7A shows OPN and sCD44 levels variation; and FIG. 7B shows curve progression and subject's clinical information with time in blood samples from a male FG1 AIS subject (#498);

FIG. 8A shows OPN and sCD44 levels variation; and FIG. 8B curve progression and subject's clinical information (B) with time in blood samples from a female FG1 AIS subject (#530);

FIG. 9A shows OPN and sCD44 levels variation; and FIG. 9B curve progression and subject's clinical information with time in blood samples from a female FG1 AIS subject (#627);

FIG. 10A shows OPN and sCD44 levels variation; and FIG. 10B shows curve progression and subject's clinical information with time in blood samples from a female FG1 AIS subject (#675);

FIG. 11A shows OPN and sCD44 levels variation; and FIG. 11B shows curve progression and subject's clinical information with time in blood samples from a female FG1 AIS subject (#394);

FIGS. 12A-12B: FIG. 12A shows curve progression and subject's clinical information and FIG. 12B shows OPN and sCD44 levels variation with time in blood samples from a female FG1 AIS subject (#679);

FIG. 13A shows OPN and sCD44 levels variation; and FIG. 13B shows curve progression and subject's clinical information with time in blood samples from a female FG1 AIS subject (#460);

FIG. 14A shows OPN and sCD44 levels variation; and FIG. 14B shows curve progression and subject's clinical information with time in blood samples from a female FG1 AIS subject (#789);

FIG. 15A shows OPN and sCD44 levels variation; and FIG. 15B shows curve progression and subject's clinical information with time in blood samples from a female FG1 AIS subject (#144);

FIGS. 16A-16B: FIG. 16A shows curve progression and subject's clinical information and FIG. 16B shows OPN and sCD44 levels variation with time in blood samples from a female FG2 AIS subject (#208);

FIG. 17A shows curve progression and subject's clinical information and FIG. 17B shows OPN and sCD44 levels variation with time in blood samples from a female FG2 AIS subject (#159);

FIGS. 18A-18B: FIG. 18A shows curve progression and subject's clinical information and FIG. 18B shows OPN and sCD44 levels variation with time in blood samples from a female FG2 AIS subject (#272);

FIGS. 19A-19B: FIG. 19A shows curve progression and subject's clinical information and FIG. 19B shows OPN and sCD44 levels variation with time in blood samples from a female FG3 AIS subject (#301);

(FIGS. 24A, 24C and 24D) In osteoblasts from control, FG2 and FG3 subjects, the inhibition of OPN on Gi-mediated cell signaling can be reversed by antibodies against integrins $\beta_1$, $\beta_3$ and $\beta_5$ while inhibition of CD44 using an anti-CD44 antibody further reduced (aggravated) Gi-mediated signaling in FG2 and FG3 subjects and potentiated the effect of OPN. Inhibition of integrin $\beta_1$ was most effective; (FIG. 24B) In osteoblasts from FG1 subjects, antibodies against integrins $\beta_1$, $\beta_3$ and $\beta_5$ have an opposite effect and reduced (blocked) the increase in Gi-mediated response induced by OPN, although to a lesser extent. Conversely, inhibition of CD44 using a CD44 antibody, increased the Gi-mediated response in FG1 subjects; (FIGS. 25A, 25C and 25D) In osteoblasts from control, FG2 and FG3 subjects, the inhibition of OPN on Gi-mediated cell signaling can be reversed by siRNAs against integrins $\beta_1$, $\beta_3$ and $\beta_5$ while inhibition of CD44 using an siRNA further reduced Gi-mediated signaling and potentiated the effect of OPN (FIG. 25B) In osteoblasts from FG1 subjects, siRNAs against integrins $\beta_1$, $\beta_3$ and $\beta_5$ had an opposite effect and reduced (blocked) the increase in Gi-mediated response induced by OPN but in a less or non-significant extent.

DESCRIPTION OF ILLUSTRATIVE EMBODIMENTS

Figure 2:
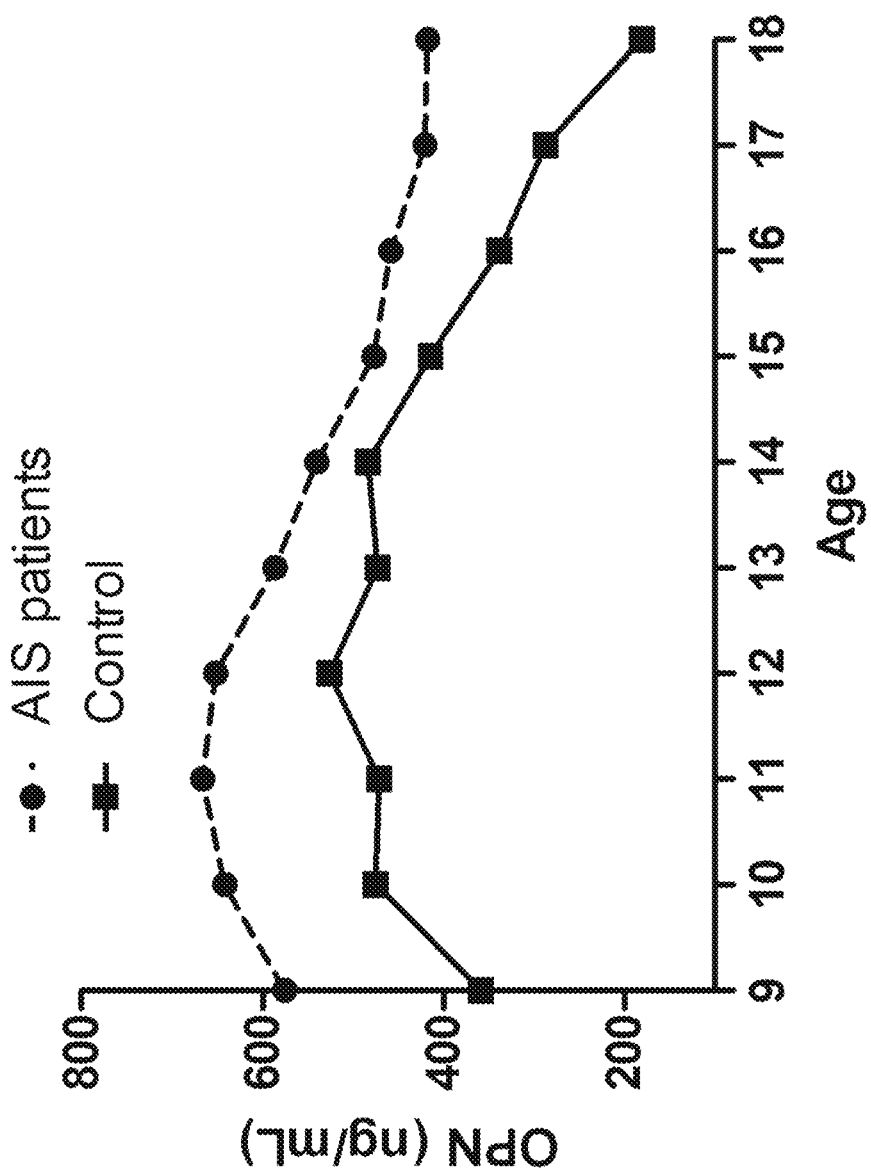
FIG. 2 shows OPN circulating levels between age 9 and 18 in controls and AIS subjects.

Applicants have assessed whether circulating OPN levels have the same effect with regards to Gi-mediated response and risk of developing scoliosis among the three functional groups and have undertaken a retrospective study with IS subjects to determine whether patient bracing outcome could be differentiated based on their Gi functional status (FG1, FG2 and FG3).

The present invention is based on the findings that i) OPN has a differential (opposite) effect on the response to Gi stimulation among IS functional groups (it decreases the Gi-mediated response in control, FG2 and FG3 subjects while it increases the Gi-mediated cellular response in FG1 subjects); ii) inhibition of the expression or activity of CD44 (a receptor for OPN) potentiates the effect of OPN; iii) Hyaluronic acid (HA) (which binds to CD44 receptor with higher affinity than OPN) also has a differential effect on Gi-mediated cellular response (it decreases the Gi-mediated response in control, FG2 and FG3 subjects while it increases the Gi-mediated cellular response in FG1 subjects; iv) inhibition of the expression or activity of integrins (which bind OPN) reduce the effect of OPN on the Gi-mediated cellular response in FG2 and FG3 subjects; v) high circulating OPN level in FG1 subjects has a protective effect while it is a risk factor in FG2 and FG3 subjects; vi) brace treatment outcome is most favorable in FG2 and FG3 subjects (mainly in FG3); vii) bracing is less effective in FG1 subjects with significant increased likelihood to progress over 45° and to have surgery than the other 2 groups; and viii) bracing generally decreases circulating OPN levels in all AIS subjects. Taken together, these results enable to improve IS treatment, to more accurately predict brace treatment outcome and to select the most appropriate treatment method and follow up schedule for each patient according to their biological endophenotype (FG1, FG2 and FG3) and/or circulating OPN level.

IS patient bracing outcome was evaluated in regard to curve progression leading up to surgery between the 3 functional groups (FG1, FG2 and FG3). Each patient had been previously classified in one of the 3 functional groups (FG1, FG2 or FG3) using a cell-based assay measuring cAMP (Moreau et al., 2004) variation and/or CDS response (Akoume et al., 2010) following Gi stimulation. Outcome of brace treatment in terms of curve progression over 45° and occurrence of corrective surgery was determined for each functional group. It was found that bracing is less effective in FG1, with an increased likelihood to progress over 45° and to have surgery than the other 2 groups. Outcomes of bracing were most favorable for patients presenting the FG3 endophenotype.

Applicants have determined that subjects classified in the FG1 functional group are less likely to benefit from bracing. Furthermore, FG1 subjects having high level of OPN (e.g., above 1000 ng/ml) are less likely to progress than FG1 subjects having low levels of OPN (≤500 ng/ml). Results suggest that in FG1 subjects, when the level of OPN decreases around 500 ng/ml or below, scoliosis tend to progress (i.e., increase in Cobb's angle). These results are consistent with applicant's findings that in the FG1 functional group, OPN reduces the Gi-mediated signaling defect (i.e., increases Gi-mediated cell signaling) generally present in scoliosis subjects. Applicants have also determined that brace treatment generally decreases OPN levels by way of a retroinhibition mechanism and that effect of brace treatment may further be distinguished based on initial circulating OPN levels prior to beginning of treatment. Indeed, it was found that in certain subjects having initial low level of circulating OPN, brace treatment first induces a sharp rise in OPN levels (within the first 6 months) while it induces a sharp decrease in OPN levels in subjects having high initial OPN levels, thereby supporting a retroinhibition mechanism controlling circulating OPN levels in vivo. Furthermore, Applicants have found that high circulating OPN levels have a protective effect on patients of functional group FG1 and have a detrimental effect (i.e., increasing their risk of developing a scoliosis) in subjects classified into the FG2 and FG3 functional groups.

Accordingly, FG1 subjects (especially having a high level of circulating OPN) should generally not be prescribed brace treatment even if very short. Subjects of the FG2 and FG3 functional groups are more likely to benefit from brace treatment (e.g., long term brace treatment) possibly because it generally decreases OPN levels and an elevated OPN level is a risk factor for these subjects.

Hence, further combining endophenotype classification with OPN circulating levels allows to further distinguish among functional groups which subjects should be treated with a brace, which subjects should have their level or activity of OPN lowered (e.g., FG2 and FG3 subjects), which subject should have their level or activity of OPN increased (FG1 subjects), which subjects should have their level of CD44 (e.g., sCD44) increased (FG2 and FG3); which subjects should have their level of CD44 (e.g., sCD44) decreased (e.g., FG1); which subjects should have their level of HA increased (FG1); which subjects should have their level of HA decreased (FG2 and FG3); which subjects should have their level or activity of integrins (e.g., $\alpha_5$, $\beta_1$, $\beta_3$ and $\beta_5$) decreased (FG2 and FG3); as well as the optimal duration of treatment. Other treatment regimens known to have an effect on OPN, HA, CD44 or integrins level or activity may also be adapted according to each specific functional group (e.g., specific exercises or massages (e.g., application of compressive pressure for 15 to 90 minutes—See for example U.S. Ser. No. 13/822,982, and low intensity pulsed ultrasounds (LIPUS), for FG1 patients, because such approaches can increase OPN expression level (e.g., OPN plasma level)), acupoint heat sensitive moxibustion or heat therapy with pad, thermal bath, electroacupuncture (for FG2 and FG3 subjects because such approaches are known to decrease OPN levels in serum of subjects). These findings enable personalized treatment prescription according to each patient Gi-endophenotype and/or OPN level, early on following diagnosis thereby avoiding unnecessary delay in finding best treatment options which will ultimately improve IS treatment outcome.

Accordingly, the present invention provides a method of predicting brace treatment outcome in a subject in need thereof comprising; i) classifying the subject into functional group FG1, FG2 or FG3, wherein the classification enables the prediction of brace treatment outcome.

Specifically, according to the above method, classification of the subject into the FG1 functional group is indicative that the subject: i) is less likely to benefit from brace treatment (e.g., is less likely to have brace treatment success); ii) is more likely to require surgery; iii) is more likely to show a curve progression >6° in Cobb's angle; iv) is less likely to have a Cobb angle ≤ to 45°; and v) is more likely to aggravate his/her condition (e.g., increase speed of curve progression or increased final Cobb angle) by brace treatment as compared to FG2 and FG3 functional groups.

According to the above brace treatment outcome prediction method, classification of the subject into the FG3 functional group is indicative that the subject: i) is more likely to benefit from brace treatment (e.g., is more likely to have brace treatment success); ii) is less likely to require surgery; iii) is less likely to show a curve progression >6° in Cobb's angle; iv) is more likely to have a Cobb angle to 45°;

and v) that the subject is less likely (or unlikely) to aggravate his/her condition (e.g., increase speed of curve progression or increased final Cobb angle) by brace treatment as compared to FG1 and FG2 functional groups.

Finally, classification of the subject into the FG2 functional group according to the above brace treatment outcome prediction method is indicative that the subject: i) has moderate chances of benefiting from brace treatment (e.g., the subject has moderate chances of brace treatment success); ii) has moderate risk of requiring surgery; iii) has moderate risk to show a curve progression >6° in Cobb's angle; iv) has moderate risk of having a Cobb angle ≤ to 45°; and v) has low risk of aggravating his/her condition (e.g., increase speed of curve progression or increased final Cobb angle) by brace treatment as compared to FG1 and FG3 functional groups.

Under certain circumstances, certain rare FG1 subjects could nevertheless benefit from a short brace treatment if, in such patients bracing increases OPN level. It was found that subjects in each functional group may further be distinguished based on their level of circulating OPN (low or high level of OPN). In order to further distinguish among each groups which subjects could benefit from brace treatment, the present prediction method can advantageously further comprise measuring the level of circulating OPN prior to the beginning of brace treatment. According to this method, certain subjects classified into the FG1 functional group and having a low level of circulating OPN (e.g., below 500 ng/ml) may benefit from a short brace treatment (e.g., 6 months or less) and are less likely to aggravate their condition by short treatment than FG1 subjects having high levels of circulating OPN because brace treatment can induce an increase in circulating OPN in these subjects at the beginning of treatment and OPN has a protective effect in these subjects. The short brace treatment may be for 18 months or less, preferably 12 months or less and more preferably, 6 months or less or until OPN concentration is at its maximal concentration or close to its maximal concentration (i.e., below the retroinhibition concentration). It should be noted that if an FG1 subject is treated with a brace, his/her OPN level should be monitored closely in order to detect any drop in circulating OPN. Preferably, brace treatment would be pursued only if and while bracing induces an increase in OPN level. If a drop in circulating OPN level is detected, then brace treatment should be stopped.

According to the above method, subjects classified into the FG2 or FG3 functional group and having a high level of circulating OPN may more rapidly benefit from brace treatment than FG2 or FG3 subjects having low levels of circulating OPN because OPN is a risk factor in these subjects and brace treatment reduces the level of circulating OPN in these subjects. In subjects of the FG2 and FG3 functional groups having a low level of circulating OPN, brace treatment is nevertheless beneficial but is preferably maintained for a sufficient time so that the level of OPN level is decreased (e.g., 12-18 months and preferably more than 18 months).

In a related aspect, the present invention also encompasses selecting the most efficient and least invasive known preventive action, treatment or follow-up schedule in view of the determined classification and concentration of circulating OPN level.

Accordingly, the present invention provides a method of treating or preventing IS in a subject comprising, classifying the subject into functional group FG1, FG2 or FG3, wherein when the subject is classified into the FG1 functional group: i) the subject is treated with OPN; ii) the subject is treated with an OPN agonist (e.g., HA supplements or treatment or preventive measures which increase HA level such as a HA rich diet); iii) the subject is treated with a CD44 antagonist (e.g., an antibody against CD44); iv) the subject is treated with an integrin agonist (or the subject is prescribed treatment or preventive measures which increase integrin level or activity); iv) the subject is prescribed treatment or preventive measures which increase circulating OPN levels (e.g., massages such as by compressive pressure as described in U.S. Ser. No. 13/822,982; low intensity pulsed ultrasound (LIPUS), etc.); v) the subject is prescribed treatment or preventive measures which decrease CD44 level or activity (e.g., siRNA specific for CD44 or antibody which blocks CD44 binding to OPN); and vi) any combinations of i) to v); and wherein when the subject is classified into functional group FG2 or FG3, the subject is vii) treated with an OPN antagonist (e.g., OPN antibody, OPN siRNA, melatonin, vitamin D, PROTANDIM™ (nutraceutical cocktail known to reduce plasma or serum OPN levels and used as a natural anti-oxidant mix), an inactive OPN derivative or analog blocking one or more OPN receptors (e.g., $\alpha_5\beta_1$, $\alpha_4\beta_1$, $\alpha_9\beta_1$, and $\alpha_9\beta_4$)); viii) the subject is treated with sCD44 or a CD44 agonist; ix) the subject is treated with an integrin antagonist (e.g., RGD peptide or derivative thereof, a synthetic peptide acting as specific $\alpha_v$ integrin inhibitor (e.g. cilengitide™) or monoclonal antibodies targeting specifically integrin (volociximab™ ($\alpha_5\beta_1$); etaratuzumab™ ($\alpha_v\beta_3$), etaracizzumab™ ($\alpha_v\beta_3$), vitaxin ($\alpha_v\beta_3$), MEDI-522 ($\alpha_v\beta_3$)) or anti-$\alpha_v$ integrin (CNT095); or x is prescribed treatment or preventive measures which reduce the level of circulating OPN (e.g., brace treatment, acupoint heat sensitive moxibustion, heat therapy with pad, thermal bath, electroacupuncture, etc.); xi) the subject is prescribed treatment or preventive measures which increase CD44/sCD44 level; xii) the subject is prescribed treatment or preventive measures which decrease HA level (e.g., HA-poor diet); xiii) the subject is prescribed an integrin antagonist (e.g., an antibody or siRNA specific for integrin α5, β1, β3 and β5 or treatment or preventive measures which decrease integrin level or activity); and xiv) any combinations of vii) to xiii). In addition to the above, non-limiting treatments or preventive measures include: exercises (physiotherapy), orthodontic treatment, and administration of other natural substances increasing or reducing OPN, CD44 and HA levels. Once a subject is classified into a specific functional group, his/her OPN levels are preferably monitored periodically. When a new treatment or preventive measure is prescribed OPN levels should be monitored in order to maintain the optimal level of OPN (e.g., below or above the OPN retroinhibition/retroactivation concentrations) for this subject and detect any variation that could potentially accelerate the development of IS (including curve progression).

Accordingly, the above treatment or prevention method may further be improved by measuring the level of circulating OPN in the subject and determining whether the subject has a high or low level of circulating OPN. Determination of the level of circulating OPN (and of its variation with time) enables to more appropriately select the best treatment option and follow-up schedule. FIG. 1 summarizes treatment options in view of the functional status of the subject and his/her level of circulating OPN.

For example, an FG1 subject could be prescribed OPN or an OPN agonist. For FG1 subjects, brace treatment should generally be avoided. However, FG1 subjects having low levels of circulating OPN could under specific circumstances be prescribed brace treatment for a short period of time (e.g., about 6 months or until OPN concentration has been sufficiently increased i.e., at or near the retroinhibition concentration) so as to maintain his/her level of OPN high. Brace treatment could be stopped completely or temporarily when the maximal concentration of OPN is reached (i.e., near (but below) the retroinhibition concentration for a given patient e.g., for example between about 600 ng/ml and 1200 ng/ml, preferably between about 600 ng/ml and 1000 ng/ml. Generally, for FG1 subjects, preventive and treatment measures should aim at maintaining their level of OPN as high as possible.

For FG1 subjects already having high levels of OPN (i.e., close to the maximal OPN concentration where retroinhibition is induced), brace treatment should be avoided. If brace treatment is nevertheless prescribed, OPN levels and curve progression should be monitored closely so as to make sure that OPN levels do not drop significantly and that the rate or curve progression is not increased. OPN or an OPN agonist could also be prescribed to maintain OPN concentration high (as OPN has a protective effect in FG1 subjects as indicated above).

In general, any treatment or preventive measure which will help maintaining the level or activity of OPN as high as possible is desirable for FG1 subjects. In an embodiment, massages which increase OPN's level can be performed on a regular basis. For example, in U.S. Ser. No. 13/822,962 Applicants show that the local application of pressure (e.g., pulsative compressive pressure) on at least one body part of the subject (e.g., arm or leg) for 15-90 minutes increases circulating OPN blood level. Hence, such treatment could be applied to the subject periodically (e.g., every day, every two days, every 3 days, twice a week, once a week or once every two weeks) to increase or maintain the level of circulating OPN. Furthermore, as disclosed herein, HA increases (i.e., compensate in part) the Gi-mediated signaling defect present in FG1 subjects. Without being bound to any particular theory, HA could act by increasing OPN's bioavailability by competing with OPN for binding to CD44 (and thus act as an OPN agonist). By doing so, more OPN could be available for increasing the Gi-mediated cellular response.

Accordingly, one way of increasing the level or desired activity of OPN is by increasing the amount of Hyaluronic Acid (HA) in subjects. This can be done for example by taking HA supplements or by increasing HA intake or HA synthesis by favoring certain food. Non-limiting examples of food with high HA content or which stimulates/support HA production include, meat and meat organs (e.g., veal, lamb, beef and gizzards, livers, hearts and kidneys), fish, poultry (including meat fish and poultry broths), soy (including soy milk), root vegetables containing starch including potatoes and sweet potatoes, satoimo (Japanese sweet potato), imoji (Japanese sweet potato), Konyaku concoction (root vegetable concoction. Fruits and vegetables rich in vitamin C, magnesium or zinc are also useful as they support the synthesis of HA by the body. Non-limiting examples of food rich in vitamin C include lemons, oranges, limes, grapefruit, guava, mango, cherries, kiwi, blueberries, raspberries, all varieties of grapes, parsley, and thyme. Fruits and vegetables rich in magnesium include apples, bananas, tomatoes, avocados, pineapples, melons, peaches, pears, spinach, cauliflower, broccoli, asparagus, green lettuce, Brussels sprouts, and green beans. Non-limiting examples of food rich in zinc include pumpkins, yeast, peanuts, whole grains, beans, and brown rice.

Other possible treatments of preventive measures include the administration of agents which increase OPN expression or secretion (e.g., angiotensin, tumour necrosis factor α (TNFα), infterleukin-1β (IL-1β)), angiotensin II, transforming growth factor β (TGFβ) and parathyroid hormone (PTH)), low intensity pulsed ultrasounds (LIPUS), and treatment and preventive measure which decrease CD44 expression or binding to OPN (e.g., an antibody or siRNA specific for CD44/sCD44). Also, FG1 subjects should avoid diets rich in selenium since selenium is a powerful inhibitor of OPN or any other nutraceutical that decreases OPN level.

As indicated above, as opposed to the FG1 group, FG2 and FG3 subjects are particularly sensitive to OPN. High OPN levels in these subjects increase the risk of scoliosis development and progression. Generally, for FG2 and FG3 subjects, preventive and treatment measures should aim at maintaining their level of OPN as low as possible, especially since these subjects are sensitive to OPN (especially FG2 subjects, which are the most sensitive to OPN i.e., hypersensitive). Accordingly, any treatment or preventive measure which will help decreasing or maintaining the level or activity of OPN as low as possible is desirable for FG2 and FG3 subjects. Non-limiting examples of such treatment or preventive measure include, acupoint heat sensitive moxibustion, heat therapies with pad, thermal baths, electroacupuncture, which are known to decrease OPN in serum of subjects.

For FG2 and FG3 subjects, possible treatment and preventive measures also includes administration of an OPN antagonist to reduce OPN levels (administration of OPN antagonists (e.g., melatonin, selenium supplements or selenium from the diet (e.g., Brazil nuts), the use of nutraceutical like PROTANDIM) and/or brace treatment as it is likely to be beneficial to these subjects, especially to FG3 subjects. In FG2 and FG3 subjects having low levels of OPN, brace treatment could be postponed or not prescribed at all depending on the skeletal maturity, age and sex of the subject but if prescribed, it will be for preferably be at least 12-18 months, more preferably 24-36 months and even more preferably for 36 months or more, or for a sufficient time to induce a significant reduction in OPN levels. In a specific embodiment brace treatment will last at least 12, 18, 24, 30 or 36 months.

Since HA exacerbates the effect of OPN, FG2 and FG3 subjects should avoid taking HA supplements and preferably avoid taking food with high HA content or which stimulates/support HA production (e.g., comply to a HA-poor or HA-low diet). Similarly, any compound (synthetic or natural) or activity which are known to increase the level of OPN, or HA should preferably be avoided (e.g., angiotensin, tumour necrosis factor α (TNFα), infterleukin-1β (IL-1β)), angiotensin II, transforming growth factor β (TGFβ) and parathyroid hormone (PTH, regular application of compressive pressure (e.g., pulsative compressive pressure), LIPUS, etc.).

As disclosed herein, CD44 inhibition further decreases the Gi-mediated cellular response in FG2 and FG3 subjects. Accordingly, FG2 and FG3 subjects could also be treated with soluble CD44 or any compound which will increase its level. Furthermore, as the effect of OPN on the Gi-mediated response is dependent on the binding of OPN to integrins (e.g., $\alpha5\beta1$), molecules that specifically block the binding of OPN to integrins are also considered useful. For example, one known molecule that specifically blocks the binding of OPN to integrin (e.g., $\alpha_5\beta_1$) is a RGD peptide or derivative thereof. Other useful molecules include a peptide fragment of OPN comprising a RGD motif (e.g., GRGDSVVYGLRS (SEQ ID NO: 13); an siRNA specific for an integrin (e.g., $\alpha_5$, $\beta_1$, $\beta_3$, or $\beta_5$) or an antibody against an integrin (e.g., as, $\alpha_5$, $\beta_1$, $\beta_3$, and/or $\beta_5$ and/or volociximab™; etaratuzumab™, etaracizzumab™, Vitaxin™, MEDI-522 or CNT095).

Preferably, the level of OPN in the subject should be monitored periodically (e.g., every 6 months, every 5 months, every 4 months, preferably every 2 or 3 months, even more preferably every month) prior to and during any form of treatment or preventive measures and the frequency of OPN level monitoring increased when the level approaches retroinhibition concentration (e.g., 580-1000 ng/ml of OPN) in order to adapt treatment. For Example, for FG1 subjects having low levels of OPN, brace treatment could be performed, stopped when the level of OPN approaches retroinhibition concentration and restarted later (e.g., 6-18 months later) so as to induce another surge in OPN level. This cycle could be repeated as necessary.

The present invention also provides a method of predicting the risk of developing IS in a subject comprising: a) classifying the subject into functional group FG1, FG2 or FG3; and b) determining the level of circulating OPN in a blood sample from the subject, wherein when the subject is classified into the FG1 functional group and the level of circulating OPN in the blood sample of the subject is low, the subject has an increased risk of curve progression (as compared to FG1 subjects having high circulating level of OPN); and wherein when the subject is classified into the FG2 or FG3 functional group and the level of circulating OPN in the blood sample of the subject is high, the subject has an increased risk of curve progression (as compared to FG2 or FG3 subjects having low circulating level of OPN).

The present invention also provides kits for predicting the risk of developing scoliosis, for predicting brace treatment outcome and for selecting the best treatment or preventive measures. Such kits may comprise one or more reagents for classifying subjects into functional group FG1, FG2, or FG3 such as (a) one or more ligands (e.g., agonists) for stimulating GiPCRs; (b) ligands (e.g., antibodies) for detecting Giα proteins (Giα1, Giα2 and Giα3) and their phosphorylation pattern (e.g., antibodies for detecting serine phosphorylation); and/or (c) reagents for determining cellular proliferation; and optionally (d) (i) one or more ligands for stimulating GsPCRs (e.g., agonists) and (ii) instructions for using the kit. The kit may further comprise reagents for determining the level of circulating OPN in a blood sample such as primary antibodies (labeled or not) against OPN and optionally secondary antibodies to detect the binding of primary antibodies.

Definitions

For clarity, definitions of the following terms in the context of the present invention are provided.

Methods of classifying subjects into a functional group (FG1, FG2 or FG3) according to the degree of their imbalance in Gi-mediated cellular signaling are known in the art and have been described previously (see for example, Moreau at al. (2004), Akoume et al., (2010), Akoume et al., (2013), Azeddine et al., 2007; Letellier et al., 2008; WO2003/073102, WO2010/040234, International Publication No. WO2014/201557, and International Publication No. WO2015/032005 to Moreau, which are incorporated herein by reference in their entirety). Hence, in accordance with the present invention, any method or combination of methods of classifying a subject into the FG1, FG2 or FG3 group can be used. Non-limiting examples of classifying subjects following Gi-stimulation include i) detection of changes in cAMP concentration (Moreau et al., 2004), ii) change in cellular impedance (e.g., by cellular dielectric spectroscopy (CDS), Akoume et al., 2010 and Akoume et al., 2013b), detection of Gi phosphorylation pattern (Akoume et al. 2013), and cellular proliferation rate (WO03073102 and U.S. application No. 61/875,162). Classification may also be effected by determining the degree of imbalance between Gi and Gs as described in Akoume et al., 2013; Akoume et al., 2013b; and International Publication No. WO2015/032005).

As used herein, the terms "brace treatment outcome" refers to a genetic or metabolic predisposition of a subject to benefit or not from brace treatment. Non-limiting examples of brace treatment outcome includes: i) a final Cobb angle ≤5 to 45°; ii) a final Cobb angle to 45 (severe scoliosis); iii) curve progression; iv) absence of curve progression; and v) need for surgery or any other benefit that may be measured following brace treatment. A curve progression is defined as a progression of Cobb's angle ≥ to 6°.

A "successful brace treatment" or "brace treatment success" is a brace treatment following which the Cobb's angle is ≤ to 45° or no surgery is required.

As used herein, the term "benefit" in for example, "benefit from brace treatment" means that brace treatment has a positive effect on the prevention and/or treatment of IS. For example, a "benefit" of brace treatment can be one or more of: i) a reduction in the speed of curve progression; ii) a complete prevention of curve progression (i.e., a curve progression ≤6°; ii) a reduction of Cobb's angle in a pre-existing spinal deformity; iii) improvement of column mobility; iv) preservation/maintenance of column mobility; v) improvement of equilibrium and balance in a specific plan; vi) maintenance/preservation of equilibrium and balance in a specific plan; vii) improvement of functionality in a specific plan; viii) preservation/maintenance of functionality in a specific plan; ix) cosmetic improvement; x) avoidance of corrective surgery; and xi) combination of at least two of any of i) to x).

As used herein, the term "likely" in for example, "likely to have a successful brace treatment" refers to an increased chance of having a Cobb's angle ≤ to 45° or of not requiring surgery as compared to IS subjects in general, following brace treatment. In an embodiment, the increased chance of having successful brace treatment refers to a 50% chance or more (e.g., 60%, 65%, 70%, 75%, 80%, 85% . . . etc.) of having a Cobb's angle ≤ to 45° or of not requiring surgery following brace treatment. Similarly, the term "unlikely" (or less likely) in for example "unlikely to have a successful brace treatment" refers to a decreased chance of having a Cobb's angle ≤ to 45° or of not requiring surgery as compared to IS subjects in general, following brace treatment. In an embodiment, the decreased chance of having successful brace treatment refers to less than 50% chance (e.g., 49%, 45% 40%, 35%, 30%, 25%, 20% . . . etc.) of having a Cobb's angle ≤ to 45° or of not requiring surgery following brace treatment.

As used herein the term "subject" is meant to refer to any mammal including human, mouse, rat, dog, chicken, cat, pig, monkey, horse, etc. In a particular embodiment, it refers to a human. In a specific embodiment, the subject is a pediatric subject. In an embodiment, the subject is skeletally immature.

As used herein, the terms "subject in need thereof" refer to a subject already diagnosed with IS or at risk of developing IS (i.e., a likely candidate for developing scoliosis). In an embodiment, the subject in need thereof is a subject already diagnosed with idiopathic scoliosis. In an embodiment, the subject in need thereof is an asymptomatic subject having at least one family member having been diagnosed with idiopathic scoliosis. In an embodiment, the subject in need thereof is a pediatric subject.

In an embodiment, the above-mentioned subject is a likely candidate for developing a scoliosis, such as idiopathic scoliosis (e.g., Infantile Idiopathic Scoliosis, Juvenile Idiopathic Scoliosis or Adolescent Idiopathic Scoliosis (AIS)). As used herein the terms "likely candidate for developing scoliosis" include subjects (e.g., children) of which at least one parent has a scoliosis (e.g., adolescent idiopathic scoliosis). Among other factors, age (adolescence), gender and other family antecedent are factors that are known to contribute to the risk of developing a scoliosis and are used to a certain degree to assess the risk of developing a scoliosis. In certain subjects, scoliosis develops rapidly over a short period of time to the point of requiring a corrective surgery (often when the deformity reaches a Cobb's angle ≥50°. Current courses of action available from the moment a scoliosis such as AIS is diagnosed (when scoliosis is apparent) include observation (when Cobb's angle is around)10-25°, orthopedic devices (when Cobb's angle is around)25-30°, and surgery (over)45°. A more reliable determination of the risk of progression could enable to 1) select an appropriate diet to remove certain food products identified as contributors to scoliosis; 2) select the best therapeutic agent; and/or 3) select the least invasive available treatment such as postural exercises, orthopedic device, or less invasive surgeries or surgeries without fusions (a surgery that does not fuse vertebra and preserves column mobility). The present invention encompasses selecting the most efficient and least invasive known preventive actions or treatments in view of the determined risk of developing scoliosis.

As used herein, the terms "severe scoliosis", "severe IS" or "severe progression" is an increase of the Cobb's angle to 45° or more, potentially at a younger age.

As used herein the term "treating" or "treatment" in reference to idiopathic scoliosis (e.g., Infantile Idiopathic scoliosis (0-2 years old at the time of onset), Juvenile Idiopathic scoliosis (from 4 to 9 years old at the time of onset) and Adolescent Idiopathic scoliosis (from 10 to 17 years old at the time of onset) is meant to refer to e.g., at least one of a reduction of Cobb's angle in a preexisting spinal deformity, improvement of column mobility, preservation/maintenance of column mobility, improvement of equilibrium and balance in a specific plan; maintenance/preservation of equilibrium and balance in a specific plan; improvement of functionality in a specific plan, preservation/maintenance of functionality in a specific plan, cosmetic improvement, and combination of at least two of any of the above.

As used herein the term "preventing" or "prevention" in reference to scoliosis is meant to refer to a at least one of a reduction in the progression of a Cobb's angle in a patient having a scoliosis, a reduction in the speed of curve progression; or, in an asymptomatic patient, a complete prevention of apparition of a spinal deformity, including changes affecting the rib cage and pelvis in 3D, or a combination of any of the above.

As used herein the terms "at risk of developing a scoliosis" or "at risk of developing IS" refer to a genetic or metabolic predisposition of a subject to develop a scoliosis (i.e., spinal deformity) and/or a more severe scoliosis at a future time (i.e., curve progression of the spine). For instance, an increase of the Cobb's angle of a subject (e.g., from 40° to 50° or from 18° to 25°) is a "development" of a scoliosis. The terminology "a subject at risk of developing a scoliosis" includes asymptomatic subjects which are more likely than the general population to suffer in a future time of a scoliosis such as subjects (e.g., children) having at least one parent, sibling, or family member suffering from a scoliosis. Among others, age (adolescence), gender and other family antecedent are factors that are known to contribute to the risk of developing a scoliosis and are used to evaluate the risk of developing a scoliosis. Also included in the terminology "a subject at risk of developing a scoliosis" are subjects already diagnosed with IS but which are at risk to develop a more severe scoliosis (i.e., curve progression).

As used herein, a "low" level of OPN (e.g., Gene ID 6696, NP_001035147.1 (SEQ ID NO: 1) and NM_001040058 (SEQ ID NO: 2) SPP1-Gene ID: 6696, OPNa: NP_001035147.1, OPNb: NP_000573.1, OPNc: NP_001035149.1, OPN Isoform 4: NP_001238758.1, OPN Isoform 5: NP_001238759.1, NM_001251829.1, GI_352962173); is a level of OPN that is lower than the average level of OPN in IS (e.g., AIS) subjects. In an embodiment, the IS subjects are matched for age and/or sex. In another embodiment, the IS subjects are matched to a specific functional group (FG1, FG2 or FG3). In a specific embodiment, a low level of OPN is a level of OPN <than about 600 ng/ml, 580 ng/ml; 575 ng/ml, 560 ng/ml, 550 ng/ml, 520 ng/ml, 500 ng/ml, 450 ng ml, 400 ng/ml or 300 ng/ml. In specific embodiment, a low level of OPN is a level of OPN <600 ng/ml in a blood sample from the subject. In another specific embodiment, a low level of OPN is a level of OPN ≤500 ng/ml in a blood sample from the subject. In another specific embodiment, a low level of OPN is a level of OPN ≤250 ng/ml in a blood sample from the subject. In another specific embodiment, a low level of OPN is a level of OPN that is about that of healthy subjects. In a specific embodiment, for FG2 subjects (which are hypersensitive to OPN), in the context of the treatment method of the present invention, the level of OPN is maintained as low as possible, preferably below 400 ng/ml, more preferably below 300 ng/ml and even more preferably below 200 ng/ml.

As used herein, a "high" level of OPN (e.g., Gene ID 6696, NP_001035147.1 (SEQ ID NO: 1) and NM_001040058 (SEQ ID NO: 2) is a level of OPN that is higher than the average level of OPN in IS (e.g., AIS) subjects. In an embodiment, the IS subjects are matched for age and/or sex. In another embodiment, the IS subjects are matched to a specific functional group (FG1, FG2 or FG3). In a specific embodiment, a high level of OPN is a level of OPN than about 1200 ng/ml, 1000 ng/ml, 900, ng/ml, 850 ng/ml, 800 ng/ml, 750 ng/ml, 700 ng/ml, 550 ng/ml, 580 ng/ml, 600 ng/ml; 610 ng/ml, 620 ng/ml, 630 ng/ml, 650 ng/ml, 675 ng/ml, 700 ng/ml or 750 ng/ml. In a specific embodiment, a high level of OPN is a level of OPN between about 650-1000 ng/ml in a blood sample from the subject. In another specific embodiment, a high level of OPN is a level of OPN 600 ng/ml in a blood sample from the subject. In another embodiment, a high level of OPN is a level of OPN that is close to but below the retroinhibition concentration (e.g., 80%, 85%, 90%, 95% of the retroinhibition concentration). In another specific embodiment, for FG1 subjects, in the context of the treatment method of the present invention, the level of OPN is maintained as high as possible, preferably above 500 ng/ml, above 800 ng/ml or above 900 ng/ml and even more preferably above 1000 ng/ml or above 1200 ng/ml.

As used herein, the term "retroinhibition concentration" refers to the in vivo concentration at which OPN level reaches its maximum and the retroinhibition mechanism is induced so as to decrease the level of circulating OPN in the blood endogenously.

As used herein, the term "retroactivation concentration" refers to the in vivo concentration at which OPN level reaches its minimum and the retroactivation mechanism is induced so as to increase the level of circulating OPN in the blood endogenously. In a specific embodiment, it refers the concentrations of OPN at which brace treatment first induces an increase in OPN level. In an embodiment, the retroactivation concentration is 600 ng/ml or less, preferably 500 ng/ml or less and even more preferably, 400 ng/ml or less.

As used herein the terms "follow-up schedule" is meant to refer to future medical visits a subject diagnosed with a scoliosis or at risk of developing a scoliosis is prescribed once the diagnosis or risk evaluation is made. For example, when a subject is identified as belonging to the FG1 functional group and as having a low level of OPN (and the subject is prescribed OPN, an OPN agonist or treatment and preventive measures which increase OPN levels), the number of medical visits is increased to make sure that OPN levels are stable, preferably increase and remain as high as possible. In addition, in the rare case where an FG1 subject is prescribed a brace treatment, the number of medical visits is increased to make sure that brace treatment lasts for an optimal time and the level of OPN does not decrease. For example, OPN levels could be monitored every 2 months, preferably every month and the treatment adjusted in view of the detected OPN level. For example, when OPN level reached or approached retroinhibition concentration treatment would be stopped completely or temporarily until OPN level decrease sufficiently and the treatment could be started again. In addition, or alternatively, curve progression could be monitored, and the treatment maintained until curve progression is detected. Another limiting example include when a subject being at risk of developing a severe scoliosis or at risk of rapid curve progression (e.g., a subject classified as belonging to the FG2 functional group and having a high level or circulating OPN), the number of medical visits (e.g., to the orthopedist) is increased, the frequency of OPN monitoring is increased and/or the number of x-rays in a given period (e.g., 1, 2, 3, 6 or 12 months) is increased. On the other hand, when a subject is identified as having a lower risk of curve progression or rapid curve progression (e.g., subject being classified as belonging to the FG1 functional group and having high levels of OPN) the number of medical visits, OPN level monitoring or x-rays may be decreased to less than the average (e.g., less than 22 x-rays over a 3-year period or less than 1 visit every month, every 3 months, 6 months, or 12 months). The follow-up schedule and OPN monitoring frequency is adapted in view of several factor including sex, age, Cobb's angle, skeletal maturity (Risser of 5), menarche, functional classification (FG1, FG2 or FG3) and OPN level.

As used herein, the term "brace treatment" refers to the use of a brace for reducing (i.e., slowing or stopping) curve progression of the scoliosis or for improving scoliosis (i.e., reversing completely or partially the scoliosis, e.g., a reduction of a Cobb's angle from 30 to)24°. There are a number of bracing options known in the art. Non-limiting examples of braces used in the treatment of scoliosis include the Thrombo-Lumbar-Sacral Orthosis (TLSO) brace, the Milwaukee brace, the Charleston brace and the SpineCor™ brace. Other examples include the Dynamic scoliosis orthosis brace (DSO) (U.S. Pat. No. 7,967,767); scoliosis braces with angle adjustment (U.S. Pat. No. 8,066,653) and braces with adjustable inflatable air bags (US2009/0275871). The physician will recommend a particular back brace and bracing schedule based on factors such as the location of the curve, degree of curvature (Cobb's angle), age, growth status of the IS subject (e.g., pre- or post-menarche, and skeletal maturity (Risser of 5), endophenotype (IS functional group) and lifestyle (e.g., for subjects involved in sports, a more flexible brace (e.g., SpineCor™ or Charleston may be favored). Moreover, a combination of braces may also be prescribed (e.g., a TLSO brace for daytime and a Charleston brace for night time).

The most common form of TLSO brace is called the "Boston brace", and it may be referred to as an "underarm" brace. This brace is fitted to the child's body and custom molded from plastic. It works by applying three-point pressure to the curvature to prevent its progression. The TLSO brace is usually worn 23 hours/day, and it can be taken off to swim, play sports or participate in gym class during the day. This type of brace is usually prescribed for curves in the lumbar or thoraco-lumbar part of the spine.

The Cervico-Thoraco-Lumbo-Scacral-Orthosis brace (Milwaukee brace) is similar to the TLSO described above, but also includes a neck ring held in place by vertical bars attached to the body of the brace. It is usually worn 23 hours a day, and can be taken off to swim, play sports or participate in gym class during the day. This type of brace is often prescribed for curves in the Thoracic spine.

The Charleston brace, also called nighttime brace is a back brace which is molded to the patient while they are bent to the side, and thus applies more pressure and bends the child against the curve. This pressure improves the corrective action of the brace. This type of brace is worn only at night while the child is asleep. Curves must be in the 20- to 40-degree range and the apex of the curve needs to be below the level of the shoulder blade for the Charleston brace to be effective.

In accordance with the present invention, the skilled practitioner (e.g., the treating physician) can select the most appropriate treatment regimen based on the subject's classification. The particular choice of treatment or combination of treatment will be adapted based on the subject's classification and optionally based on his/her level of circulating OPN. For example, brace treatment may be delayed, shortened/lengthened, the choice of a particular brace or braces adapted (in view of age, sex, and Cobb's angle) and the time at which surgery is performed (if needed) modified in view of the subject's classification and optionally, circulating OPN level.

In the context of treating FG1 subjects with a brace, a "short" brace treatment or "short term" brace treatment includes brace treatment for 18 months or less, preferably 12 months or less and more preferably, 6 months or less (e.g., 1, 2, 3, 4, 5 or 6 months). Preferably, if brace treatment is prescribed for FG1 subjects, the brace treatment may be continued until the OPN concentration reaches its maximal concentration or close to its maximal concentration (retroinhibition concentration). In an embodiment, brace treatment will be continued until OPN concentration starts declining in the subject. In a specific embodiment, brace treatment is continued until OPN concentration reaches 700, 800, 1000, 1100 or 1200 or more ng/ml.

In the context of treating FG2 and FG3 subjects with a brace, a "long" brace treatment or "long-term" brace treatment includes brace treatment for at least 18 months (e.g., 18, 19, 20, 21, 22, 23 months), preferably at least 24 months (e.g., 24, 25, 26, 27, 28, 29, 30, 31, 32, 33, 34, 35 months) and more preferably, at least 36 months. Preferably, for FG2 and FG3 subjects brace treatment will be continued until OPN concentration is significantly reduced or until skeletal maturity is reached. In a specific embodiment, brace treatment is maintained until the OPN concentration reaches its minimum or until the OPN concentration begins increasing.

In a specific embodiment, brace treatment is maintained up to two years after menarche in a female subject. In a particular embodiment, brace treatment is maintained until the concentration of OPN reaches less than 600 ng/ml, preferably less than 500 ng/ml or until the OPN concentration reaches its minimum or starts increasing. In a particular embodiment for FG3 subjects, brace treatment is maintained until the concentration of OPN reaches less than 600 ng/ml, preferably less than 500 ng/ml. In another particular embodiment, for FG2 subjects brace treatment is maintained until the concentration of OPN reaches less than 400 ng/ml, preferably less than 300 ng/ml more preferably less than 200 ng/ml (due to their hypersensitivity toward OPN).

The terms "activator" or "agonist" are well known in the art and are used herein interchangeably. Similarly, the terms "suppressor", "inhibitor" and "antagonist" are well known in the art and are used herein interchangeably As used herein, the expression "OPN agonist" or "OPN activator" is used to refer to any compound capable to increase, at least partially, the level and/or desired biological activity of OPN (e.g., Gene ID 6696, NP_001035147.1 (SEQ ID NO: 1) and NM_001040058 (SEQ ID NO: 2) SPP1-Gene ID: 6696, OPNa: NP_001035147.1, OPNb: NP_000573.1, OPNc: NP_001035149.1, OPN Isoform 4: NP_001238758.1, OPN Isoform 5: NP_001238759.1, NM_001251829.1, GI_352962173). Without being so limited it includes OPN functional fragment or derivative thereof and activators of OPN expression such as (but not limited to) transcriptional and translational activators of the OPN gene (e.g., tumour necrosis factor α (TNFα), infterleukin-1β (IL-1β)), angiotensin II (Ang II), transforming growth factor β (TGFβ) and parathyroid hormone (PTH)). Activator of OPN activity includes compounds that are able to bind to OPN receptors in order to increase the desired biological activity of OPN, peptidomimetics, OPN fragments and the like. In a specific embodiment, the OPN biological activity is an increase in Gi-mediated cellular response in FG1 subjects and the OPN activator or agonist is HA.

As used herein, the term "functional fragment" of OPN refers to a molecule (e.g., polypeptide) which retains substantially the same desired activity as the original molecule, but which differs by any modifications, and/or amino acid/nucleotide substitutions, deletions, or additions (e.g., fusion with another polypeptide). Modifications can occur anywhere including the polypeptide/polynucleotide backbone (e.g., the amino acid sequence, the amino acid side chains and the amino or carboxy termini). Such substitutions, deletions or additions may involve one or more amino acids or in the case of polynucleotide, one or more nucleotide. The substitutions are preferably conservative, i.e., an amino acid is replaced by another amino acid having similar physicochemical properties (size, hydrophobicity, charge/polarity, etc.) as well known by those of ordinary skill in the art. Functional fragments of OPN (SEQ ID NO: 1) include a fragment or a portion of OPN polypeptide or a fragment or a portion of a homologue or allelic variant of OPN which retains activity, i.e., binds to integrins (e.g., α5β1) and/or CD44. In an embodiment, the OPN functional fragment is at least 80, 85, 88, 90, 95, 98 or 99% identical to the polypeptide sequence of (SEQ ID NO: 1). In an embodiment, the OPN functional fragment is a functional variant which includes variations in amino acids which are not conserved between rat, mouse and human OPN. Preferably, the OPN functional fragment is human. A "functional derivative" refers to a molecule derived from the OPN polypeptide or polynucleotide and which is substantially similar in structure and biological activity to the OPN protein or nucleic acid of the present invention. An OPN polypeptide derivative may for example include modifications to increase its bioavailability, its stability, to simplify its purification or to preferentially target the OPN derivative to a particular tissue or cell.

As used herein, the expression "OPN antagonist" or "OPN inhibitor" is used to refer to any compound capable to block completely or partially (i.e., negatively affect) the expression (at the transcriptional (mRNA) and/or translational (protein)) level or targeted biological activity of OPN (e.g., binding to one or more of its integrin receptors) in cells. In an embodiment, the biological activity of OPN in cells is a reduction in GiPCR signaling. OPN inhibitors include intracellular as well as extracellular suppressors. Without being so limited, such suppressors include RNA interference agents (siRNA, shRNA, miRNA), antisense molecules, ribozymes, proteins (e.g., dominant negative, inactive variants), peptides, small molecules, antibodies, antibody fragments, etc. In an embodiment, the OPN antagonist is a neutralizing antibody against human OPN. In an embodiment, the OPN antagonist is melatonin. In an embodiment, the OPN antagonist is selenium. In an embodiment, the OPN antagonist is PROTANDIM™. In an embodiment, the OPN antagonist is soluble CD44 (sCD44) or a stimulator or enhancer of sCD44/CD44 expression.

As used herein, the expression "integrin antagonist" or "integrin inhibitor" is used to refer to any compound capable to block completely or partially (i.e., negatively affect) the expression (at the transcriptional (mRNA) and/or translational (protein)) level or targeted biological activity of integrins (e.g., binding to OPN) in cells. In an embodiment, the biological activity of integrins in cells is a reduction in GiPCR signaling. Integrin inhibitors include intracellular as well as extracellular suppressors. Without being so limited, such suppressors include RNA interference agents (siRNA, shRNA, miRNA), antisense molecules, ribozymes, proteins (e.g., dominant negative, inactive variants), peptides, small molecules, antibodies, antibody fragments, etc. In an embodiment, the integrin antagonist is a neutralizing antibody against human integrin (voloximab™; etaratuzumab™, etaracizzumab™, Vitaxin™, MEDI-522, CNT095, cilengitide™).

The terms "inhibitor of OPN expression" or "inhibitor of integrin expression" (e.g., $\alpha_5$, $\beta_1$, $\beta_3$, and/or $\beta_5$) expression" include any compound able to negatively affect OPN's or integrin's (e.g., $\alpha_5$'s, $\beta_1$'s, $\beta_3$'s, and/or $\beta_5$'s) expression (i.e., at the transcriptional and/or translational level), i.e. the level of OPN/integrin mRNA and/or protein or the stability of the protein. Without being so limited, such inhibitors include agents which negatively affect the expression of OPN (e.g., vitamin D, melatonin, selenium, PROTANDIM™) or integrin, RNA interference agents (siRNA, shRNA, miRNA), antisense molecules, and ribozymes. Such RNA interference agents are design to specifically hybridize with their target nucleic acid under suitable conditions and are thus substantially complementary their target nucleic acid.

The terms "inhibitor of OPN activity" or "inhibitor of integrin activity" (e.g., (e.g., $\alpha_5$, $\beta_1$, $\beta_3$, and/or $\beta_5$) refers to any molecules that is able to reduce or block the effect of OPN or integrins (e.g., 531) on Gi-mediated signaling. These molecules increase GiPCR signaling in cells (i.e., in FG2 and FG3 subjects) by blocking/reducing totally or partially the inhibitory effect induced by OPN and/or integrins activity. Non-limiting examples of inhibitors of OPN's activity include proteins (e.g., dominant negative, inactive variants), peptides, small molecules, anti-OPN antibodies (neutralizing antibodies), antibody fragments, inactive fragments of α5 and/or β1 integrins etc. Non-limiting examples of inhibitors of integrin (e.g., α5β1) activity include proteins (e.g., dominant negative, inactive variants), peptides (RGD peptides or RGD peptide-derivatives), small molecules, anti $\alpha_5$ and/or $\beta_1$ antibodies (e.g., neutralizing antibodies such as Volociximab™ M200, etaratuzumab™, etaracizzumab™, Vitaxin™, MEDI-522, CNT095, cilengitide™), antibody fragments, etc. In an embodiment, the RGD peptide is a peptide fragment of OPN comprising a RGD motif comprising the amino acid sequence GRGDSVVYGLRS corresponding to amino acid 158 to 169 of OPN (SEQ ID NO: 1). In an embodiment, the OPN fragment comprising the RGD motif comprises amino acids 158 to 162, 158 to 165, 158 to 167, 158 to 170, 158 to 175, 158 to 180, 158 to 185, 158 to 190, 158 to 195, or 158 to 200 of OPN (e.g., SEQ ID NO: 1). In an embodiment, peptide fragment of OPN comprising a RGD motif comprises amino acids 158 to 161, 156 to 161, 154 to 161, 152 to 162, 150 to 162, 148 to 162, 146 to 162, 144 to 162, 140 to 162, 159 to 163, 159 to 164, 159 to 162, 159 to 166, 159 to 167, or 159 to 169 of OPN (e.g., SEQ ID NO: 1).

In an embodiment, the "inhibitor of OPN's activity" is a neutralizing antibody directed against (or specifically binding to) a human OPN polypeptide which inhibits its binding to integrins such as $\alpha_5\beta_1$ (i.e., binding to $\alpha_5$ and/or $\beta_1$ integrin) In an embodiment, the "inhibitor of integrin activity" is a neutralizing antibody directed against (or specifically binding to) a human integrin ($\alpha_5$, $\beta_1$, $\beta_3$, and/or $\beta_5$) polypeptide which inhibits the binding of OPN to integrins (i.e., binding to $\alpha_5$, $\beta_1$, $\beta_3$, and/or $\beta_5$ integrin). In an embodiment, the antibody binds to the RGD domain of OPN. In an embodiment, the antibody is directed against amino acids 159 to 162, 158 to 162, 158 to 165, 158 to 167, 158 to 170, 158 to 175, 158 to 180, 158 to 185, 158 to 190, 158 to 195, or 158 to 200 of OPN (e.g., SEQ ID NO: 1). In an embodiment, the antibody is directed against amino acids 158 to 161, 156 to 161, 154 to 161, 152 to 162, 150 to 162, 148 to 162, 146 to 162, 144 to 162, 140 to 162, 159 to 163, 159 to 164, 159 to 162, 159 to 166, 159 to 167, or 159 to 169 of OPN (e.g., SEQ ID NO: 1).

Similarly, the terms "inhibitor of integrin's activity", "inhibitor of $\alpha_5\beta_1$'s activity", "inhibitor of Q5's activity" or "inhibitor of $\beta_1$'s activity", "inhibitor of $\beta_3$'s activity", "inhibitor of $\beta_5$'s activity" and the like include any compound able to negatively affect the expression and/or activity of $\alpha_5$ (e.g., Gene ID 3678, NP_002196.2 (SEQ ID NO: 5) and NM_002205.2 (SEQ ID NO: 6)), $\beta_1$ (Gene ID 3688, NP_002202.2 (SEQ ID NO: 7) and NM_002211.3 (SEQ ID NO: 8)), $\beta_3$ (Gene ID 3690, NP_000203.2 (SEQ ID NO: 9) and NM_000212 (SEQ ID NO: 10) and/or $\beta_5$ (Gene ID 3693, NP_002204.2 (SEQ ID NO: 11) and NM_002213.3 (SEQ ID NO: 12)) in cells. In a particular embodiment, the "activity" of $\alpha_5$ and/or $\beta_1$ in cells is the transduction of the signal leading to the OPN-dependent inhibition of GiPCR signaling. In a particular embodiment, the inhibitor is Volociximab™ M200, etaratuzumab™, etaracizzumab™, Vitaxin™, MEDI-522, CNT095 or cilengitide™.

The term "inhibitor" of sCD44/CD44 expression (e.g., Gene ID 960, NP_000601.3, (SEQ ID NO: 3), NM_000610 (SEQ ID NO: 4)) refers to an agent able to decrease the level of expression of CD44 and an agent able to decrease CD44 secretion. In an embodiment, the inhibitor of sCD44/CD44 is an agent able to decrease CD44 binding with OPN. Without being so limited, the agent can be a protein (e.g., an antibody specific to CD44), a peptide, a small molecule, or a nucleotide. Inhibitors of sCD44 or CD44 generally increase OPN's bioavailability for other receptor of OPN (e.g., integrins) and may be particularly useful for treating and preventing scoliosis development in FG1 subjects.

The term "stimulator" or "enhancer" of sCD44/CD44 expression (e.g., Gene ID 960, NP_000601.3, (SEQ ID NO: 3), NM_000610 (SEQ ID NO: 4)) refers to an agent able to increase the level or expression of CD44 and an agent able to increase CD44 secretion. In an embodiment, the stimulator of sCD44/CD44 is an agent able to increase CD44 affinity toward OPN. Without being so limited, the agent can be a protein, a peptide, a small molecule, or a nucleotide. "Stimulators" or "enhancers" of sCD44/CD44 expression generally decrease OPN's bioavailability for other receptor of OPN (e.g., integrins) and may be particularly useful for treating and preventing scoliosis development in FG2 and FG3 subjects.

Antibodies

In general, techniques for preparing antibodies (including monoclonal antibodies and hybridomas) and for detecting antigens using antibodies are well known in the art (Campbell, 2000, In "Monoclonal Antibody Technology: The production and characterization of Rodent and Human Hybridomas", Elsevier Science Publisher, Amsterdam, The Netherlands) and Recombinant Monoclonal Antibodies (Mariel Donzeau and Achim Knappik; Methods in Molecular Biology; Volume 378, 2007, pp 15-31).

As used herein, the term "anti-OPN antibody", refers to an antibody that specifically binds to (interacts with) OPN and displays no substantial binding to other naturally occurring proteins other than the ones sharing the same antigenic determinants as OPN. Similarly, the expression "anti-CD44 antibody", "anti-$\beta_1$ antibody" and the like (anti-$\alpha_5$, anti-$\beta_3$, anti-$\beta_5$ . . . ) refers to an antibody that specifically binds to (interacts with) CD44 or $\beta_1$ and displays no substantial binding to other naturally occurring proteins other than the ones sharing the same antigenic determinants as CD44/$\beta_1$, The term "antibody" or "immunoglobulin" is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full-length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention. In an embodiment, the antibody is a monoclonal antibody. In another embodiment, the antibody is a humanized or CDR-grafted antibody.

TABLE 1 commercially available human OPN Elisa kits.

| Company | Kit name | Catalogue number | Sensitivity |
|---|---|---|---|
| IBL Hambourg | Human Osteopontin ELISA | JP 171 58 | 3.33 ng/ml |
| IBL America | Human Osteopontin N-Half Assay Kit-IBL | 27258 | 3.90 pmol/L |
| IBL-America | Human Osteopontin Assay Kit-IBL | 27158 | 3.33 ng/ml |
| Assay designs | Osteopontin (human) EIA Kit | 900-142 | 0.11 ng/ml |
| American Research Products, Inc. | Osteopontin, human kit | 17158 | ? |
| R&D Systems | Human Osteopontin (OPN) ELISA Kit | DOST00 | 0.024 ng/mL |
| Promokine | Human Osteopontin ELISA | PK-EL-KA4231 | 3.6 ng/ml |
| Uscnlife | Human Osteopontin, OPN ELISA Kit | E0899h | ? |

TABLE 2

Non-limiting examples of commercially available antibodies for OPN (Human, Unconjugated)

| Company Name | Catalogue Number | Host |
|---|---|---|
| EMD Millipore | AB10910 | rabbit |
| Boster Immunoleader | PA1431 | |
| LifeSpan BioSciences | LS-C63082-100 | mouse |
| LifeSpan BioSciences | LS-B5940-50 | mouse |
| LifeSpan BioSciences | LS-C137501-100 | mouse |
| LifeSpan BioSciences | LS-C31763-100 | rabbit |
| LifeSpan BioSciences | LS-C99283-400 | rabbit |
| LifeSpan BioSciences | LS-C9410-100 | rabbit |
| LifeSpan BioSciences | LS-C122259-20 | rabbit |
| LifeSpan BioSciences | LS-C88774-0.1 | rabbit |
| LifeSpan BioSciences | LS-C136850-100 | rabbit |
| LifeSpan BioSciences | LS-C96393-500 | rabbit |
| LifeSpan BioSciences | LS-C193595-200 | mouse |
| LifeSpan BioSciences | LS-C193596-100 | mouse |
| LifeSpan BioSciences | LS-C63081-100 | mouse |
| LifeSpan BioSciences | LS-C193597-100 | mouse |
| LifeSpan BioSciences | LS-C169155-100 | mouse |
| LifeSpan BioSciences | LS-C189569-1000 | mouse |
| LifeSpan BioSciences | LS-C189635-1000 | mouse |
| LifeSpan BioSciences | LS-C189636-1000 | mouse |
| LifeSpan BioSciences | LS-C189634-1000 | mouse |
| LifeSpan BioSciences | LS-C73947-500 | mouse |
| LifeSpan BioSciences | LS-C189134-50 | rabbit |
| LifeSpan BioSciences | LS-B5272-250 | rabbit |
| LifeSpan BioSciences | LS-C176152-100 | rabbit |
| LifeSpan BioSciences | LS-C194024-100 | rabbit |
| LifeSpan BioSciences | LS-B5626-50 | rabbit |
| LifeSpan BioSciences | LS-C131159-20 | rabbit |
| LifeSpan BioSciences | LS-B9287-200 | rabbit |
| LifeSpan BioSciences | LS-C73949-200 | rabbit |
| LifeSpan BioSciences | LS-C182368-50 | rabbit |
| LifeSpan BioSciences | LS-B2411-50 | goat |
| LifeSpan BioSciences | LS-B8326-100 | mouse |
| LifeSpan BioSciences | LS-B7193-50 | rabbit |
| LifeSpan BioSciences | LS-B425-50 | rabbit |
| LifeSpan BioSciences | LS-C9413-100 | rabbit |
| LifeSpan BioSciences | LS-B7193-50 | rabbit |
| LifeSpan BioSciences | LS-C9413-100 | rabbit |
| LifeSpan BioSciences | LS-B9080-100 | rabbit |
| LifeSpan BioSciences | LS-C201116-100 | rabbit |
| Boster Immunoleader | PA1431 | |
| antibodies-online | ABIN933617 | mouse |
| antibodies-online | ABIN1381708 | Chicken |
| BACHEM | T-4816.0400 | Rabbit |
| BACHEM | T-4815.0050 | Rabbit |
| Biorbyt | orb12414 | mouse |
| Biorbyt | orb128774 | Rabbit |
| Biorbyt | orb12506 | mouse |
| Biorbyt | orb94522 | Rabbit |
| Biorbyt | orb13123 | Rabbit |
| Biorbyt | orb88187 | goat |
| Biorbyt | orb94961 | mouse |
| Biorbyt | orb86662 | rabbit |
| Biorbyt | orb170816 | mouse |
| Biorbyt | orb175965 | mouse |
| Biorbyt | orb19047 | goat |
| Biorbyt | orb43142 | rabbit |
| Biorbyt | orb120032 | rabbit |
| Biorbyt | orb11192 | rabbit |
| Biorbyt | orb11191 | rabbit |
| antibodies-online | ABIN933617 | mouse |
| BioVision | 5426-100 | mouse |
| BioVision | 5422-100 | mouse |
| BioVision | 5424-100 | mouse |
| BioVision | 5423-100 | mouse |
| BioVision | 5425-100 | mouse |
| BioVision | 5421-100 | mouse |
| Merck Millipore | 04-970 | mouse |

TABLE 2-continued

Non-limiting examples of commercially available antibodies for OPN (Human, Unconjugated)

| Company Name | Catalogue Number | Host |
|---|---|---|
| Merck Millipore | MAB3055 | rabbit |
| Merck Millipore | AB1870 | Rabbit |
| Merck Millipore | AB10910 | Rabbit |
| GenWay Biotech, Inc. | GWB-T00561 | mouse |
| GenWay Biotech, Inc. | GWB-T00557 | mouse |
| GenWay Biotech, Inc. | GWB-T00558 | mouse |
| GenWay Biotech, Inc. | GWB-T00559 | mouse |
| GenWay Biotech, Inc. | GWB-T00560 | mouse |
| GenWay Biotech, Inc. | GWB-3A2E99 | goat |
| GenWay Biotech, Inc. | GWB-23C38D | rabbit |
| GenWay Biotech, Inc. | GWB-295359 | Rabbit |
| GenWay Biotech, Inc. | GWB-806785 | Goat |
| Enzo Life Sciences, Inc. | ADI-905-629-100 | mouse |
| Enzo Life Sciences, Inc. | ADI-905-630-100 | mouse |
| Enzo Life Sciences, Inc. | ADI-905-500-1 | Rabbit |
| Enzo Life Sciences, Inc. | ALX-210-309-R100 | Rabbit |
| GeneTex | GTX28448 | Rabbit |
| GeneTex | GTX37500 | rabbit |
| GeneTex | GTX15489 | rabbit |
| GeneTex | GTX89519 | goat |
| Spring Bioscience | E3282 | rabbit |
| Spring Bioscience | E3280 | rabbit |
| Spring Bioscience | E3281 | rabbit |
| Spring Bioscience | E3284 | rabbit |
| Abbiotec | 251924 | rabbit |
| Abbiotec | 250801 | rabbit |
| MBL International | CY-P1035 | |
| Rockland Immunochemicals, Inc. | 100-401-404 | Rabbit |
| Bioss Inc. | bs-0026R | Rabbit |
| Bioss Inc. | bs-0019R | Rabbit |
| Proteintech Group Inc | 22952-1-AP | Rabbit |

TABLE 4

Non-limiting examples of commercially available ELISA Kits for integrin $\alpha_5$ (ITGA5, Human)

| Company Name | Catalogue number | Range | Sensitivity |
|---|---|---|---|
| antibodies-online | ABIN417612 | 0.156-10 ng/mL | 0.054 ng/mL |
| antibodies-online | ABIN365741 | na | na |
| DLdevelop | DL-ITGa5-Hu | 0.156-10 ng/mL | 0.054 ng/mL |
| MyBioSource.com | MBS814027 | na | na |
| R&D Systems | DYC3230-2 | 312-20,000 pg/mL | na |
| Biomatik | E91287Hu | 0.156-10 ng/mL | 0.054 ng/mL |

TABLE 5

Non-limiting examples of commercially available Antibodies for $\alpha_5$ (ITGA5, human)

| Company Name | Catalogue Number | Host |
|---|---|---|
| Novus Biologicals | NBP1-84576 | rabbit |
| Biorbyt | orb69201 | mouse |
| Abcam | ab72663 | rabbit |
| Acris Antibodies GmbH | BM4033 | mouse |
| Aviva Systems Biology | OAAF05375 | rabbit |
| St John's Laboratory | STJ32097 | mouse |
| GeneTex | GTX86915 | rabbit |

TABLE 5-continued

Non-limiting examples of commercially available Antibodies for $\alpha_5$ (ITGA5, human)

| Company Name | Catalogue Number | Host |
|---|---|---|
| GeneTex | GTX86905 | rabbit |
| OriGene Technologies | TA311966 | rabbit |
| OriGene Technologies | TA310024 | rat |
| Abbexa | abx15590 | rabbit |
| Abbexa | abx15591 | rabbit |
| Abbiotec | 252937 | mouse |
| Abnova Corporation | MAB10703 | mouse |
| Abnova Corporation | MAB5267 | mouse |
| Bioss Inc. | bs-0567R | rabbit |
| Cell Signaling Technology | 4705S | rabbit |
| Atlas Antibodies | HPA002642 | rabbit |
| GenWay Biotech, Inc. | GWB-MX190A | rabbit |
| GenWay Biotech, Inc. | GWB-D9743E | mouse |
| antibodies-online | ABIN656138 | rabbit |
| antibodies-online | ABIN219716 | rabbit |
| Novus Biologicals | NBP1-71421-0.1mg | rabbit |
| Novus Biologicals | NBP1-71421-0.05mg | rabbit |
| BioLegend | 328009 | mouse |
| BD Biosciences | 610634 | mouse |
| BioLegend | 328002 | mouse |
| BD Biosciences | 610634 | mouse |
| Abcam | ab72665 | rabbit |
| Abcam | ab55988 | rabbit |
| Bioworld Technology | BS7053 | rabbit |
| Santa Cruz Biotechnology, Inc. | sc-166665 | mouse |
| Bioworld Technology | BS7052 | rabbit |
| R&D Systems | AF1864 | goat |
| R&D Systems | FAB1864A | mouse |
| Thermo Scientific Pierce Antibodies | MA5-15568 | mouse |
| Thermo Scientific Pierce Antibodies | MA1-81134 | mouse |
| AbD Serotec (Bio-Rad) | MCA1187 | mouse |
| AbD Serotec (Bio-Rad) | MCA1187T | mouse |
| Life Technologies | 132600 | mouse |
| Proteintech Group Inc | 10569-1-AP | rabbit |
| Raybiotech, Inc. | 119-14178 | mouse |
| Creative Biomart | CAB-3671MH | mouse |
| Merck Millipore | CBL497 | mouse |
| Fitzgerald Industries International | 10R-1984 | mouse |
| EMD Millipore | AB1921 | rabbit |
| EMD Millipore | AB1949 | rabbit |

TABLE 6

Non-limiting examples of commercially available ELISA Kits for $\beta 1$ (ITGB1, human)

| Company Name | Catalogue number | Range | Sensitivity |
|---|---|---|---|
| antibodies-online | ABIN833710 | na | na |
| Merck Millipore | ECM470 | na | na |
| DLdevelop | DL-ITGb1-Hu | 1.56-100 ng/mL | na |
| Biomatik | E91042Hu | 1.56-100 ng/mL | 0.64 ng/mL |

TABLE 7

Non-limiting examples of commercially available antibodies for $\beta_1$ ITGB1 (Human, Unconjugated)

| Company Name | Catalogue number | Host |
|---|---|---|
| Abgent | AM2241b | mouse |
| Biorbyt | orb86390 | rabbit |
| LifeSpan BioSciences | LS-C84969-100 | mouse |
| Novus Biologicals | NB110-55545 | rabbit |
| Abbexa | abx12778 | rabbit |
| Bethyl Laboratories, Inc. | A303-735A | rabbit |
| Abcam | ab5189 | Rabbit |

TABLE 7-continued

Non-limiting examples of commercially available antibodies for β₁ ITGB1 (Human, Unconjugated)

| Company Name | Catalogue number | Host |
|---|---|---|
| St John's Laboratory | STJ60344 | Rabbit |
| Cell Signaling Technology | 4706S | Rabbit |
| Bioss Inc. | bs-0486R | Rabbit |
| Antigenix America Inc. | MA290020 | Rabbit |
| GenWay Biotech, Inc. | GWB-312F4D | mouse |
| Fitzgerald Industries International | 20R-2722 | rabbit |
| GeneTex | GTX50784 | rabbit |
| Thermo Scientific Pierce Antibodies | MA1-80764 | mouse |
| R&D Systems | AF1778 | goat |
| Abbiotec | 251162 | rabbit |
| Bioworld Technology | BS1817 | rabbit |
| Abgent | AM2241b | mouse |
| Enzo Life Sciences, Inc. | BML-IG6060-0100 | mouse |
| BIOCARE MEDICAL | CME 386 A | rabbit |
| ProSci, Inc | 48-392 | Rabbit |
| eBioscience | 14-0299-82 | mouse |

TABLE 8

Non-limiting Examples of commercially available antibodies for CD44 (human and unconjugated.

| Company | Catalogue Number | Host |
|---|---|---|
| eBioscience | 16-0441-81 | Rat |
| Novus | NBP1-31121 | Rabbit |
| Thermo | PA5-32327 | Rabbit |
| Gentex | GTX50755 | Rabbit |
| Cell Signaling | 5640S | Mouse |
| Abcam | ab103552 | Rabbit |
| Abnova | H00000960-M03 | Mouse |
| antibodies-online | ABIN871672 | Rabbit |
| R & D Systems | AF3660 | Sheep |
| BD Biosciences | 555476 | Mouse |
| Abbiotec | 252831 | Mouse |
| Bethyl Laboratories | A303-872A | Rabbit |
| Proteintech Group | 15675-1-AP | Rabbit |
| Enzo Life Sciences | ALX-801-089-C100 | Mouse |
| Cell Science | 852.603.020 | |
| Merck Millipore | 217594-100UL | Rat |
| Life Technologies | 336700 | Mouse |
| Santa Cruz | sc-53503 | Mouse |
| ProSci | 79-668 | Rabbit |
| MP Biomedicals | 08D526000 | Mouse |
| Cedarlane | CLX47AP | Mouse |

TABLE 9

Non-limiting examples of commercially available ELISA Kits for CD44.

| Company | Catalogue Number |
|---|---|
| Cell Sciences | 850.570.192 |
| MyBioSource.com | MBS335446 |
| Sino Biological | SEK12211 |
| Biotrend Chemikalien | BMA-27215 |
| Antibodies online | ABIN366268 |
| Enzo Life Sciences | ALX-850-053-KI01 |
| DRG International | EIA4876 |
| Kamiya Biomedical Company | KT-032 |
| abcam | AB45912-2 |
| Novus | NBP1-87599 |
| CUSABIO | CSB-E11846H |

Antibodies directed against OPN, CD44 and integrins ($\alpha_5$, $\beta_1$, $\beta_3$, $\beta_5$) are included within the scope of this invention as they can be produced by well established procedures known to those of skill in the art.

Additionally, any secondary antibodies, either monoclonal or polyclonal, directed to the first antibodies would also be included within the scope of this invention.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl2, or R1N=C=NR, where R and R1 are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ¹/₁₀ of the original amount used to immunize) in Freund's complete adjuvant by subcutaneous injection at multiple sites. Seven to 14 days later the animals are bled, and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein, the term "purified" in the expression "purified antibody" is simply meant to distinguish man-made antibody from an antibody that may naturally be produced by an animal against its own antigens. Hence, raw serum and hybridoma culture medium containing anti-OPN antibody are "purified antibodies" within the meaning of the present invention.

As used herein, the terminology "blood sample" is meant to refer to blood, plasma or serum.

As used herein, the terminology "cell sample" is meant to refer to a sample containing cells expressing the desired GPCR(s) in sufficient amount to detect a cellular response in in order to classify the subject into one of functional groups FG1, FG2 and FG3. The cells in the cell sample may be any type of cells as long as they express the desired GPCR to be tested. The cells used herein naturally express one or more receptors coupled to $G_i$ proteins and were selected in part for their accessibility for collection from subjects. Hence, cells such as osteoblasts, osteoclasts, peripheral blood mononuclear cell (PBMC) (inherently including principally lymphocytes but also monocytes) and myoblasts are advantageously accessible and may conveniently be used in the methods of the present invention. Blood cells (e.g., PBMCs, platelets (thrombocytes), etc.) in particular are particularly accessible and provide for a more rapid testing. Any blood cell can be used for the methods of the present invention so long as it possesses at least one GPCR receptor coupled to a Gi protein. The cells can be fresh or frozen and may or may not have been cultured (expanded) prior to testing. The "sample" may be of any origin including blood, saliva, tears, sputum, urine, feces, biopsy (e.g., muscle biopsy), as long as it contains cells expressing the desired GPCR(s).

The articles "a," "an" and "the" are used herein to refer to one or to more than one (i.e., to at least one) of the grammatical object of the article.

The term "including" and "comprising" are used herein to mean, and re used interchangeably with, the phrases "including but not limited to" and "comprising but not limited to".

The terms "such as" are used herein to mean, and is used interchangeably with, the phrase "such as but not limited to".

The present invention is illustrated in further details by the following non-limiting examples.

EXAMPLE 1

AIS Endophenotype and Brace Treatment Outcome

METHODS: A retrospective study was performed with 67 AIS patients having had a blood test (cell-based assay), seen between January 2007 and November 2012 and having completed treatment with TLSO braces respecting standard prescription criteria (23 h per day). AIS patients were stratified according to the method developed by Moreau et al. 2004 (Moreau et al., 2004; Akoume et al., 2010) based upon the measurement of a differential signaling impairment of receptors coupled to G inhibitory proteins (Gi) allowing their classification into three functional groups (i.e., biological endophenotypes FG1, FG2 or FG3). Cobb angles were measured by single blind observer in brace and at the end of treatment and compared to their initial values. Progression of the curvature was defined by 6° angle increase (Nachemson et al., 1995). Treatment was considered a success if final Cobb angle was 45° or no surgery was required (Richards et al., 2005). Association between group classification and treatment outcome was analysed with $Chi^2$ test in a contingency table. Logistic regression models were performed for odds ratio calculation. Group comparability at time of prescription was verified using ANOVA and $Chi^2$ test: groups were not different on mean Cobb angle for all curves, Risser sign (i.e., amount of calcification of human pelvis as a measure of maturity) nor age.

Results: The patient distribution is reported in Table 10 (15 in FG1, 27 in FG2, and 25 in FG3).

TABLE 10

Statistical analysis of the patient distribution comparing 3 success criteria (Cobb at the end of treatment ≤45°, Cobb angle progression ≤6° and no need for surgery)

|  | success | failure | Odds ratio | |
|---|---|---|---|---|
| Final Cobb ≤45° | | | | |
| FG1 | 6 (40%) | 9 (60%) | 1 | |
| FG2 | 16 (59%) | 11 (41%) | 2.18 | p = 0.235 |
| FG3 | 21 (84%) | 4 (16%) | 7.88 | p = 0.007 |
| Total | 43 (64%) | 24 (36%) $\chi^2$ = 8.4 (p = 0.015) | | |
| Cobb angle progression ≤6° | | | | |
| FG1 | 6 (40%) | 9 (60%) | 1 | |
| FG2 | 13 (48%) | 14 (52%) | 1.39 | p = 0.612 |
| FG3 | 15 (60%) | 10 (40%) | 2.25 | p = 0.224 |
| Total | 33 (49%) | 34 (51%) $\chi^2$ = 1.6 (p = 0.444) | | |
| No need for surgery | | | | |
| FG1 | 8 (53%) | 7 (47%) | 1 | |
| FG2 | 20 (74%) | 7 (26%) | 2.5 | p = 0.177 |
| FG3 | 22 (88%) | 3 (12%) | 6.4 | p = 0.02 |
| Total | 50 (74%) | 17 (25%) $\chi^2$ = 5.96 (p = 0.05) | | |

Globally, in all patients who had brace success, the majority were from FG2 and FG3. There was a clear association between the functional group and success of the treatment regarding the progression of curvature ≤45° criteria. Group FG3 patients were more likely to have success with brace treatment than in group FG1. The association was in the same direction for group FG2. Regarding the ≥6° of progression criteria, an increased proportion of success was noted in FG3. Success in treatment in regard to preventing surgery was statistically different between the groups (Chi 2 (2, 67)=5.96, p=0.05). It is 6.4 times more likely to prevent surgery than to have one in group FG3 compared to FG1 (p=0.02). Again, a tendency towards increased chance of preventing surgery was found in group FG2 compared to FG1.

In order to confirm the above results and determine whether the specific type of brace treatment used influenced outcome, a retrospective study was performed with 90 AIS patients previously stratified among three biological endophenotypes according to a cell-based assay, as described above, allowing their classification into three functional groups (FG1, FG2 or FG3). Patients completed the non-rigid/dynamic (SpineCor™) brace treatment following standard prescription criteria. Cobb angles were measured by a single blind observer in brace and at the end of treatment and compared to their initial values. Progression of the curvature was defined by a 6° Cobb increase and treatment was considered a success if final Cobb angle was ≤45° or no surgery was required. Association between group classification and treatment outcome was analysed with Chi2 test. Logistic regression models were performed for odds ratio calculation. Group comparability at time of prescription was verified using ANOVA and Chi2 test: no differences for mean Cobb angle, Risser sign, BMI nor age.

Results. The patient distribution is reported in Table 11 (24 in FG1, 27 in FG2, and 39 in FG3). As for the first study with rigid brace treatment, globally, in all patients who had brace success, the majority were from FG3. There was a clear association between the functional group and the success of the treatment regarding the final Cobb angle ≤45° criteria (Chi2=6.7, p=0.034) and in regard to preventing progression of 6° (Chi2=15.7, p<0.001). Being classified as FG3 was 4 times (p=0.028) and 7.6 times (p=0.001) more likely to lead to treatment success than failure compared to FG1, respectively for the ≤45° final Cobb and ≤6° progression criteria. There was no significant difference in treatment outcomes between groups FG1 and FG2.

TABLE 11

Statistical analysis of the patient distribution treated with SpineCor ™ brace comparing 2 success criteria (Cobb at the end of treatment ≤45° and Cobb angle progression)

|  | success | failure |  | Odds ratio |  |
| --- | --- | --- | --- | --- | --- |
| Final Cobb ≤45° |
| FG1 | 15 (63%) | 9 (37%) |  | 1 |  |
| FG2 | 17 (63%) | 10 (37%) |  | 1.02 | p = 0.973 |
| FG3 | 34 (87%) | 5 (13%) |  | 4.08 | p = 0.028 |
| Total | 66 (73%) | 24 (27%) | $\chi^2$ = 6.7 (p = 0.034) |
| Cobb angle progression ≤6° |
| FG1 | 5 (21%) | 19 (79%) |  | 1 |  |
| FG2 | 8 (30%) | 19 (70%) |  | 1.60 | p = 0.474 |
| FG3 | 26 (67%) | 13 (33%) |  | 7.60 | p = 0.001 |
| Total | 39 (43%) | 51 (57%) | $\chi^2$ = 15.7 (p < 0.001) |

Conclusion. Globally, in all patients who had brace success, the majority were from FG2 and FG3. Outcomes of bracing were most favorable for patients presenting the FG3 endophenotype, independently of the type of bracing. There was a clear association between the functional group and success of the treatment regarding the progression of curvature 45° criteria and the Cobb angle progression ≤6. Furthermore, results showed a tendency towards increased chance of preventing Cobb angle progression (≤6) and surgery in group FG2 compared to FG1.

EXAMPLE 2

Circulating OPN Level Variations with Age in AIS and Control Subjects

Data was obtained with AIS patients (N=884) in Phase 2 followed at Sainte-Justine Hospital, at the Shriners Hospital or Montreal Children's Hospital, in Montreal, Québec, Canada. Age matched control subjects (N=254) were recruited from primary and secondary schools in Montreal. The plasma was collected in tubes containing EDTA and circulating OPN levels were measured in blood samples from control and AIS subjects of age 9 to 18 by ELISA.

As shown in FIGS. 2A-2B, circulating OPN blood level generally increases until between the age of 11 and 12 years old and then begin to decrease with age. OPN levels are significantly higher in AIS than control subjects at all times and follow generally the same variation pattern with age.

EXAMPLE 3

Figure 3:
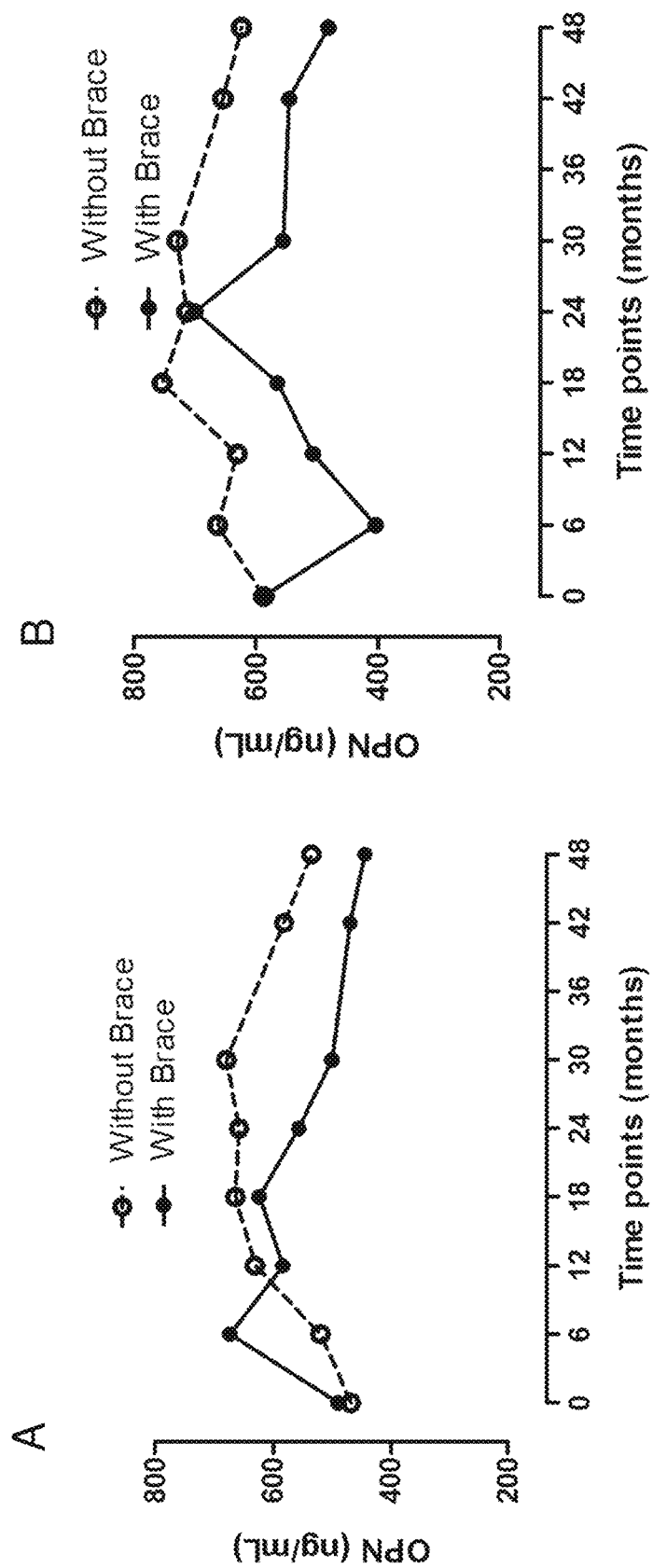
FIGS. 3A-3B show OPN circulating levels variation in blood sample of AIS subjects during brace treatment.
Figure 5:
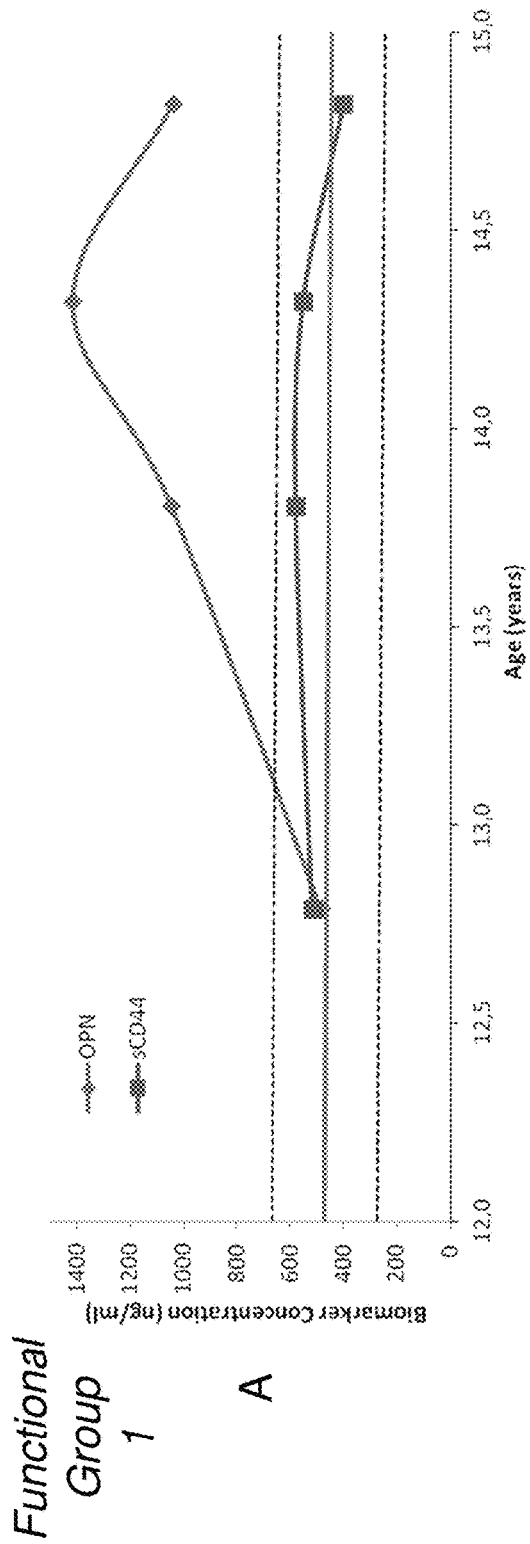
FIGS. 5A-5B.
Figure 6:
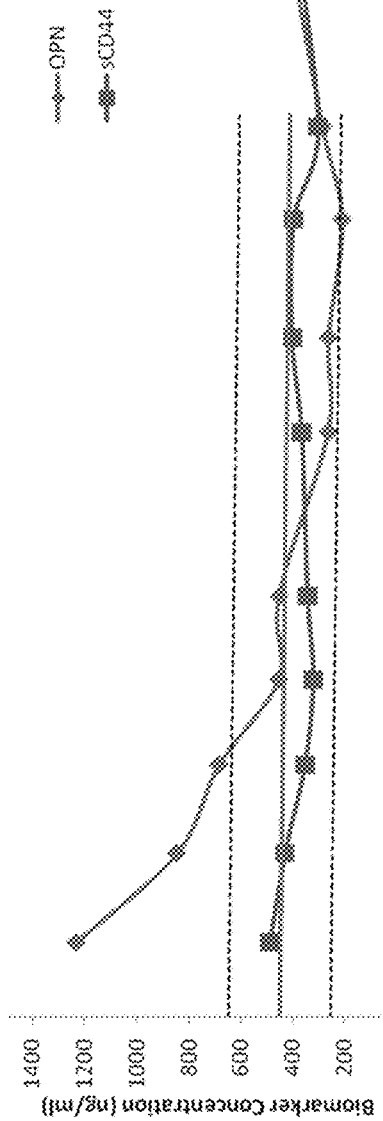
FIGS. 6A-6B.
Figure 7:
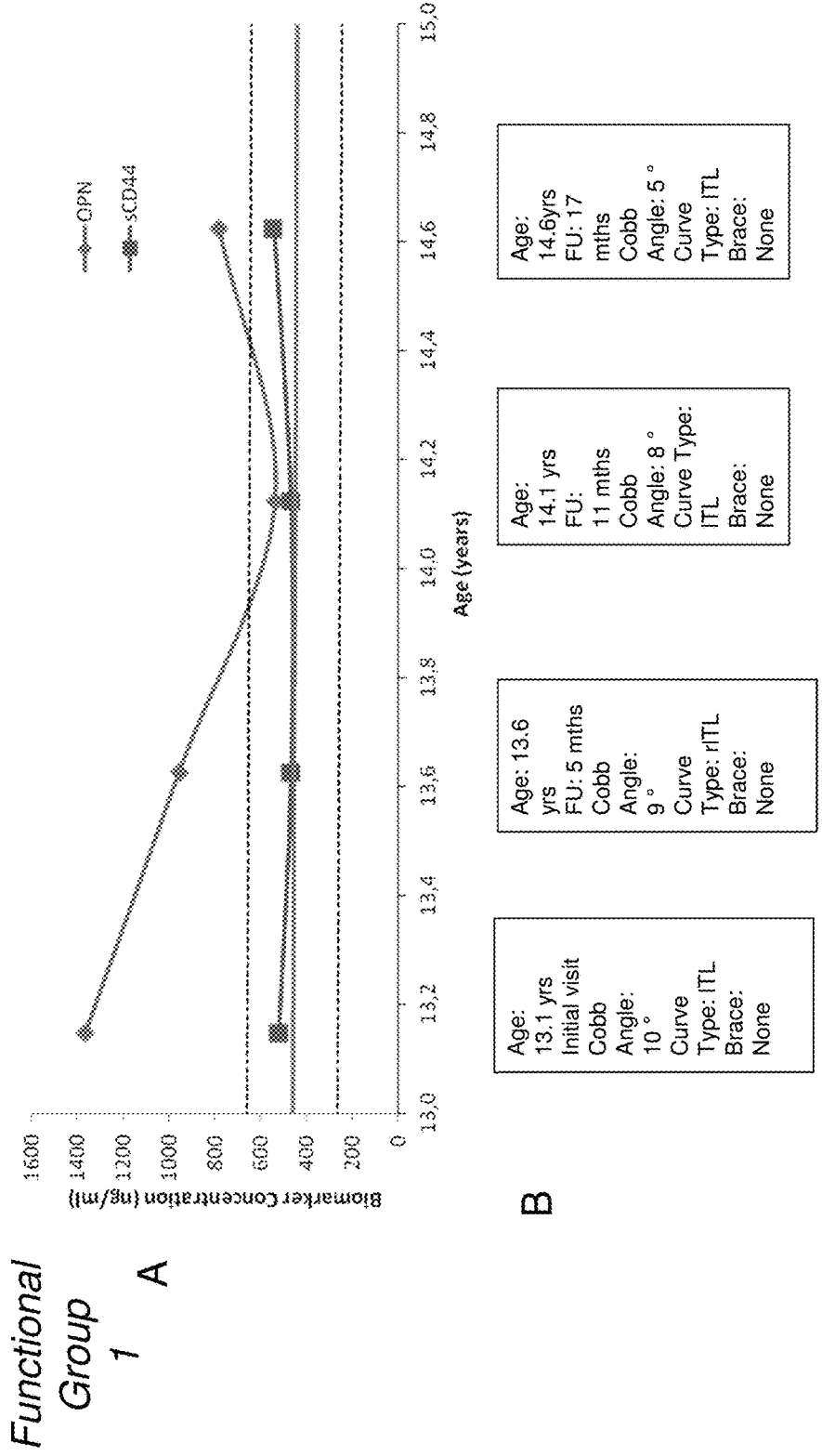
FIGS. 7A-7B.
Figure 8:
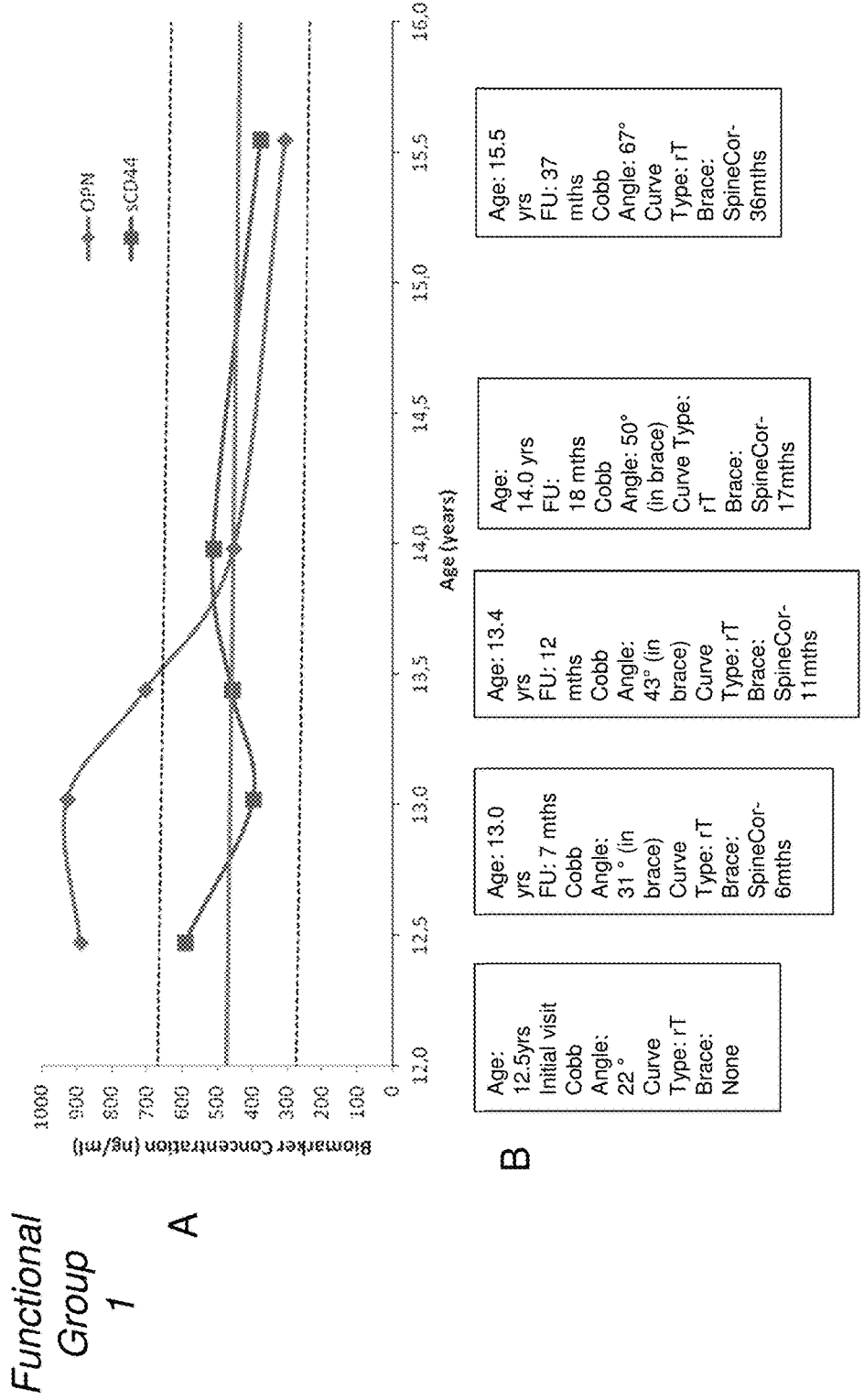
FIGS. 8A-8B.
Figure 9:
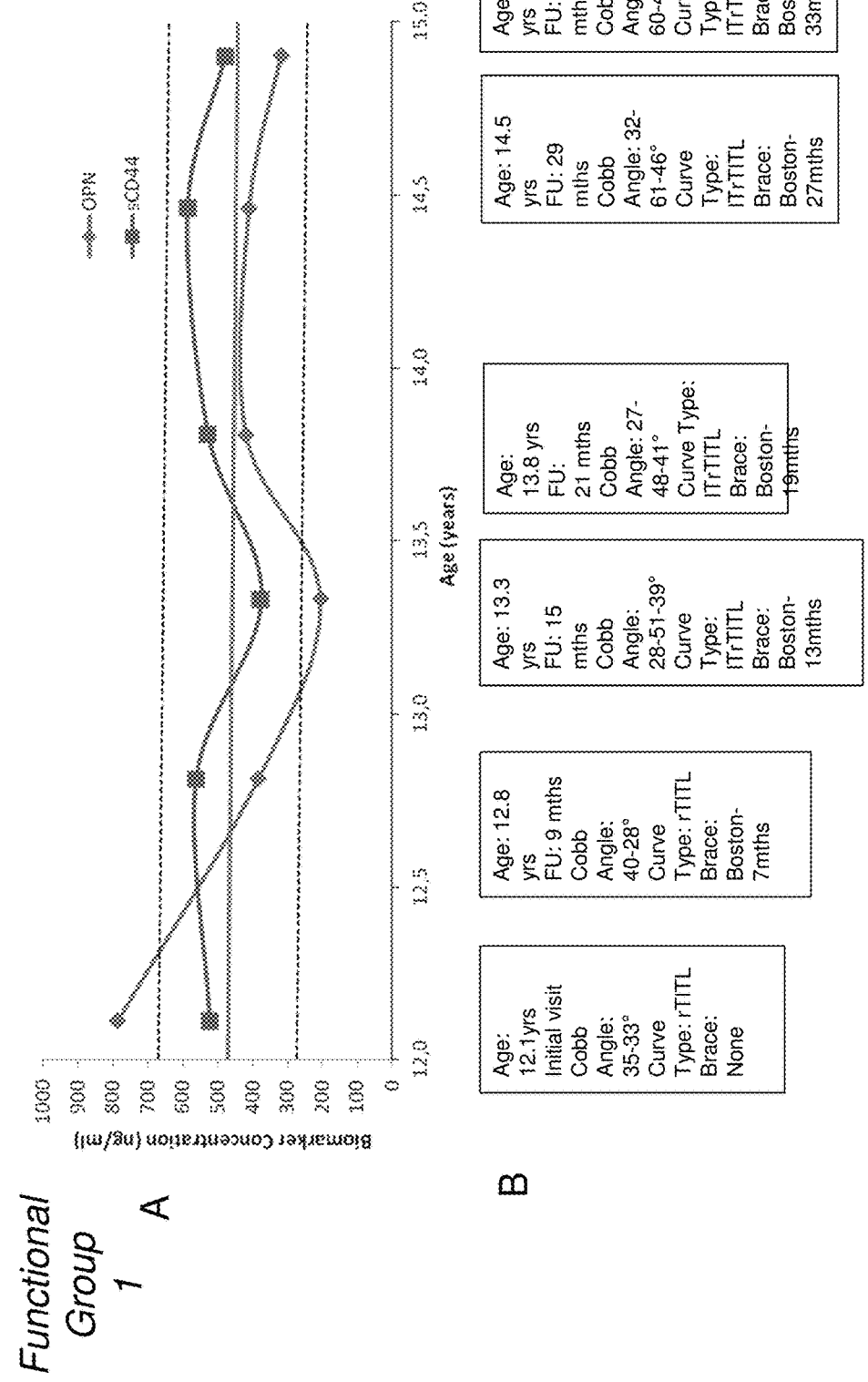
FIGS. 9A-9B.
Figure 10:
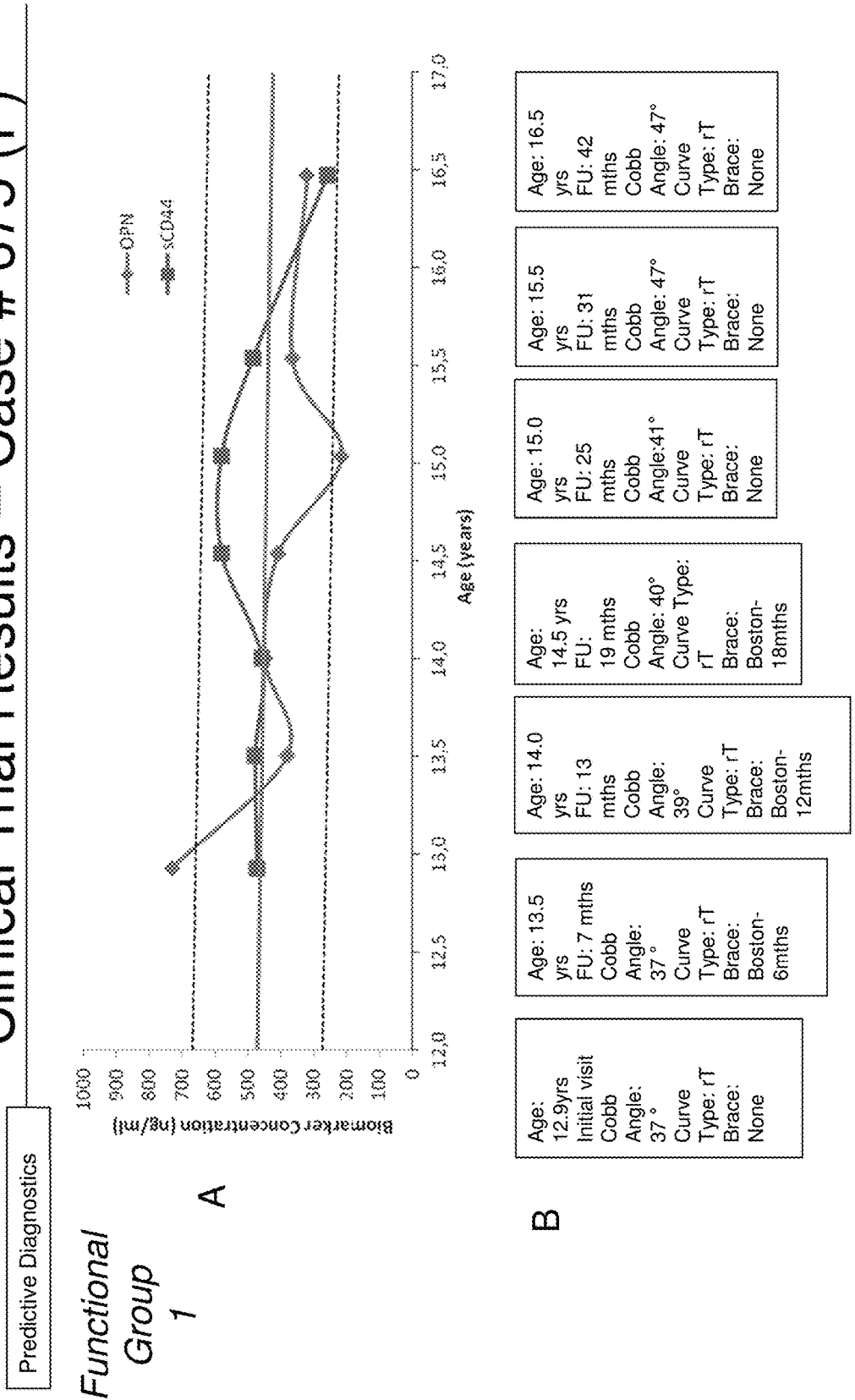
FIGS. 10A-10B.
Figure 11:
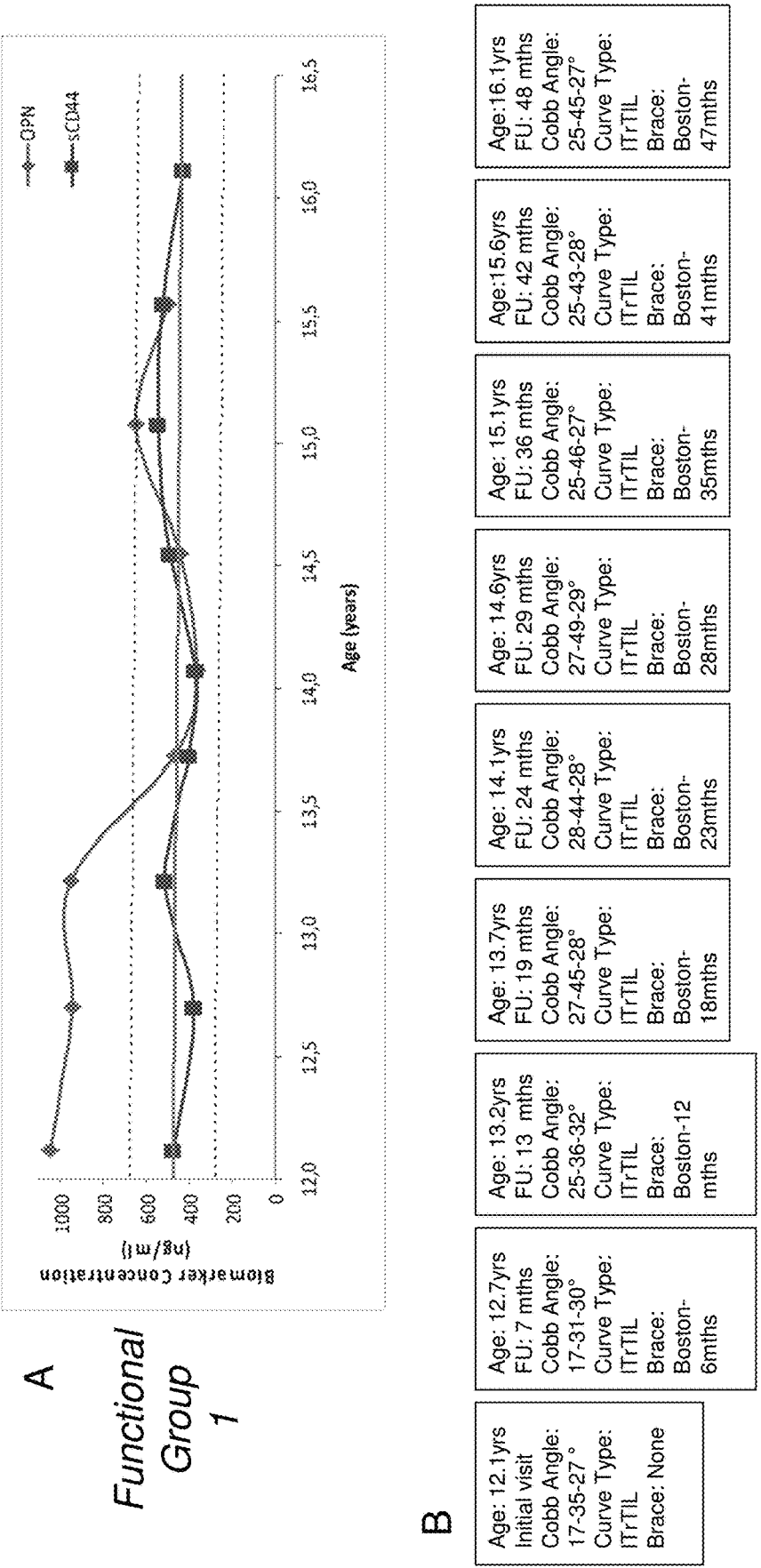
FIGS. 11A-11B.
Figure 13:
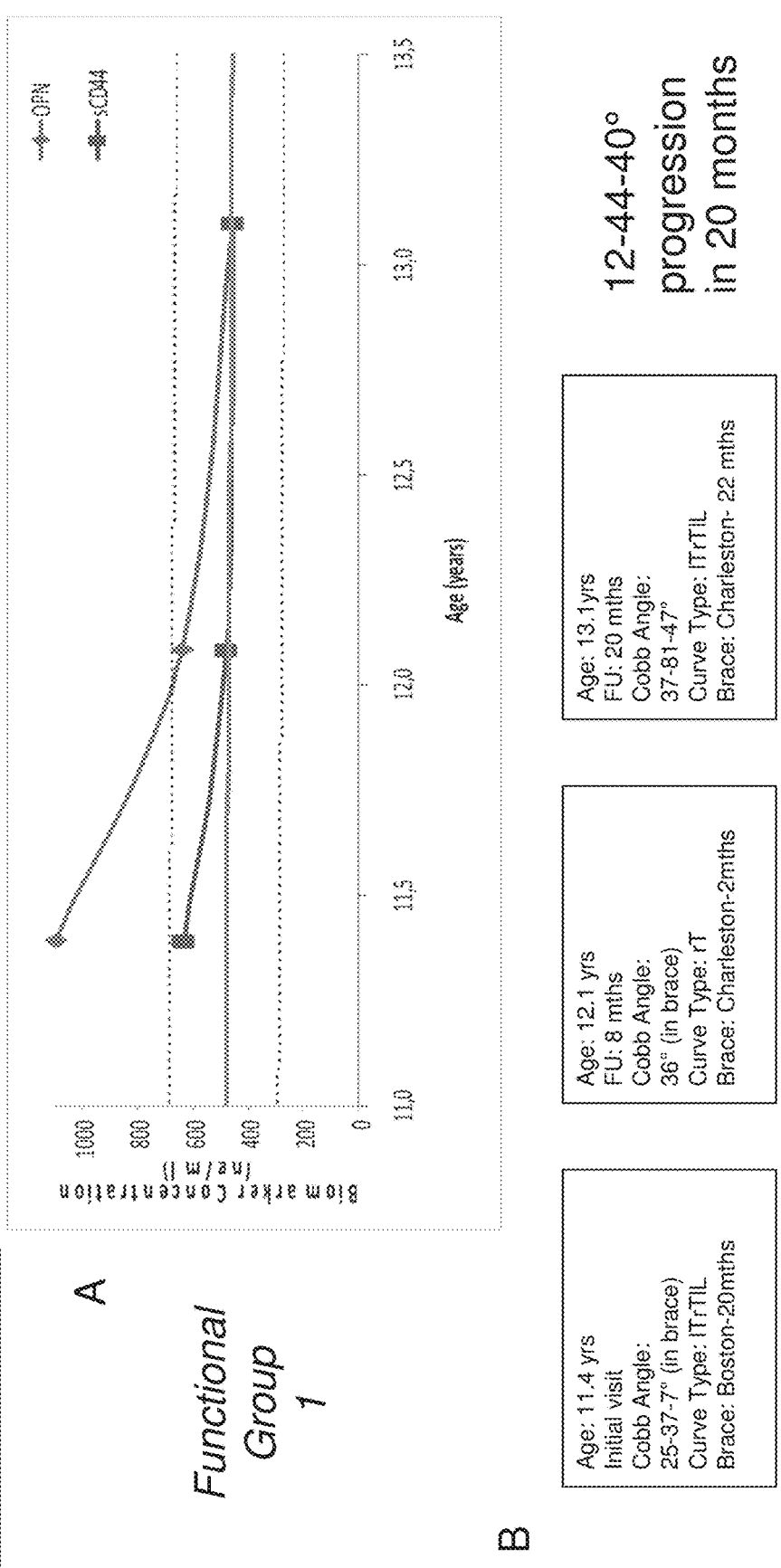
FIGS. 13A-13B.
Figure 14:
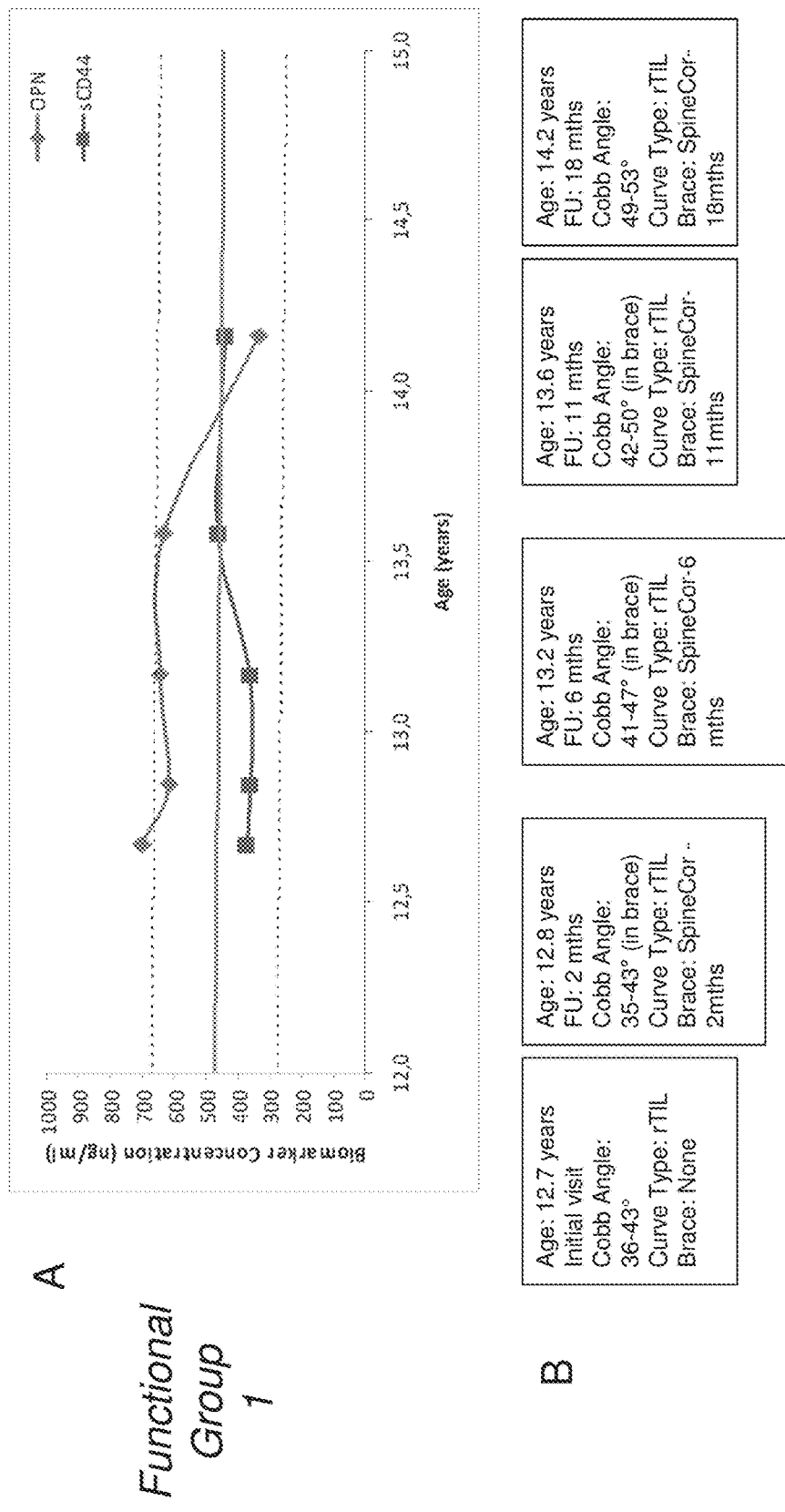
FIGS. 14A-14B.
Figure 15:
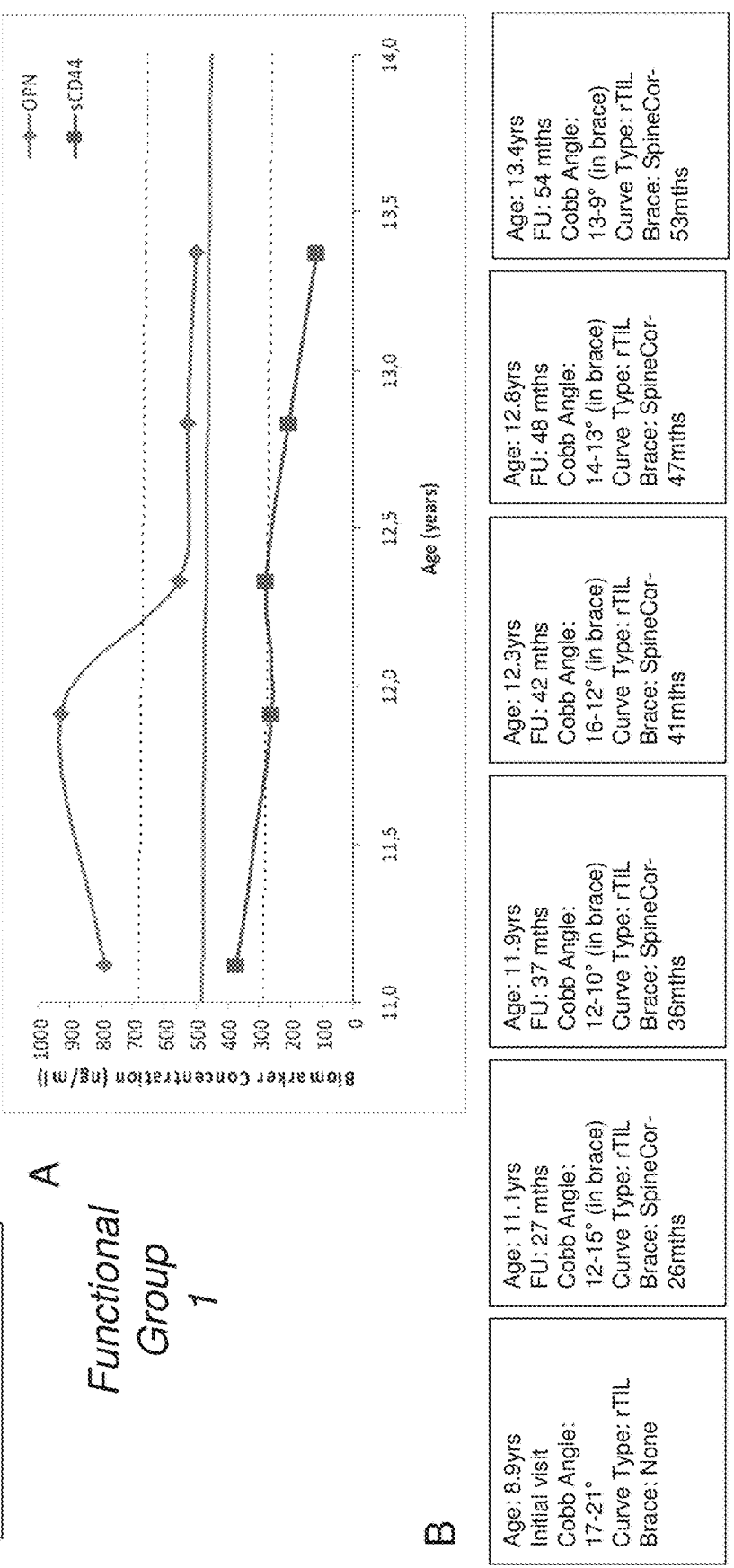
FIGS. 15A-15B.

Circulating OPN Level Variations Upon Brace Treatment in Subjects Having High and Low Levels Of OPN The effect of brace treatment on the level of circulating OPN in AIS subjects was studied. Data was obtained with AIS patients in Phase 2 followed at Sainte-Justine Hospital, at the Shriners Hospital or Montreal Children's Hospital, in Montreal, Québec, Canada. The plasma was collected in tubes containing EDTA and OPN was measured with ELISA (IBL International, catalogue #JP27158). Circulating OPN levels were measured in blood samples from control and AIS subjects every 6 months during four years. Subjects were separated in two groups. FIG. 3A presents OPN levels for subjects which had initial (i.e., before the beginning of brace treatment) circulating OPN levels below 600 ng/mL, treated with a brace (N=94) and age-matched untreated control subjects (N=330). FIG. 3B shows OPN levels for subjects which had initial circulating OPN levels 600 ng/ml, treated (N=153) with a TLSO brace and age-matched untreated control subjects (N=310).

As shown in FIG. 3A, in subjects having initial low levels of circulating OPN (i.e., below about 600 ng/ml), brace treatment first increased OPN levels. OPN levels were significantly higher in subjects treated with a brace, 6 months after treatment and returned to the same level than subjects not treated with a brace after about 12 to 18 months of brace treatment. Brace treatment then induced a decrease in OPN levels which was maintained during the rest of the study, i.e., up to 48 months (FIG. 3A).

In subjects having high levels of OPN at the beginning of the study (i.e., about 600 ng/ml), brace treatment had the opposite effect. It produced an important decrease in circulating OPN level within the first 6 months. Then, OPN level increased slowly until it reached about 600 ng/ml (i.e., about the same level as untreated subjects) about 24 months after the beginning of treatment and decreased again after. Circulating OPN levels remained below that of AIS subjects not treated with a brace, except for a short period around 24 months of treatment, where OPN levels reached a peak and overlapped with OPN levels of untreated subjects (FIG. 2B).

Based on the results presented in FIGS. 3A and 3B, it appears that when the treatment begins with circulating OPN levels below about 600 ng/mL, brace treatment generally first causes an increase in OPN production, whereas when treatment begins with OPN concentrations at or above this value, brace treatment induces a reduction in circulating levels of OPN. These results show that long term brace treatment generally decreases the circulating level of OPN and suggest the presence of a retroinhibition mechanism which regulates circulating OPN levels when they reach around 600 ng/ml.

EXAMPLE 4

Figure 17:
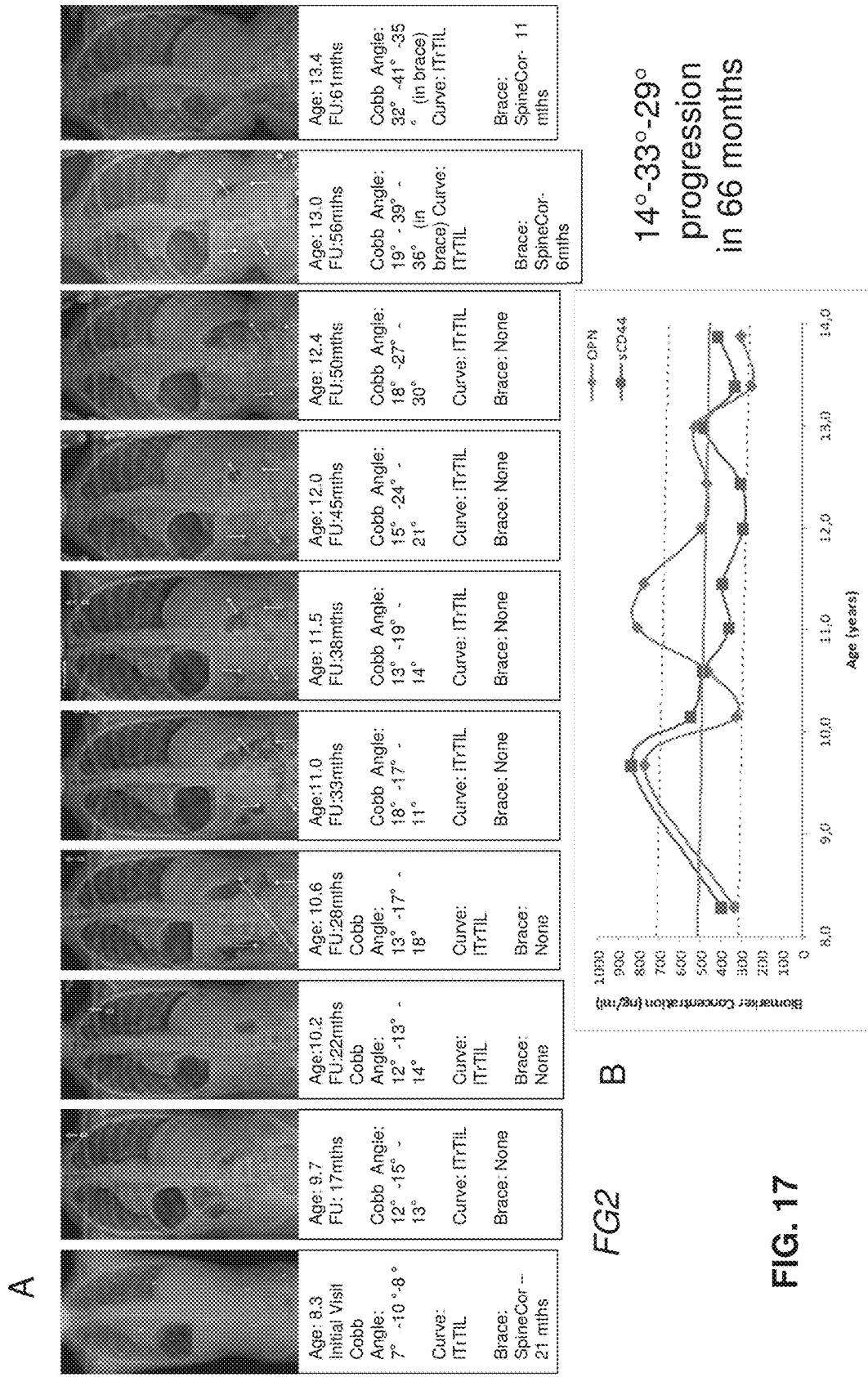
FIGS. 17A-17B.

Association Between OPN and SCD44 Levels and Curve Progression in AIS Subjects According to their Functional Group The relation between curve progression and OPN and sCD44 levels was followed in AIS subjects. An association between OPN levels and curve progression was observed. In FG1 subjects, low levels of OPN (≤than about 500 ng/ml) correlated with curve progression (see for examples FIGS. 6A-6B, 8A-8B, 9A-9B and 10A-10B) while high levels (e.g., at or above 1000 ng/ml) were generally associated with absence of curve progression or smaller rate of progression (see for example FIGS. 2A-2B and 7A-7B). For FG2 and FG3 subjects, high levels of OPN were more often associated with curve progression (see for example FIG. 17B). FIGS. 4A-19B shows examples of OPN and sCD44 levels variations observed with time and curve progression in AIS subjects for each functional group. No clear correlation was observed between curve progression and sCD44.

EXAMPLE 5

Figure 20:
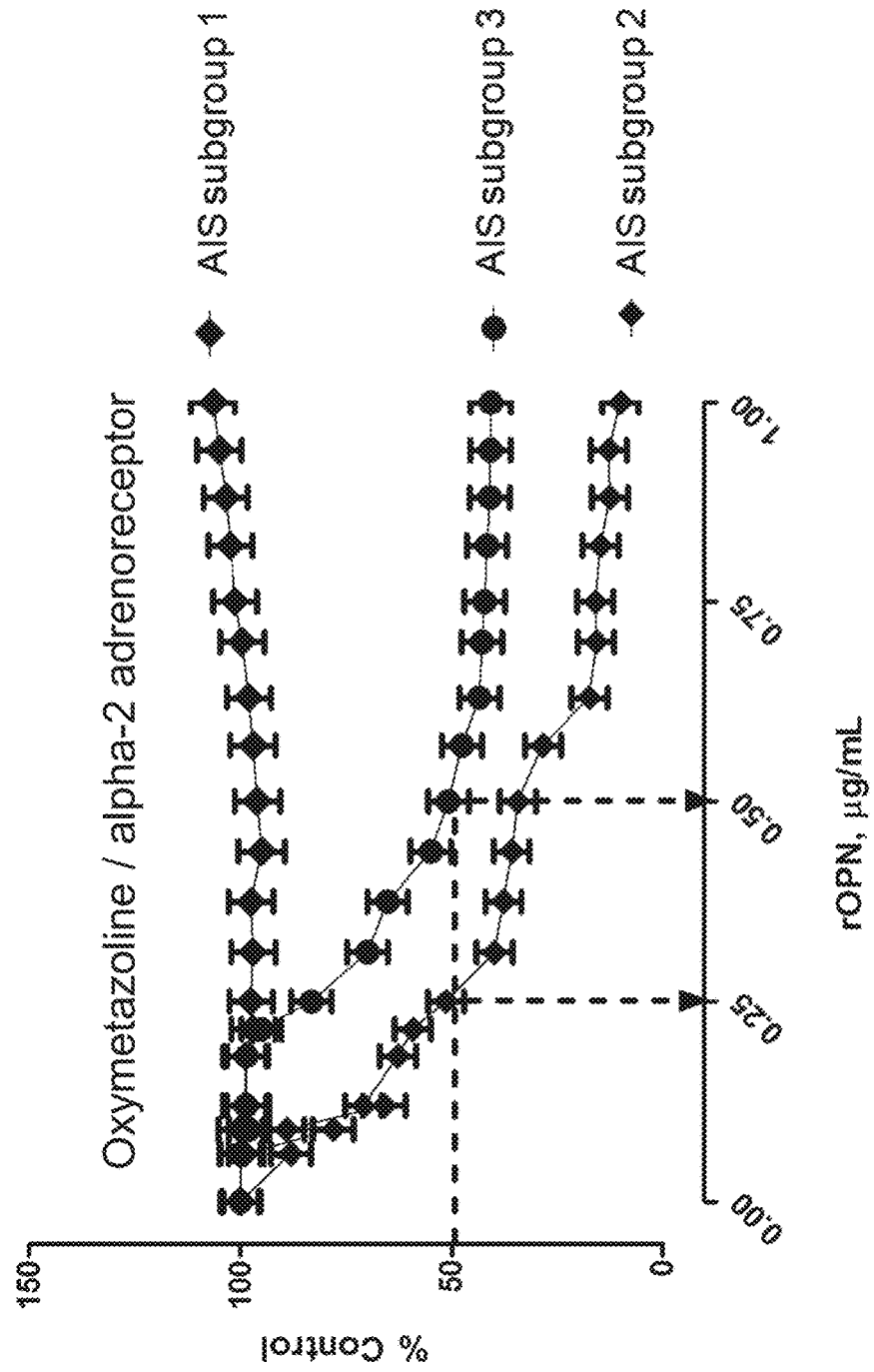
FIG. 20 shows that cell response to OPN is genetically programmed in AIS patients. Gi-mediated cellular response in the presence of increasing amounts of rOPN was measured by cellular impedance using the CellKey™ system (Akoume et al., 2010; and Akoume et al., 2013 (J. Vis. Exp.)) in functional groups FG1, FG2 and FG3.
Figure 21:
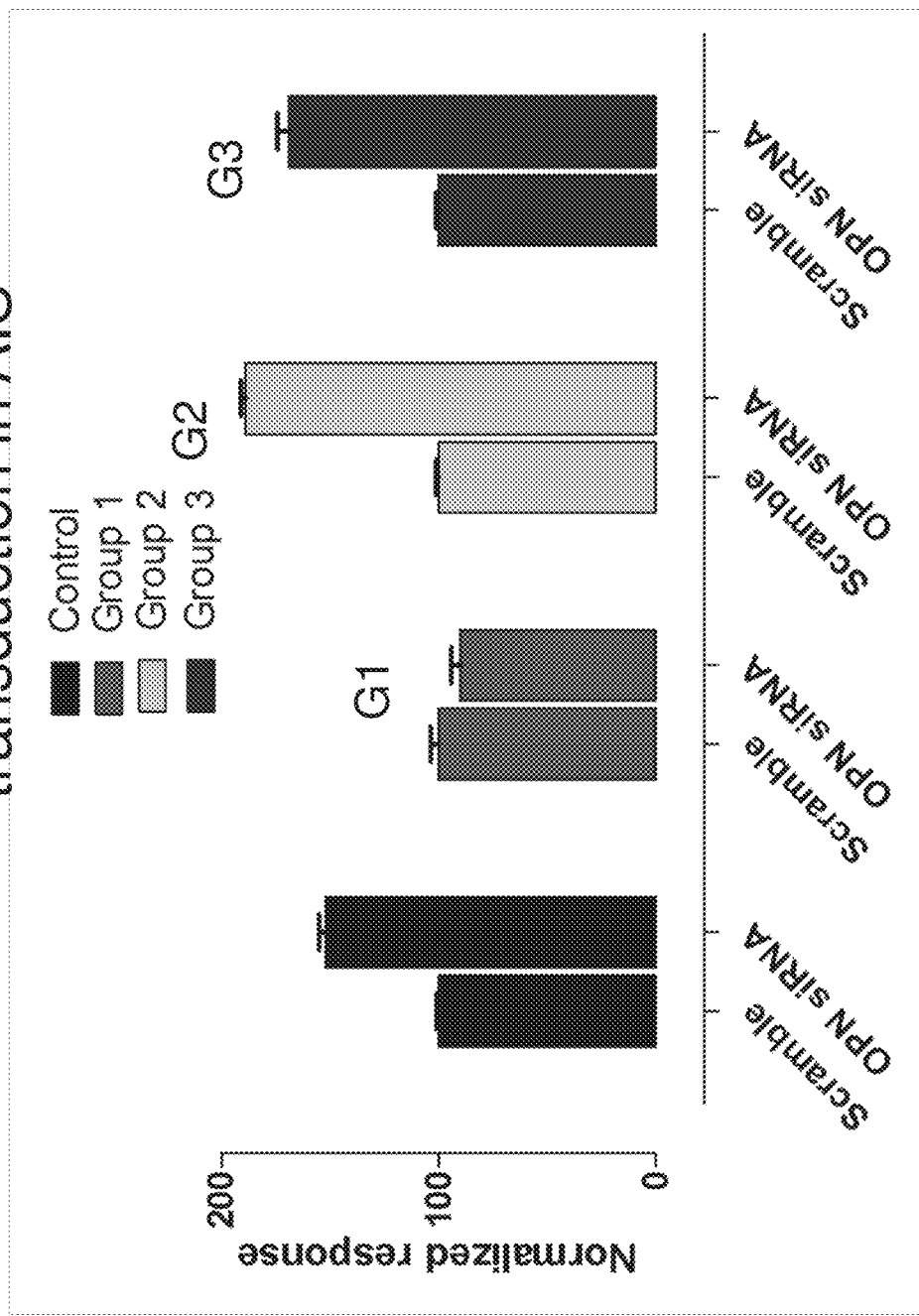
FIG. 21 shows that knock down of OPN rescued Gi-mediated cell signalling in AIS subjects of FG2 and FG3 functional groups. Gi-mediated cellular response in the presence siRNAs against rOPN was measured by cellular impedance using the CellKey™ system (Akoume et al., 2010; and Akoume et al., 2013 (J. Vis. Exp.)) in functional groups FG1, FG2 and FG3.
Figure 22:
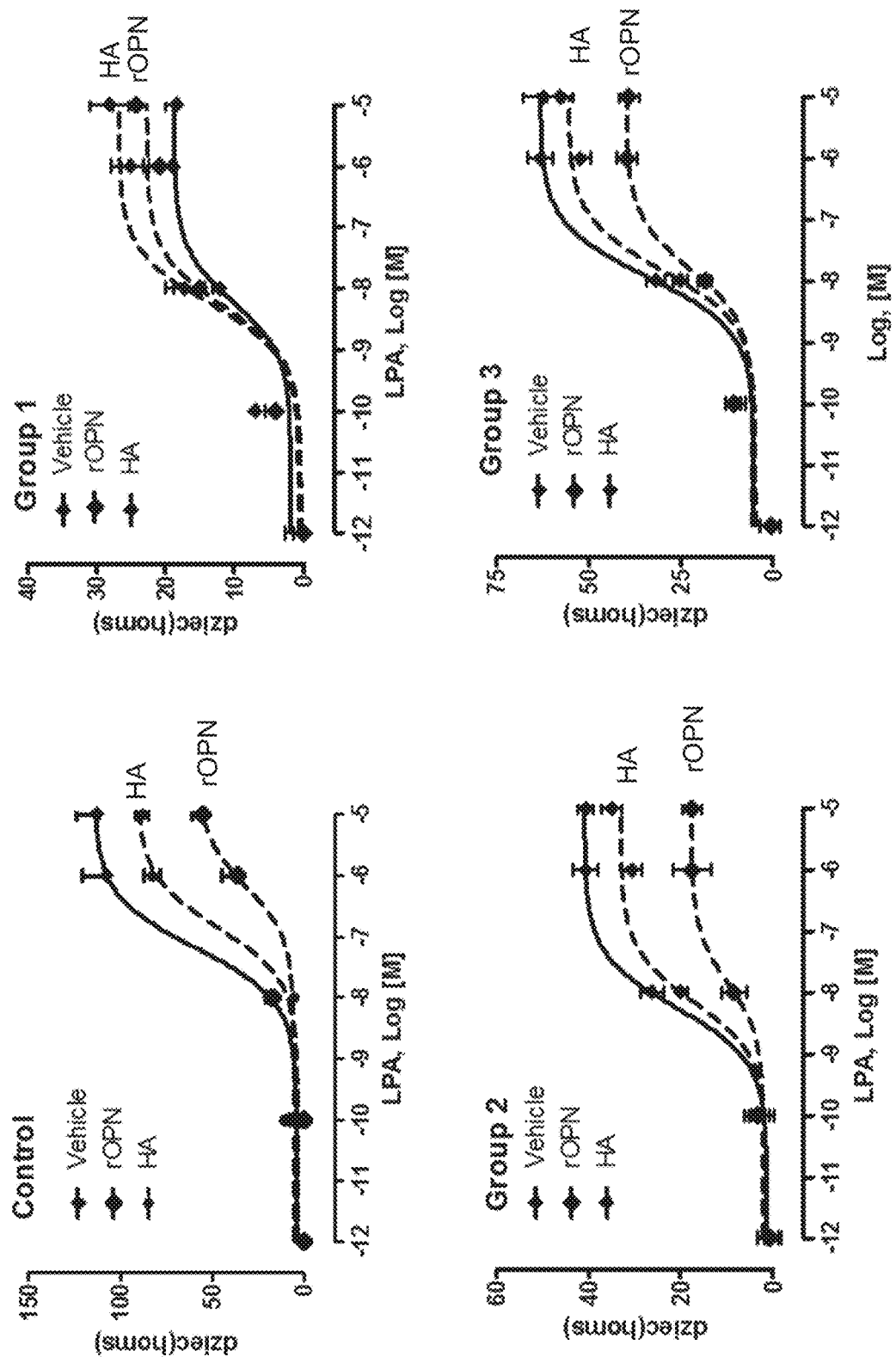
FIG. 22 shows the effect of OPN and hyaluronic acid treatment on GiPCR signaling in cells of healthy and AIS subjects according to their biological endophenotype. Osteoblasts from healthy subjects and AIS patients of each endophenotype (FG1, FG2 and FG3) were treated with vehicle, OPN (500 ng/ml) or HA (10 µM). The Gi-mediated cellular response in the presence of increasing amounts of LPA was measured by cellular impedance using the CellKey™ system.
Figure 23:
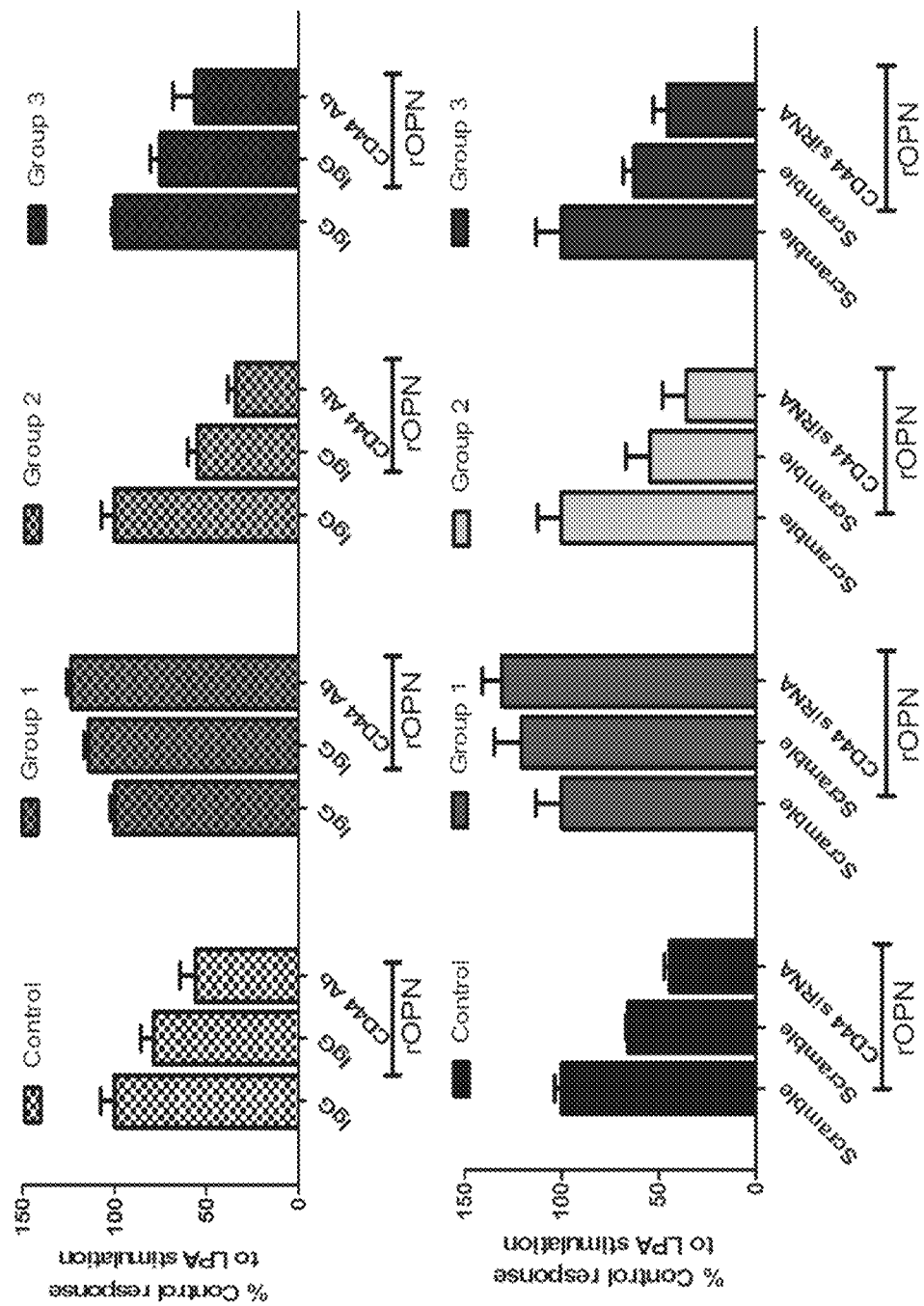
FIG. 23 shows that absence or inhibition of CD44 potentiates the effects of OPN on Gi-mediated cell signaling in each biological endophenotype groups (FG1, FG2 and FG3). CD44 activity (A) or expression (B) was inhibited in osteoblasts from control, FG1, FG2 and FG3 patients and the effect on OPN-dependent inhibition of Gi-mediated cell signaling was monitored using the CellKey™ system following stimulation with LPA. Inhibition of CD44 using an anti-CD44 antibody (A) or a siRNA against CD44 (B) further decreased Gi-mediated cell signaling in control, FG2 and FG3 subjects while it further increased Gi-mediated cell signaling in FG1 subjects.
Figure 24:
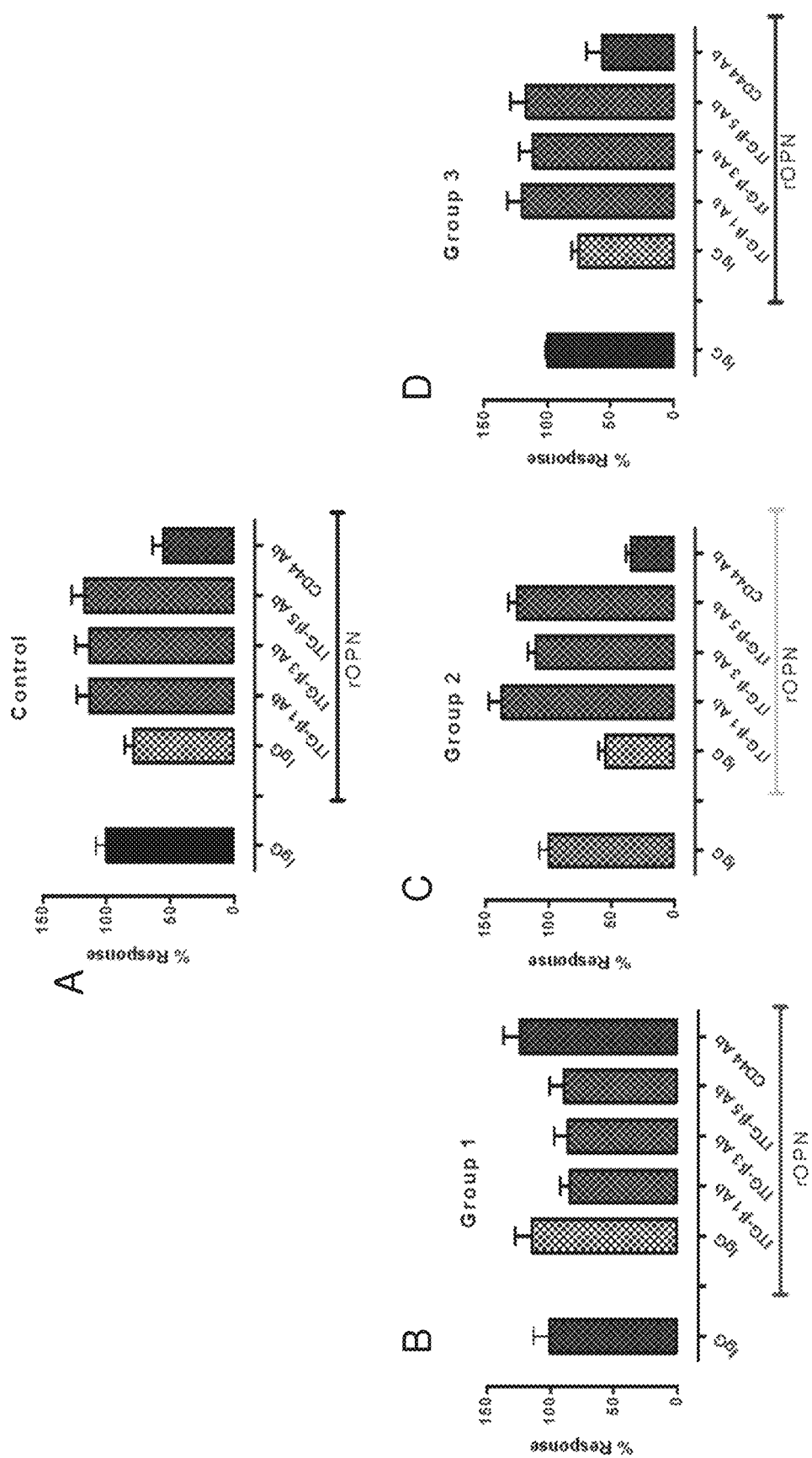
FIGS. 24A-24D show that OPN-dependent inhibition of Gi-mediated cell signaling involves integrins. Antibodies against integrins $\beta_1$, $\beta_3$ and $\beta_5$ reverse the effect of OPN on Gi-mediated response in FG2 and FG3 subjects only, while blockade of CD44 further potentiates the effect of OPN.
Figure 25:
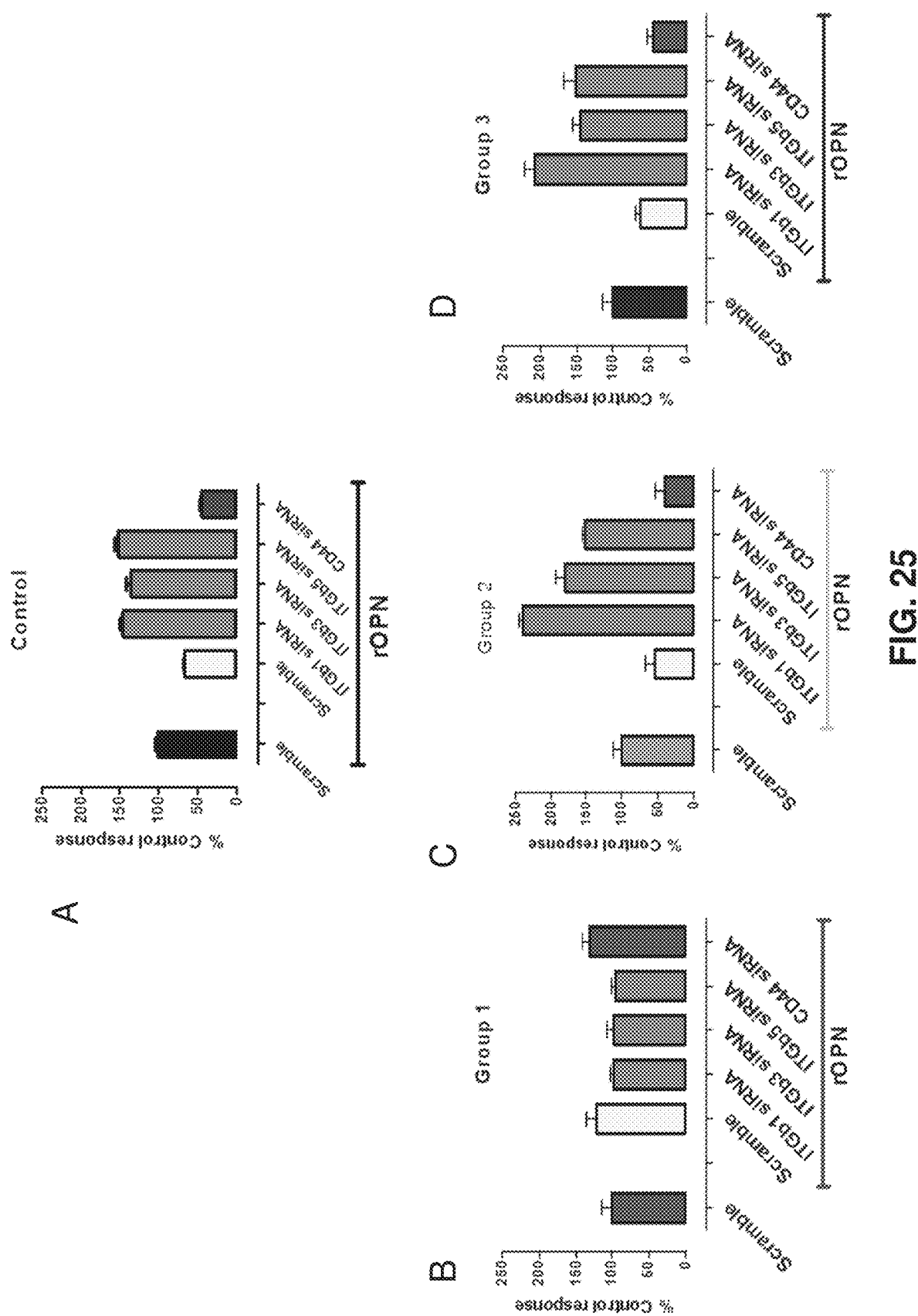
FIGS. 25A-25D shows that OPN-dependent inhibition of Gi-mediated cell signaling involves integrins. SiRNAs against integrins $\beta_1$, $\beta_3$ and $\beta_5$ reversed the effect of OPN on Gi-mediated response while blockade of CD44 further potentiated the effect of OPN.

OPN Enhances Gi-Mediated Cell Signalling in FG1 Subjects and Decreases Gi-Mediated Signalling in FG2 and FG3 Subjects The variation in Gi-mediated cell signaling in response to OPN in each functional group (FG1, FG2 and FG3) was studied. FIGS. 20 and 21 show the response to OPN (increasing doses) on osteoblasts isolated from patients classified into functional groups FG1, FG2 and FG3. OPN enhances Gi signaling in the FG1 functional group and aggravates the impairment in the FG2 (hypersensitive) and FG3 (sensitive) functional groups (FIG. 20). Furthermore, MC3T3-E1 cells were used to check the effect of the knockdown of OPN and its receptors. MC3T3-E1 osteoblasts cells were transiently transfected in serum-free medium, using Lipofectamine™ RNAiMAX reagent (Invitrogen) according to the manufacturers instructions and functional experiments were performed 48 h post transfection. Knock down of OPN expression in osteoblasts by siRNAs (CCA CAG CCA CM GCA GUC CAG AUU A (SEQ ID NO: 14)) increases Gi-mediated transduction in FG2 and FG3 subgroups while it tends to decrease the response in FG1 (FIG. 21).

EXAMPLE 6

Differential Effect of HA, CD44 and Integrins on Gi-Mediated Cell Signalling in FG1, FG2 and FG3 Functional Groups MC3T3-E1 cells were also used to check the effect of the knockdown of OPN's receptors by RNAi. Experimental conditions were as described for Example 5. The sequence of RNA oligonucleotides used for the knockdowns are: integrin β1 (CCU MG UCA GCA GUA GGA ACA UUA U (SEQ ID NO: 15)), integrin β3 (CCU CCA GCU CAU UGU UGA UGC UUA U (SEQ ID NO: 16)); integrin β5 (AGAAUGUCUGCUAAUCCACCCAAAA, HSS-105572, Life technologies (SEQ ID NO: 17), CUGAGGGCAAAC-CUUGUCAAAAAUG, HSS-105573, Life technologies (SEQ ID NO: 18); and GAAAUGGCUUCAAAUC-CAUUAUACA, HSS-179984, life technologies, (SEQ ID NO: 19)) and CD44 (GM CM GGA GUC GUC AGA MC UCC A (SEQ ID NO: 20)).

The scope of the claims should not be limited by the preferred embodiments set forth in the examples, but should be given the broadest interpretation consistent with the description as a whole.

The invention claimed is:

1. A method of treating a subject in need thereof comprising:
   (a) classifying the subject into functional group FG1, FG2 or FG3, wherein classifying the subject comprises:
   (i) determining changes in cellular impedance following Gi-stimulation, wherein a reduction of cellular impedance of more than 60 and up to 90% relative to a non scoliotic subject classifies the subject into FG1, a reduction of cellular impedance of 40-60% relative to a non scoliotic subject classifies the subject into FG2; and a reduction of cellular impedance of 10-40% relative to a non scoliotic subject classifies the subject into FG3;
   (ii) measuring changes in cAMP concentration following Gi-stimulation, wherein a cAMP increase relative to baseline cAMP concentration following forskolin stimulation classifies the subject into FG1, no significant change relative to baseline cAMP concentration following forskolin stimulation classifies the subject into FG2; and a cAMP decrease relative to baseline cAMP concentration following forskolin stimulation classifies the subject into FG3; or (iii) determining the phosphorylation pattern of Giα proteins, wherein phosphorylated Giα1, Giα2 and Giα3 classifies the subject into FG1; phosphorylated Giα1 and Giα2 and unphosphorylated Giα3 classifies the subject into FG2; and phosphorylated Giα2 and Giα3 and unphosphorylated Giα1 classifies the subject into FG3; or (b) measuring the level of osteopontin (OPN) in a blood sample from the subject; and (c) (c-i) selecting a subject classified into the FG2 or FG3 functional group, and treating that subject with a brace; or (c-ii) selecting a subject classified into the FG1 functional group, and having a level of OPN in his or her blood sample below 500 ng/ml, and treating that subject with a brace for 1 to 6 months.

2. The method of claim 1, wherein the method further comprises treating said subject with accupoint heat sensitive moxibustion; heat therapy with pad; electroacupuncture; thermal bath; or a combination of at least two of thereof.

3. The method of claim 1, further comprising measuring the level of OPN in a blood sample from the subject periodically during brace treatment.

4. The method of claim 3, wherein the level of OPN is measured once a month.

5. The method of claim 1, wherein the subject is a pediatric subject.

6. The method of claim 1, wherein the cellular impedance is measured by cellular dielectric spectroscopy (CDS).

7. The method of claim 1, wherein the subject is a subject diagnosed with adolescent idiopathic scoliosis (AIS).

* * * * *

SEQUENCE LISTING

```
<160> NUMBER OF SEQ ID NOS: 20

<210> SEQ ID NO 1
<211> LENGTH: 314
<212> TYPE: PRT
<213> ORGANISM: Homo Sapiens

<400> SEQUENCE: 1

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
```

```
            145                 150                 155                 160
Asp Ser Val Val Tyr Gly Leu Arg Ser Lys Ser Lys Lys Phe Arg Arg
                    165                 170                 175

Pro Asp Ile Gln Tyr Pro Asp Ala Thr Asp Glu Asp Ile Thr Ser His
                180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 2
<211> LENGTH: 1641
<212> TYPE: DNA
<213> ORGANISM: Homo Sapiens

<400> SEQUENCE: 2
ctccctgtgt tggtggagga tgtctgcagc agcatttaaa ttctgggagg gcttggttgt      60
cagcagcagc aggaggaggc agagcacagc atcgtcggga ccagactcgt ctcaggccag     120
ttgcagcctt ctcagccaaa cgccgaccaa ggaaaactca ctaccatgag aattgcagtg     180
atttgctttt gcctcctagg catcaccctgt gccataccag ttaaacaggc tgattctgga     240
agttctgagg aaaagcagct ttacaacaaa tacccagatg ctgtggccac atggctaaac     300
cctgacccat ctcagaagca gaatctccta gccccacaga atgctgtgtc ctctgaagaa     360
accaatgact ttaaacaaga gacccttcca gtaagtcca acgaaagcca tgaccacatg     420
gatgatatgg atgatgaaga tgatgatgac catgtggaca gccaggactc cattgactcg     480
aacgactctg atgatgtaga tgacactgat gattctcacc agtctgatga gtctcaccat     540
tctgatgaat ctgatgaact ggtcactgat tttcccacgg acctgccagc aaccgaagtt     600
ttcactccag ttgtccccac agtagacaca tatgatggcc gaggtgatag tgtggtttat     660
ggactgaggt caaaatctaa gaagtttcgc agacctgaca tccagtaccc tgatgctaca     720
gacgaggaca tcacctcaca catggaaagc gaggagttga atggtgcata caaggccatc     780
cccgttgccc aggacctgaa cgcgccttct gattgggaca gccgtgggaa ggacagttat     840
gaaacgagtc agctggatga ccagagtgct gaaacccaca gccacaagca gtccagatta     900
tataagcgga agccaatga tgagagcaat gagcattccg atgtgattga tagtcaggaa     960
ctttccaaag tcagccgtga attccacagc catgaatttc acagccatga agatatgctg    1020
gttgtagacc ccaaaagtaa ggaagaagat aaacacctga aatttcgtat ttctcatgaa    1080
ttagatagtg catcttctga ggtcaattaa aaggagaaaa aatacaattt ctcactttgc    1140
atttagtcaa aagaaaaaat gctttatagc aaaatgaaag agaacatgaa atgcttcttt    1200
```

-continued

```
ctcagtttat tggttgaatg tgtatctatt tgagtctgga ataaactaat gtgtttgata    1260
attagtttag tttgtggctt catggaaact ccctgtaaac taaaagcttc agggttatgt    1320
ctatgttcat tctatagaag aaatgcaaac tatcactgta ttttaatatt tgttattctc    1380
tcatgaatag aaatttatgt agaagcaaac aaaatacttt tacccactta aaaagagaat    1440
ataacatttt atgtcactat aatcttttgt ttttttaagtt agtgtatatt tgttgtgat    1500 tatcttttg tggtgtgaat aaatcttta tcttgaatgt aataagaatt tggtggtgtc    1560
aattgcttat ttgttttccc acggttgtcc agcaattaat aaaacataac ctttttact    1620 gcctaaaaaa aaaaaaaaaa a    1641
```

<210> SEQ ID NO 3
<211> LENGTH: 742
<212> TYPE: PRT
<213> ORGANISM: Homo Sapiens

<400> SEQUENCE: 3

```
Met Asp Lys Phe Trp Trp His Ala Ala Trp Gly Leu Cys Leu Val Pro
  1               5                  10                  15

Leu Ser Leu Ala Gln Ile Asp Leu Asn Ile Thr Cys Arg Phe Ala Gly
             20                  25                  30

Val Phe His Val Glu Lys Asn Gly Arg Tyr Ser Ile Ser Arg Thr Glu
         35                  40                  45

Ala Ala Asp Leu Cys Lys Ala Phe Asn Ser Thr Leu Pro Thr Met Ala
     50                  55                  60

Gln Met Glu Lys Ala Leu Ser Ile Gly Phe Glu Thr Cys Arg Tyr Gly
 65                  70                  75                  80

Phe Ile Glu Gly His Val Val Ile Pro Arg Ile His Pro Asn Ser Ile
                 85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285
```

```
His Leu Ser Phe Ser Gly Ser Gly Ile Asp Asp Glu Asp Phe Ile
    290                 295                 300
Ser Ser Thr Ile Ser Thr Thr Pro Arg Ala Phe Asp His Thr Lys Gln
305                 310                 315                 320
Asn Gln Asp Trp Thr Gln Trp Asn Pro Ser His Ser Asn Pro Glu Val
                325                 330                 335
Leu Leu Gln Thr Thr Thr Arg Met Thr Asp Val Asp Arg Asn Gly Thr
            340                 345                 350
Thr Ala Tyr Glu Gly Asn Trp Asn Pro Glu Ala His Pro Leu Ile
        355                 360                 365
His His Glu His His Glu Glu Glu Thr Pro His Ser Thr Ser Thr
    370                 375                 380
Ile Gln Ala Thr Pro Ser Ser Thr Thr Glu Glu Thr Ala Thr Gln Lys
385                 390                 395                 400
Glu Gln Trp Phe Gly Asn Arg Trp His Glu Gly Tyr Arg Gln Thr Pro
                405                 410                 415
Lys Glu Asp Ser His Ser Thr Thr Gly Thr Ala Ala Ser Ala His
            420                 425                 430
Thr Ser His Pro Met Gln Gly Arg Thr Thr Pro Ser Pro Glu Asp Ser
        435                 440                 445
Ser Trp Thr Asp Phe Phe Asn Pro Ile Ser His Pro Met Gly Arg Gly
    450                 455                 460
His Gln Ala Gly Arg Arg Met Asp Met Asp Ser Ser His Ser Ile Thr
465                 470                 475                 480
Leu Gln Pro Thr Ala Asn Pro Asn Thr Gly Leu Val Glu Asp Leu Asp
                485                 490                 495
Arg Thr Gly Pro Leu Ser Met Thr Thr Gln Gln Ser Asn Ser Gln Ser
            500                 505                 510
Phe Ser Thr Ser His Glu Gly Leu Glu Glu Asp Lys Asp His Pro Thr
        515                 520                 525
Thr Ser Thr Leu Thr Ser Ser Asn Arg Asn Asp Val Thr Gly Gly Arg
    530                 535                 540
Arg Asp Pro Asn His Ser Glu Gly Ser Thr Thr Leu Leu Glu Gly Tyr
545                 550                 555                 560
Thr Ser His Tyr Pro His Thr Lys Glu Ser Arg Thr Phe Ile Pro Val
                565                 570                 575
Thr Ser Ala Lys Thr Gly Ser Phe Gly Val Thr Ala Val Thr Val Gly
            580                 585                 590
Asp Ser Asn Ser Asn Val Asn Arg Ser Leu Ser Gly Asp Gln Asp Thr
        595                 600                 605
Phe His Pro Ser Gly Gly Ser His Thr Thr His Gly Ser Glu Ser Asp
    610                 615                 620
Gly His Ser His Gly Ser Gln Glu Gly Gly Ala Asn Thr Thr Ser Gly
625                 630                 635                 640
Pro Ile Arg Thr Pro Gln Ile Pro Glu Trp Leu Ile Ile Leu Ala Ser
                645                 650                 655
Leu Leu Ala Leu Ala Leu Ile Leu Ala Val Cys Ile Ala Val Asn Ser
            660                 665                 670
Arg Arg Arg Cys Gly Gln Lys Lys Lys Leu Val Ile Asn Ser Gly Asn
    675                 680                 685
Gly Ala Val Glu Asp Arg Lys Pro Ser Gly Leu Asn Gly Glu Ala Ser
690                 695                 700
Lys Ser Gln Glu Met Val His Leu Val Asn Lys Glu Ser Ser Glu Thr
```

| | | | | |
|---|---|---|---|---|
| 705 | 710 | 715 | 720 | |

Pro Asp Gln Phe Met Thr Ala Asp Glu Thr Arg Asn Leu Gln Asn Val
                  725                  730                  735

Asp Met Lys Ile Gly Val
            740

<210> SEQ ID NO 4
<211> LENGTH: 5748
<212> TYPE: DNA
<213> ORGANISM: Homo Sapiens

<400> SEQUENCE: 4

| | | | | | |
|---|---|---|---|---|---|
| gagaagaaag | ccagtgcgtc | tctgggcgca | ggggccagtg | gggctcggag | gcacaggcac | 60 |
| cccgcgacac | tccaggttcc | ccgacccacg | tccctggcag | ccccgattat | ttacagcctc | 120 |
| agcagagcac | ggggcggggg | cagaggggcc | cgcccgggag | ggctgctact | tcttaaaacc | 180 |
| tctgcgggct | gcttagtcac | agcccccctt | gcttgggtgt | gtccttcgct | cgctccctcc | 240 |
| ctccgtctta | ggtcactgtt | ttcaacctcg | aataaaaact | gcagccaact | tccgaggcag | 300 |
| cctcattgcc | cagcggaccc | cagcctctgc | caggttcggt | ccgccatcct | cgtcccgtcc | 360 |
| tccgccggcc | cctgccccgc | gcccaggat | cctccagctc | ctttcgcccg | cgccctccgt | 420 |
| tcgctccgga | caccatggac | aagttttggt | ggcacgcagc | ctgggactc | tgcctcgtgc | 480 |
| cgctgagcct | ggcgcagatc | gatttgaata | taacctgccg | ctttgcaggt | gtattccacg | 540 |
| tggagaaaaa | tggtcgctac | agcatctctc | ggacggaggc | cgctgaccta | tgcaaggctt | 600 |
| tcaatagcac | cttgcccaca | atggcccaga | tggagaaagc | tctgagcatc | ggatttgaga | 660 |
| cctgcaggta | tgggttcata | gaagggcacg | tggtgattcc | ccggatccac | cccaactcca | 720 |
| tctgtgcagc | aaacaacaca | ggggtgtaca | tcctcacatc | caacacctcc | cagtatgaca | 780 |
| catattgctt | caatgcttca | gctccacctg | aagaagattg | tacatcagtc | acagacctgc | 840 |
| ccaatgcctt | tgatggacca | attaccataa | ctattgttaa | ccgtgatggc | acccgctatg | 900 |
| tccagaaagg | agaatacaga | acgaatcctg | aagacatcta | ccccagcaac | cctactgatg | 960 |
| atgacgtgag | cagcggctcc | tccagtgaaa | ggagcagcac | ttcaggaggt | tacatctttt | 1020 |
| acaccttttc | tactgtacac | cccatcccag | acgaagacag | tccctggatc | accgacagca | 1080 |
| cagacagaat | ccctgctacc | actttgatga | gcactagtgc | tacagcaact | gagacagcaa | 1140 |
| ccaagaggca | agaaacctgg | gattggtttt | catggttgtt | tctaccatca | gagtcaaaga | 1200 |
| atcatcttca | cacaacaaca | caaatggctg | gtacgtcttc | aaataccatc | tcagcaggct | 1260 |
| gggagccaaa | tgaagaaaat | gaagatgaaa | gagacagaca | cctcagtttt | tctggatcag | 1320 |
| gcattgatga | tgatgaagat | tttatctcca | gcaccatttc | aaccacacca | cgggcttttg | 1380 |
| accacacaaa | acagaaccag | gactggaccc | agtggaaccc | aagccattca | aatccggaag | 1440 |
| tgctacttca | gacaaccaca | aggatgactg | atgtagacag | aaatggcacc | actgcttatg | 1500 |
| aaggaaactg | gaacccagaa | gcacaccctc | ccctcattca | ccatgagcat | catgaggaag | 1560 |
| aagagacccc | acattctaca | agcacaatcc | aggcaactcc | tagtagtaca | acggaagaaa | 1620 |
| cagctaccca | gaaggaacag | tggtttggca | acagatggca | tgagggatat | cgccaaacac | 1680 |
| ccaaagaaga | ctcccattcg | acaacaggga | cagctgcagc | ctcagctcat | accagccatc | 1740 |
| caatgcaagg | aaggacaaca | ccaagcccag | aggacagttc | ctggactgat | ttcttcaacc | 1800 |
| caatctcaca | ccccatggga | cgaggtcatc | aagcaggaag | aaggatggat | atggactcca | 1860 |
| gtcatagtat | aacgcttcag | cctactgcaa | atccaaacac | aggtttggtg | gaagatttgg | 1920 |

```
acaggacagg acctctttca atgacaacgc agcagagtaa ttctcagagc ttctctacat    1980
cacatgaagg cttggaagaa gataaagacc atccaacaac ttctactctg acatcaagca    2040
ataggaatga tgtcacaggt ggaagaagag acccaaatca ttctgaaggc tcaactactt    2100
tactggaagg ttatacctct cattacccac acacgaagga aagcaggacc ttcatcccag    2160
tgacctcagc taagactggg tcctttggag ttactgcagt tactgttgga gattccaact    2220
ctaatgtcaa tcgttcctta tcaggagacc aagacacatt ccaccccagt gggggtccc     2280 ataccactca tggatctgaa tcagatggac actcacatgg gagtcaagaa ggtggagcaa    2340
acacaacctc tggtcctata aggacacccc aaattccaga atggctgatc atcttggcat    2400
ccctcttggc cttggctttg attcttgcag tttgcattgc agtcaacagt cgaagaaggt    2460
gtgggcagaa gaaaaagcta gtgatcaaca gtggcaatgg agctgtggag acagaaagc     2520 caagtggact caacggagag gccagcaagt ctcaggaaat ggtgcatttg gtgaacaagg    2580
agtcgtcaga aactccagac cagtttatga cagctgatga gacaaggaac ctgcagaatg    2640
tggacatgaa gattggggtg taacacctac accattatct tggaaagaaa caaccgttgg    2700
aaacataacc attacaggga gctgggacac ttaacagatg caatgtgcta ctgattgttt    2760
cattgcgaat ctttttttagc ataaaatttt ctactcttt tgtttttttgt gttttgttct    2820 ttaaagtcag gtccaatttg taaaaacagc attgctttct gaaattaggg cccaattaat    2880
aatcagcaag aatttgatcg ttccagttcc cacttggagg cctttcatcc ctcgggtgtg    2940
ctatggatgg cttctaacaa aaactacaca tatgtattcc tgatcgccaa cctttccccc    3000
accagctaag gacatttccc agggttaata gggcctggtc cctgggagga aatttgaatg    3060
ggtccatttt gcccttccat agcctaatcc ctgggcattg cttttccactg aggttggggg    3120 ttggggtgta ctagttacac atcttcaaca gacccctct agaaattttt cagatgcttc     3180
tgggagacac ccaaagggtg aagctattta tctgtagtaa actatttatc tgtgtttttg    3240
aaatattaaa ccctggatca gtcctttgat cagtataatt ttttaaagtt actttgtcag    3300
aggcacaaaa gggtttaaac tgattcataa taaatatctg tacttcttcg atcttcacct    3360
tttgtgctgt gattcttcag tttctaaacc agcactgtct gggtccctac aatgtatcag    3420
gaagagctga gaatggtaag gagactcttc taagtcttca tctcagagac cctgagttcc    3480
cactcagacc cactcagcca aatctcatgg aagaccaagg agggcagcac tgtttttgtt    3540
ttttgttttt tgtttttttt ttttgacact gtccaaaggt tttccatcct gtcctggaat    3600
cagagttgga agctgaggag cttcagcctc tttatggtt taatggccac ctgttctctc     3660
ctgtgaaagg ctttgcaaag tcacattaag tttgcatgac ctgttatccc tgggcccta     3720 tttcatagag gctggcccta ttagtgattt ccaaaaacaa tatggaagtg ccttttgatg    3780
tcttacaata agagaagaag ccaatggaaa tgaaagagat tggcaaaggg gaaggatgat    3840
gccatgtaga tcctgtttga catttttatg gctgtatttg taaacttaaa cacaccagtg    3900
tctgttcttg atgcagttgc tatttaggat gagttaagtg cctggggagt ccctcaaaag    3960
gttaaaggga ttcccatcat tggaatctta tcaccagata ggcaagttta tgaccaaaca    4020
agagagtact ggctttatcc tctaacctca tattttctcc cacttggcaa gtcctttgtg    4080
gcatttattc atcagtcagg gtgtccgatt ggtcctagaa cttccaaagg ctgcttgtca    4140
tagaagccat tgcatctata aagcaacggc tcctgttaaa tggtatctcc tttctgaggc    4200
tcctactaaa agtcatttgt tacctaaact tatgtgctta acaggcaatg cttctcagac    4260
```

| | | | | |
|---|---|---|---|---|
| cacaaagcag | aaagaagaag | aaaagctcct | gactaaatca | gggctgggct tagacagagt | 4320 |
| tgatctgtag | aatatcttta | aaggagagat | gtcaactttc | tgcactattc ccagcctctg | 4380 |
| ctcctccctg | tctaccctct | ccctccctc | tctccctcca | cttcacccca caatcttgaa | 4440 |
| aaacttcctt | tctcttctgt | gaacatcatt | ggccagatcc | attttcagtg gtctggattt | 4500 |
| cttttatt | tctttcaac | ttgaaagaaa | ctggacatta | ggccactatg tgttgttact | 4560 |
| gccactagtg | ttcaagtgcc | tcttgttttc | ccagagattt | cctgggtctg ccagaggccc | 4620 |
| agacaggctc | actcaagctc | tttaactgaa | aagcaacaag | ccactccagg acaaggttca | 4680 |
| aaatggttac | aacagcctct | acctgtcgcc | ccagggagaa | aggggtagtg atacaagtct | 4740 |
| catagccaga | gatggttttc | cactccttct | agatattccc | aaaagaggc tgagacagga | 4800 |
| ggttatttc | aattttattt | tggaattaaa | tactttttc | cctttattac tgttgtagtc | 4860 |
| cctcacttgg | atatacctct | gttttcacga | tagaaataag | ggaggtctag agcttctatt | 4920 |
| ccttggccat | tgtcaacgga | gagctggcca | agtcttcaca | acccttgca acattgcctg | 4980 |
| aagtttatgg | aataagatgt | attctcactc | ccttgatctc | aagggcgtaa ctctggaagc | 5040 |
| acagcttgac | tacacgtcat | ttttaccaat | gattttcagg | tgacctgggc taagtcattt | 5100 |
| aaactgggtc | tttataaaag | taaaaggcca | acatttaatt | attttgcaaa gcaacctaag | 5160 |
| agctaaagat | gtaattttc | ttgcaattgt | aaatcttttg | tgtctcctga agacttccct | 5220 |
| taaaattagc | tctgagtgaa | aaatcaaaag | agacaaaaga | catcttcgaa tccatatttc | 5280 |
| aagcctggta | gaattggctt | ttctagcaga | acctttccaa | aagttttata ttgagattca | 5340 |
| taacaacacc | aagaattgat | tttgtagcca | acattcattc | aatactgtta tatcagagga | 5400 |
| gtaggagaga | ggaaacattt | gacttatctg | gaaaagcaaa | atgtacttaa gaataagaat | 5460 |
| aacatggtcc | attcaccttt | atgttataga | tatgtctttg | tgtaaatcat ttgttttgag | 5520 |
| ttttcaaaga | atagcccatt | gttcattctt | gtgctgtaca | atgaccactg ttattgttac | 5580 |
| tttgactttt | cagagcacac | ccttcctctg | gtttttgtat | atttattgat ggatcaataa | 5640 |
| taatgaggaa | agcatgatat | gtatattgct | gagttgaaag | cacttattgg aaaatattaa | 5700 |
| aaggctaaca | ttaaaagact | aaaggaaaca | gaaaaaaaaa | aaaaaaaa | 5748 |

<210> SEQ ID NO 5
<211> LENGTH: 1049
<212> TYPE: PRT
<213> ORGANISM: Homo Sapiens

<400> SEQUENCE: 5

```
Met Gly Ser Arg Thr Pro Glu Ser Pro Leu His Ala Val Gln Leu Arg
1               5                   10                  15

Trp Gly Pro Arg Arg Pro Pro Leu Leu Pro Leu Leu Leu Leu Leu Leu
            20                  25                  30

Leu Pro Pro Pro Arg Val Gly Gly Phe Asn Leu Asp Ala Glu Ala
        35                  40                  45

Pro Ala Val Leu Ser Gly Pro Gly Ser Phe Phe Gly Phe Ser Val
    50                  55                  60

Glu Phe Tyr Arg Pro Gly Thr Asp Gly Val Ser Val Leu Val Gly Ala
65                  70                  75                  80

Pro Lys Ala Asn Thr Ser Gln Pro Gly Val Leu Gln Gly Gly Ala Val
                85                  90                  95

Tyr Leu Cys Pro Trp Gly Ala Ser Pro Thr Gln Cys Thr Pro Ile Glu
            100                 105                 110
```

```
Phe Asp Ser Lys Gly Ser Arg Leu Glu Ser Ser Leu Ser Ser Ser
            115                 120                 125
Glu Gly Glu Glu Pro Val Glu Tyr Lys Ser Leu Gln Trp Phe Gly Ala
130                 135                 140
Thr Val Arg Ala His Gly Ser Ser Ile Leu Ala Cys Ala Pro Leu Tyr
145                 150                 155                 160
Ser Trp Arg Thr Glu Lys Glu Pro Leu Ser Asp Pro Val Gly Thr Cys
                165                 170                 175
Tyr Leu Ser Thr Asp Asn Phe Thr Arg Ile Leu Glu Tyr Ala Pro Cys
            180                 185                 190
Arg Ser Asp Phe Ser Trp Ala Ala Gly Gln Gly Tyr Cys Gln Gly Gly
        195                 200                 205
Phe Ser Ala Glu Phe Thr Lys Thr Gly Arg Val Val Leu Gly Gly Pro
    210                 215                 220
Gly Ser Tyr Phe Trp Gln Gly Gln Ile Leu Ser Ala Thr Gln Glu Gln
225                 230                 235                 240
Ile Ala Glu Ser Tyr Tyr Pro Glu Tyr Leu Ile Asn Leu Val Gln Gly
                245                 250                 255
Gln Leu Gln Thr Arg Gln Ala Ser Ser Ile Tyr Asp Asp Ser Tyr Leu
            260                 265                 270
Gly Tyr Ser Val Ala Val Gly Glu Phe Ser Gly Asp Asp Thr Glu Asp
        275                 280                 285
Phe Val Ala Gly Val Pro Lys Gly Asn Leu Thr Tyr Gly Tyr Val Thr
    290                 295                 300
Ile Leu Asn Gly Ser Asp Ile Arg Ser Leu Tyr Asn Phe Ser Gly Glu
305                 310                 315                 320
Gln Met Ala Ser Tyr Phe Gly Tyr Ala Val Ala Ala Thr Asp Val Asn
                325                 330                 335
Gly Asp Gly Leu Asp Asp Leu Leu Val Gly Ala Pro Leu Leu Met Asp
            340                 345                 350
Arg Thr Pro Asp Gly Arg Pro Gln Glu Val Gly Arg Val Tyr Val Tyr
        355                 360                 365
Leu Gln His Pro Ala Gly Ile Glu Pro Thr Pro Thr Leu Thr Leu Thr
    370                 375                 380
Gly His Asp Glu Phe Gly Arg Phe Gly Ser Ser Leu Thr Pro Leu Gly
385                 390                 395                 400
Asp Leu Asp Gln Asp Gly Tyr Asn Asp Val Ala Ile Gly Ala Pro Phe
                405                 410                 415
Gly Gly Glu Thr Gln Gln Gly Val Val Phe Val Phe Pro Gly Gly Pro
            420                 425                 430
Gly Gly Leu Gly Ser Lys Pro Ser Gln Val Leu Gln Pro Leu Trp Ala
        435                 440                 445
Ala Ser His Thr Pro Asp Phe Phe Gly Ser Ala Leu Arg Gly Gly Arg
    450                 455                 460
Asp Leu Asp Gly Asn Gly Tyr Pro Asp Leu Ile Val Gly Ser Phe Gly
465                 470                 475                 480
Val Asp Lys Ala Val Val Tyr Arg Gly Arg Pro Ile Val Ser Ala Ser
                485                 490                 495
Ala Ser Leu Thr Ile Phe Pro Ala Met Phe Asn Pro Glu Glu Arg Ser
            500                 505                 510
Cys Ser Leu Glu Gly Asn Pro Val Ala Cys Ile Asn Leu Ser Phe Cys
        515                 520                 525
Leu Asn Ala Ser Gly Lys His Val Ala Asp Ser Ile Gly Phe Thr Val
```

-continued

```
            530                 535                 540
Glu Leu Gln Leu Asp Trp Gln Lys Gln Lys Gly Gly Val Arg Arg Ala
545                 550                 555                 560

Leu Phe Leu Ala Ser Arg Gln Ala Thr Leu Thr Gln Thr Leu Leu Ile
                565                 570                 575

Gln Asn Gly Ala Arg Glu Asp Cys Arg Glu Met Lys Ile Tyr Leu Arg
                580                 585                 590

Asn Glu Ser Glu Phe Arg Asp Lys Leu Ser Pro Ile His Ile Ala Leu
                595                 600                 605

Asn Phe Ser Leu Asp Pro Gln Ala Pro Val Asp Ser His Gly Leu Arg
                610                 615                 620

Pro Ala Leu His Tyr Gln Ser Lys Ser Arg Ile Glu Asp Lys Ala Gln
625                 630                 635                 640

Ile Leu Leu Asp Cys Gly Glu Asp Asn Ile Cys Val Pro Asp Leu Gln
                645                 650                 655

Leu Glu Val Phe Gly Glu Gln Asn His Val Tyr Leu Gly Asp Lys Asn
                660                 665                 670

Ala Leu Asn Leu Thr Phe His Ala Gln Asn Val Gly Glu Gly Gly Ala
                675                 680                 685

Tyr Glu Ala Glu Leu Arg Val Thr Ala Pro Pro Glu Ala Glu Tyr Ser
690                 695                 700

Gly Leu Val Arg His Pro Gly Asn Phe Ser Ser Leu Ser Cys Asp Tyr
705                 710                 715                 720

Phe Ala Val Asn Gln Ser Arg Leu Leu Val Cys Asp Leu Gly Asn Pro
                725                 730                 735

Met Lys Ala Gly Ala Ser Leu Trp Gly Gly Leu Arg Phe Thr Val Pro
                740                 745                 750

His Leu Arg Asp Thr Lys Lys Thr Ile Gln Phe Asp Phe Gln Ile Leu
                755                 760                 765

Ser Lys Asn Leu Asn Asn Ser Gln Ser Asp Val Val Ser Phe Arg Leu
                770                 775                 780

Ser Val Glu Ala Gln Ala Gln Val Thr Leu Asn Gly Val Ser Lys Pro
785                 790                 795                 800

Glu Ala Val Leu Phe Pro Val Ser Asp Trp His Pro Arg Asp Gln Pro
                805                 810                 815

Gln Lys Glu Glu Asp Leu Gly Pro Ala Val His His Val Tyr Glu Leu
                820                 825                 830

Ile Asn Gln Gly Pro Ser Ser Ile Ser Gln Gly Val Leu Glu Leu Ser
                835                 840                 845

Cys Pro Gln Ala Leu Glu Gly Gln Gln Leu Leu Tyr Val Thr Arg Val
850                 855                 860

Thr Gly Leu Asn Cys Thr Thr Asn His Pro Ile Asn Pro Lys Gly Leu
865                 870                 875                 880

Glu Leu Asp Pro Glu Gly Ser Leu His His Gln Gln Lys Arg Glu Ala
                885                 890                 895

Pro Ser Arg Ser Ser Ala Ser Ser Gly Pro Gln Ile Leu Lys Cys Pro
                900                 905                 910

Glu Ala Glu Cys Phe Arg Leu Arg Cys Glu Leu Gly Pro Leu His Gln
                915                 920                 925

Gln Glu Ser Gln Ser Leu Gln Leu His Phe Arg Val Trp Ala Lys Thr
                930                 935                 940

Phe Leu Gln Arg Glu His Gln Pro Phe Ser Leu Gln Cys Glu Ala Val
945                 950                 955                 960
```

Tyr Lys Ala Leu Lys Met Pro Tyr Arg Ile Leu Pro Arg Gln Leu Pro
            965                 970                 975

Gln Lys Glu Arg Gln Val Ala Thr Ala Val Gln Trp Thr Lys Ala Glu
        980                 985                 990

Gly Ser Tyr Gly Val Pro Leu Trp Ile Ile Ile Leu Ala Ile Leu Phe
        995                1000                1005

Gly Leu Leu Leu Leu Gly Leu Leu Ile Tyr Ile Leu Tyr Lys Leu
    1010                1015                1020

Gly Phe Phe Lys Arg Ser Leu Pro Tyr Gly Thr Ala Met Glu Lys
    1025                1030                1035

Ala Gln Leu Lys Pro Pro Ala Thr Ser Asp Ala
    1040                1045

<210> SEQ ID NO 6
<211> LENGTH: 4267
<212> TYPE: DNA
<213> ORGANISM: Homo Sapiens

<400> SEQUENCE: 6
attcgcctct gggaggttta ggaagcggct ccgggtcggt ggccccagga cagggaagag    60
cgggcgctat ggggagccgg acgccagagt cccctctcca cgccgtgcag ctgcgctggg   120
gcccccggcg ccgaccccg ctgctgccgc tgctgttgct gctgctgccg ccgcacccca   180
gggtcggggg cttcaactta gacgcggagg ccccagcagt actctcgggg ccccgggct   240 ccttcttcgg attctcagtg gagttttacc ggccgggaac agacgggtc agtgtgctgg   300 tgggagcacc caaggctaat accagccagc caggagtgct gcagggtggt gctgtctacc   360
tctgtccttg gggtgccagc cccacacagt gcaccccat tgaatttgac agcaaaggct   420
ctcggctcct ggagtcctca ctgtccagct cagagggaga ggagcctgtg gagtacaagt   480
ccttgcagtg gttcggggca acagttcgag cccatggctc ctccatcttg gcatgcgctc   540
cactgtacag ctggcgcaca gagaaggagc cactgagcga ccccgtgggc acctgctacc   600
tctccacaga taacttcacc cgaattctgg agtatgcacc ctgccgctca gatttcagct   660
gggcagcagg acagggttac tgccaaggag gcttcagtgc cgagttcacc aagactggcc   720
gtgtggtttt aggtggacca ggaagctatt tctggcaagg ccagatcctg tctgccactc   780
aggagcagat tgcagaatct tattaccccg agtacctgat caacctggtt cagggggcagc   840 tgcagactcg ccaggccagt tccatctatg atgacagcta cctaggatac tctgtggctg   900
ttggtgaatt cagtggtgat gacacagaag actttgttgc tggtgtgccc aaagggaacc   960
tcacttacgg ctatgtcacc atccttaatg gctcagacat tcgatccctc tacaacttct  1020
caggggaaca gatggcctcc tactttggct atgcagtggc cgccacagac gtcaatgggg  1080
acgggctgga tgacttgctg gtgggggcac ccctgctcat ggatcggacc cctgacgggc  1140
ggcctcagga ggtgggcagg gtctacgtct acctgcagca cccagccggc ataggagccca  1200 cgcccaccct tacctcact ggccatgatg agtttggccg atttggcagc tccttgaccc  1260
ccctggggga cctggaccag gatggctaca atgatgtggc catcggggct ccctttggtg  1320
gggagaccca gcaggagta tgtttgtat ttcctggggg cccaggaggg ctgggctcta  1380
agccttccca ggttctgcag ccctgtggg cagccagcca caccccagac ttctttggct  1440
ctgcccttcg aggaggccga gacctggatg caatggata tcctgatctg attgtggggt  1500
cctttggtgt ggacaaggct gtggtataca ggggccgccc catcgtgtcc gctagtgcct  1560

```
ccctcaccat cttccccgcc atgttcaacc cagaggagcg gagctgcagc ttagagggga    1620
accctgtggc ctgcatcaac cttagcttct gcctcaatgc ttctggaaaa cacgttgctg    1680
actccattgg tttcacagtg gaacttcagc tggactggca gaagcagaag ggaggggtac    1740
ggcgggcact gttcctggcc tccaggcagg caaccctgac ccagaccctg ctcatccaga    1800
atggggctcg agaggattgc agagagatga agatctacct caggaacgag tcagaatttc    1860
gagacaaact ctcgccgatt cacatcgctc tcaacttctc cttggacccc caagccccag    1920
tggacagcca cggcctcagg ccagccctac attatcagag caagagccgg atagaggaca    1980
aggctcagat cttgctggac tgtggagaag acaacatctg tgtgcctgac ctgcagctgg    2040
aagtgtttgg ggagcagaac catgtgtacc tgggtgacaa gaatgccctg aacctcactt    2100
tccatgccca gaatgtgggt gagggtggcg cctatgaggc tgagcttcgg gtcaccgccc    2160
ctccagaggc tgagtactca ggactcgtca gacacccagg gaacttctcc agcctgagct    2220
gtgactactt tgccgtgaac cagagccgcc tgctggtgtg tgacctgggc aaccccatga    2280
aggcaggagc cagtctgtgg ggtggccttc ggtttacagt ccctcatctc cgggacacta    2340
agaaaaccat ccagtttgac ttccagatcc tcagcaagaa tctcaacaac tcgcaaagcg    2400
acgtggtttc ctttcggctc tccgtggagg ctcaggccca ggtcaccctg aacggtgtct    2460
ccaagcctga ggcagtgcta ttcccagtaa gcgactggca tccccgagac cagcctcaga    2520
aggaggagga cctgggacct gctgtccacc atgtctatga gctcatcaac caaggcccca    2580
gctccattag ccagggtgtg ctggaactca gctgtcccca ggctctggaa ggtcagcagc    2640
tcctatatgt gaccagagtt acgggactca actgcaccac caatcacccc attaacccaa    2700
agggcctgga gttggatccc gagggttccc tgcaccacca gcaaaaacgg gaagctccaa    2760
gccgcagctc tgcttcctcg ggacctcaga tcctgaaatg cccggaggct gagtgtttca    2820
ggctgcgctg tgagctcggg cccctgcacc aacaagagag ccaaagtctg cagttgcatt    2880
tccgagtctg ggccaagact ttcttgcagc gggagcacca gccatttagc ctgcagtgtg    2940
aggctgtgta caaagccctg aagatgccct accgaatcct gcctcggcag ctgccccaaa    3000
aagagcgtca ggtggccaca gctgtgcaat ggaccaaggc agaaggcagc tatggcgtcc    3060
cactgtggat catcatccta gccatcctgt ttggcctcct gctcctaggt ctactcatct    3120
acatcctcta caagcttgga ttcttcaaac gctccctccc atatggcacc gccatggaaa    3180
aagctcagct caagcctcca gccacctctg atgcctgagt cctcccaatt tcagactccc    3240
attcctgaag aaccagtccc cccaccctca ttctactgaa aaggaggggt ctgggtactt    3300
cttgaaggtg ctgacggcca gggagaagct cctctcccca gcccagagac atacttgaag    3360
ggccagagcc aggggggtga ggagctgggg atccctcccc ccatgcact gtgaaggacc    3420 cttgtttaca catccctct tcatggatgg gggaactcag atccagggac agaggcccca    3480
gcctccctga agcctttgca ttttggagag tttcctgaaa caacttggaa agataactag    3540
gaaatccatt cacagttctt tgggccagac atgccacaag acttcctgt ccagctccaa    3600 cctgcaaaga tctgtcctca gccttgccag agatccaaaa gaagcccca gctaagaacc    3660 tggaacttgg ggagttaaga cctggcagct ctggacagcc ccaccctggt gggccaacaa    3720
agaacactaa ctatgcatgg tgccccagga ccagctcagg acagatgcca cacaaggata    3780
gatgctggcc cagggcccag agcccagctc aagggaat cagaactcaa atggggccag    3840
atccagcctg ggtctggag ttgatctgga acccagactc agacattggc acctaatcca    3900
ggcagatcca ggactatatt tgggcctgct ccagacctga tcctggaggc ccagttcacc    3960
```

-continued

```
ctgatttagg agaagccagg aatttcccag gaccctgaag gggccatgat ggcaacagat    4020
ctggaacctc agcctggcca gacacaggcc ctccctgttc cccagagaaa ggggagccca    4080
ctgtcctggg cctgcagaat ttgggttctg cctgccagct gcactgatgc tgcccctcat    4140
ctctctgccc aacccttccc tcaccttggc accagacacc caggacttat ttaaactctg    4200
ttgcaagtgc aataaatctg acccagtgcc cccactgacc agaactagaa aaaaaaaaa    4260 aaaaaaa                                                              4267
```

<210> SEQ ID NO 7
<211> LENGTH: 798
<212> TYPE: PRT
<213> ORGANISM: Homo Sapiens

<400> SEQUENCE: 7

```
Met Asn Leu Gln Pro Ile Phe Trp Ile Gly Leu Ile Ser Ser Val Cys
 1               5                  10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
```

```
                305                 310                 315                 320
        His Leu Val Gln Lys Leu Ser Glu Asn Asn Ile Gln Thr Ile Phe Ala
                        325                 330                 335

Val Thr Glu Glu Phe Gln Pro Val Tyr Lys Glu Leu Lys Asn Leu Ile
                        340                 345                 350

Pro Lys Ser Ala Val Gly Thr Leu Ser Ala Asn Ser Ser Asn Val Ile
                        355                 360                 365

Gln Leu Ile Ile Asp Ala Tyr Asn Ser Leu Ser Ser Glu Val Ile Leu
                        370                 375                 380

Glu Asn Gly Lys Leu Ser Glu Gly Val Thr Ile Ser Tyr Lys Ser Tyr
        385                 390                 395                 400

Cys Lys Asn Gly Val Asn Gly Thr Gly Glu Asn Gly Arg Lys Cys Ser
                        405                 410                 415

Asn Ile Ser Ile Gly Asp Glu Val Gln Phe Glu Ile Ser Ile Thr Ser
                        420                 425                 430

Asn Lys Cys Pro Lys Lys Asp Ser Asp Ser Phe Lys Ile Arg Pro Leu
                        435                 440                 445

Gly Phe Thr Glu Glu Val Glu Val Ile Leu Gln Tyr Ile Cys Glu Cys
                        450                 455                 460

Glu Cys Gln Ser Glu Gly Ile Pro Glu Ser Pro Lys Cys His Glu Gly
        465                 470                 475                 480

Asn Gly Thr Phe Glu Cys Gly Ala Cys Arg Cys Asn Glu Gly Arg Val
                        485                 490                 495

Gly Arg His Cys Glu Cys Ser Thr Asp Glu Val Asn Ser Glu Asp Met
                        500                 505                 510

Asp Ala Tyr Cys Arg Lys Glu Asn Ser Ser Glu Ile Cys Ser Asn Asn
                        515                 520                 525

Gly Glu Cys Val Cys Gly Gln Cys Val Cys Arg Lys Arg Asp Asn Thr
                        530                 535                 540

Asn Glu Ile Tyr Ser Gly Lys Phe Cys Glu Cys Asp Asn Phe Asn Cys
        545                 550                 555                 560

Asp Arg Ser Asn Gly Leu Ile Cys Gly Gly Asn Gly Val Cys Lys Cys
                        565                 570                 575

Arg Val Cys Glu Cys Asn Pro Asn Tyr Thr Gly Ser Ala Cys Asp Cys
                        580                 585                 590

Ser Leu Asp Thr Ser Thr Cys Glu Ala Ser Asn Gly Gln Ile Cys Asn
                        595                 600                 605

Gly Arg Gly Ile Cys Glu Cys Gly Val Cys Lys Cys Thr Asp Pro Lys
                        610                 615                 620

Phe Gln Gly Gln Thr Cys Glu Met Cys Gln Thr Cys Leu Gly Val Cys
        625                 630                 635                 640

Ala Glu His Lys Glu Cys Val Gln Cys Arg Ala Phe Asn Lys Gly Glu
                        645                 650                 655

Lys Lys Asp Thr Cys Thr Gln Glu Cys Ser Tyr Phe Asn Ile Thr Lys
                        660                 665                 670

Val Glu Ser Arg Asp Lys Leu Pro Gln Pro Val Gln Pro Asp Pro Val
                        675                 680                 685

Ser His Cys Lys Glu Lys Asp Val Asp Asp Cys Trp Phe Tyr Phe Thr
                        690                 695                 700

Tyr Ser Val Asn Gly Asn Asn Glu Val Met Val His Val Val Glu Asn
        705                 710                 715                 720

Pro Glu Cys Pro Thr Gly Pro Asp Ile Ile Pro Ile Val Ala Gly Val
                        725                 730                 735
```

```
Val Ala Gly Ile Val Leu Ile Gly Leu Ala Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 8
<211> LENGTH: 3879
<212> TYPE: DNA
<213> ORGANISM: Homo Sapiens

<400> SEQUENCE: 8
```

| | | | | | |
|---|---|---|---|---|---|
| atcagacgcg | cagaggaggc | ggggccgcgg | ctggtttcct | gccgggggc | ggctctgggc | 60 |
| cgccgagtcc | cctcctcccg | cccctgagga | ggaggagccg | ccgccacccg | ccgcgcccga | 120 |
| cacccgggag | gccccgccag | cccgcgggag | aggcccagcg | ggagtcgcgg | aacagcaggc | 180 |
| ccgagcccac | cgcgccgggc | cccggacgcc | gcgcggaaaa | gatgaattta | caaccaattt | 240 |
| tctggattgg | actgatcagt | tcagtttgct | gtgtgtttgc | tcaaacagat | gaaaatagat | 300 |
| gtttaaaagc | aaatgccaaa | tcatgtggag | aatgtataca | agcagggcca | aattgtgggt | 360 |
| ggtgcacaaa | ttcaacattt | ttacaggaag | gaatgcctac | ttctgcacga | tgtgatgatt | 420 |
| tagaagcctt | aaaaagaag | ggttgccctc | cagatgacta | gaaaatccc | agaggctcca | 480 |
| aagatataaa | gaaaataaa | aatgtaacca | accgtagcaa | aggaacagca | gagaagctca | 540 |
| agccagagga | tattactcag | atccaaccac | agcagttggt | tttgcgatta | agatcagggg | 600 |
| agccacagac | atttacatta | aaattcaaga | gagctgaaga | ctatcccatt | gacctctact | 660 |
| accttatgga | cctgtcttac | tcaatgaaag | acgatttgga | gaatgtaaaa | agtcttggaa | 720 |
| cagatctgat | gaatgaaatg | aggaggatta | cttcggactt | cagaattgga | tttggctcat | 780 |
| ttgtggaaaa | gactgtgatg | ccttacatta | gcacaacacc | agctaagctc | aggaaccctt | 840 |
| gcacaagtga | acagaactgc | accagcccat | ttagctacaa | aaatgtgctc | agtcttacta | 900 |
| ataaggaga | agtatttaat | gaacttgttg | gaaaacagcg | catatctgga | aatttggatt | 960 |
| ctccagaagg | tggtttcgat | gccatcatgc | aagttcagt | ttgtggatca | ctgattggct | 1020 |
| ggaggaatgt | tacacggctg | ctggtgtttt | ccacagatgc | cgggtttcac | tttgctggag | 1080 |
| atgggaaact | tggtggcatt | gttttaccaa | atgatggaca | atgtcacctg | gaaaataata | 1140 |
| tgtacacaat | gagccattat | tatgattatc | cttctattgc | tcaccttgtc | cagaaactga | 1200 |
| gtgaaaataa | tattcagaca | attttgcag | ttactgaaga | atttcagcct | gtttacaagg | 1260 |
| agctgaaaaa | cttgatccct | aagtcagcag | taggaacatt | atctgcaaat | tctagcaatg | 1320 |
| taattcagtt | gatcattgat | gcatacaatt | cccttttcctc | agaagtcatt | ttggaaaacg | 1380 |
| gcaaattgtc | agaaggcgta | acaataagtt | acaaatctta | ctgcaagaac | ggggtgaatg | 1440 |
| gaacagggga | aaatggaaga | aaatgttcca | atatttccat | ggagatgag | gttcaatttg | 1500 |
| aaattagcat | aacttcaaat | aagtgtccaa | aaaaggattc | tgcacagctt | taaaattaggc | 1560 |
| ctctgggctt | tacggaggaa | gtagaggtta | ttcttcagta | catctgtgaa | tgtgaatgcc | 1620 |
| aaagcgaagg | catccctgaa | agtcccaagt | gtcatgaagg | aaatgggaca | tttgagtgtg | 1680 |
| gcgcgtgcag | gtgcaatgaa | gggcgtgttg | gtagacattg | tgaatgcagc | acagatgaag | 1740 |

```
ttaacagtga agacatggat gcttactgca ggaaagaaaa cagttcagaa atctgcagta      1800
acaatggaga gtgcgtctgc ggacagtgtg tttgtaggaa gagggataat acaaatgaaa      1860
tttattctgg caaattctgc gagtgtgata atttcaactg tgatagatcc aatggcttaa      1920
tttgtggagg aaatggtgtt tgcaagtgtc gtgtgtgtga gtgcaacccc aactacactg      1980
gcagtgcatg tgactgttct ttggatacta gtacttgtga agccagcaac ggacagatct      2040
gcaatggccg gggcatctgc gagtgtggtg tctgtaagtg tacagatccg aagtttcaag      2100
ggcaaacgtg tgagatgtgt cagacctgcc ttggtgtctg tgctgagcat aaagaatgtg      2160
ttcagtgcag agccttcaat aaaggagaaa agaaagacac atgcacacag gaatgttcct      2220
attttaacat taccaaggta gaaagtcggg acaaattacc ccagccggtc caacctgatc      2280
ctgtgtccca ttgtaaggag aaggatgttg acgactgttg gttctatttt acgtattcag      2340
tgaatgggaa caacgaggtc atggttcatg ttgtggagaa tccagagtgt cccactggtc      2400
cagacatcat tccaattgta gctggtgtgg ttgctggaat tgttcttatt ggccttgcat      2460
tactgctgat atgaagcttt ttaatgataa ttcatgacga agggagttt gctaaatttg       2520 aaaaggagaa aatgaatgcc aaatgggaca cgggtgaaaa tcctatttat aagagtgccg      2580
taacaactgt ggtcaatccg aagtatgagg gaaaatgagt actgcccgtg caaatcccac      2640
aacactgaat gcaaagtagc aatttccata gtcacagtta ggtagcttta gggcaatatt      2700
gccatggttt tactcatgtg caggttttga aaatgtacaa tatgtataat ttttaaaatg      2760
ttttattatt ttgaaaataa tgttgtaatt catgccaggg actgacaaaa gacttgagac      2820
aggatggtta ctcttgtcag ctaaggtcac attgtgcctt tttgaccttt tcttcctgga      2880
ctattgaaat caagcttatt ggattaagtg atatttctat agcgattgaa agggcaatag      2940
ttaaagtaat gagcatgatg agagtttctg ttaatcatgt attaaaactg attttagct       3000 ttacaaatat gtcagtttgc agttatgcag aatccaaagt aaatgtcctg ctagctagtt      3060
aaggattgtt ttaaatctgt tattttgcta tttgcctgtt agacatgact gatgacatat      3120
ctgaaagaca agtatgttga gagttgctgg tgtaaaatac gtttgaaata gttgatctac      3180
aaaggccatg ggaaaaattc agagagttag gaaggaaaaa ccaatagctt taaaacctgt      3240
gtgccatttt aagagttact taatgtttgg taacttttat gccttcactt tacaaattca      3300
agccttagat aaaagaaccg agcaattttc tgctaaaaag tccttgattt agcactattt      3360
acatacaggc catactttac aaagtatttg ctgaatgggg accttttgag ttgaatttat      3420
tttattattt ttattttgtt taatgtctgg tgctttctgt cacctcttct aatcttttaa      3480
tgtatttgtt tgcaattttg gggtaagact ttttttatga gtacttttc tttgaagttt       3540 tagcggtcaa tttgcctttt taatgaacat gtgaagttat actgtggcta tgcaacagct      3600
ctcacctacg cgagtcttac tttgagttag tgccataaca gaccactgta tgtttacttc      3660
tcaccatttg agttgcccat cttgtttcac actagtcaca ttcttgtttt aagtgccttt      3720
agttttaaca gttcactttt tacagtgcta tttactgaag ttatttatta aatatgccta      3780
aaatacttaa atcggatgtc ttgactctga tgtatttat caggttgtgt gcatgaaatt       3840
tttatagatt aaagaagttg aggaaaagca aaaaaaaa                               3879
```

<210> SEQ ID NO 9
<211> LENGTH: 788
<212> TYPE: PRT
<213> ORGANISM: Homo Sapiens

<400> SEQUENCE: 9

```
Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
            85                  90                  95

Asp Lys Gly Ser Gly Asp Ser Ser Gln Val Thr Gln Val Ser Pro Gln
        100                 105                 110

Arg Ile Ala Leu Arg Leu Arg Pro Asp Asp Ser Lys Asn Phe Ser Ile
    115                 120                 125

Gln Val Arg Gln Val Glu Asp Tyr Pro Val Asp Ile Tyr Tyr Leu Met
130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
            165                 170                 175

Ile Gly Phe Gly Ala Phe Val Asp Lys Pro Val Ser Pro Tyr Met Tyr
        180                 185                 190

Ile Ser Pro Pro Glu Ala Leu Glu Asn Pro Cys Tyr Asp Met Lys Thr
    195                 200                 205

Thr Cys Leu Pro Met Phe Gly Tyr Lys His Val Leu Thr Leu Thr Asp
210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
            245                 250                 255

Val Cys Asp Glu Lys Ile Gly Trp Arg Asn Asp Ala Ser His Leu Leu
        260                 265                 270

Val Phe Thr Thr Asp Ala Lys Thr His Ile Ala Leu Asp Gly Arg Leu
    275                 280                 285

Ala Gly Ile Val Gln Pro Asn Asp Gly Gln Cys His Val Gly Ser Asp
290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
            325                 330                 335

Thr Glu Asn Val Val Asn Leu Tyr Gln Asn Tyr Ser Glu Leu Ile Pro
        340                 345                 350

Gly Thr Thr Val Gly Val Leu Ser Met Asp Ser Ser Asn Val Leu Gln
    355                 360                 365

Leu Ile Val Asp Ala Tyr Gly Lys Ile Arg Ser Lys Val Glu Leu Glu
370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
            405                 410                 415
```

```
Ile Gly Asp Thr Val Ser Phe Ser Ile Glu Ala Lys Val Arg Gly Cys
                420                 425                 430

Pro Gln Glu Lys Glu Lys Ser Phe Thr Ile Lys Pro Val Gly Phe Lys
            435                 440                 445

Asp Ser Leu Ile Val Gln Val Thr Phe Asp Cys Asp Cys Ala Cys Gln
        450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
        515                 520                 525

Cys Gly Gln Cys Val Cys His Ser Ser Asp Phe Gly Lys Ile Thr Gly
530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
        595                 600                 605

Cys Gly Ser Cys Val Cys Ile Gln Pro Gly Ser Tyr Gly Asp Thr Cys
610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Gly Ala Leu His Asp Glu Asn Thr
                645                 650                 655

Cys Asn Arg Tyr Cys Arg Asp Glu Ile Glu Ser Val Lys Glu Leu Lys
            660                 665                 670

Asp Thr Gly Lys Asp Ala Val Asn Cys Thr Tyr Lys Asn Glu Asp Asp
        675                 680                 685

Cys Val Val Arg Phe Gln Tyr Tyr Glu Asp Ser Ser Gly Lys Ser Ile
690                 695                 700

Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Glu Arg Ala Arg Ala Lys Trp Asp Thr Ala
        755                 760                 765

Asn Asn Pro Leu Tyr Lys Glu Ala Thr Ser Thr Phe Thr Asn Ile Thr
770                 775                 780

Tyr Arg Gly Thr
785

<210> SEQ ID NO 10
<211> LENGTH: 4894
<212> TYPE: DNA
<213> ORGANISM: Homo Sapiens

<400> SEQUENCE: 10
```

```
cgccgcggga ggcggacgag atgcgagcgc ggccgcggcc ccggccgctc tgggcgactg    60
tgctggcgct gggggcgctg gcgggcgttg gcgtaggagg gcccaacatc tgtaccacgc   120
gaggtgtgag ctcctgccag cagtgcctgg ctgtgagccc catgtgtgcc tggtgctctg   180
atgaggccct gcctctgggc tcacctcgct gtgacctgaa ggagaatctg ctgaaggata   240
actgtgcccc agaatccatc gagttccag tgagtgaggc ccgagtacta gaggacaggc   300
ccctcagcga caagggctct ggagacagct cccaggtcac tcaagtcagt ccccagagga   360
ttgcactccg gctccggcca gatgattcga agaatttctc catccaagtg cggcaggtgg   420
aggattaccc tgtggacatc tactacttga tggacctgtc ttactccatg aaggatgatc   480
tgtggagcat ccagaacctg ggtaccaagc tggccaccca gatgcgaaag ctcaccagta   540
acctgcggat tggcttcggg gcatttgtgg acaagcctgt gtcaccatac atgtatatct   600
ccccaccaga ggccctcgaa acccctgct atgatatgaa gaccacctgc ttgcccatgt   660
ttggctacaa acacgtgctg acgctaactg accaggtgac ccgcttcaat gaggaagtga   720
agaagcagag tgtgtcacgg aaccgagatg ccccagaggg tggctttgat gccatcatgc   780
aggctacagt ctgtgatgaa agattggct ggaggaatga tgcatcccac ttgctggtgt   840
ttaccactga tgccaagact catatagcat ggacggaag gctggcaggc attgtccagc   900
ctaatgacgg gcagtgtcat gttggtagtg acaatcatta ctctgcctcc actaccatgg   960
attatccctc tttggggctg atgactgaga agctatccca gaaaaacatc aatttgatct  1020
ttgcagtgac tgaaaatgta gtcaatctct atcagaacta tagtgagctc atcccaggga  1080
ccacagttgg ggttctgtcc atggattcca gcaatgtcct ccagctcatt gttgatgctt  1140
atgggaaaat ccgttctaaa gtagagctgg aagtgcgtga cctccctgaa gagttgtctc  1200
tatccttcaa tgccacctgc ctcaacaatg aggtcatccc tggcctcaag tcttgtatgg  1260
gactcaagat tggagacacg gtgagcttca gcattgaggc caaggtgcga ggctgtcccc  1320
aggagaagga gaagtccttt accataaagc ccgtgggctt caaggacagc ctgatcgtcc  1380
aggtcacctt tgattgtgac tgtgcctgcc aggcccaagc tgaacctaat agccatcgct  1440
gcaacaatgg caatgggacc tttgagtgtg gggtatgccg ttgtgggcct ggctggctgg  1500
gatcccagtg tgagtgctca gaggaggact atcgcccttc ccagcaggac gaatgcagcc  1560
cccgggaggg tcagcccgtc tgcagccagc ggggcgagtg cctctgtggt caatgtgtct  1620
gccacagcag tgactttggc aagatcacgg gcaagtactg cgagtgtgac gacttctcct  1680
gtgtccgcta caaggggag atgtgctcag gccatggcca gtgcagctgt ggggactgcc  1740
tgtgtgactc cgactggacc ggctactact gcaactgtac cacgcgtact gacacctgca  1800
tgtccagcaa tgggctgctg tgcagcggcc gcggcaagtg tgaatgtggc agctgtgtct  1860
gtatccagcc gggctcctat ggggacacct gtgagaagtg ccccacctgc ccagatgcct  1920
gcacctttaa gaaagaatgt gtggagtgta agaagtttga ccggggagcc ctacatgacg  1980
aaaatacctg caaccgttac tgccgtgacg agattgagtc agtgaaagag cttaaggaca  2040
ctggcaagga tgcagtgaat tgtacctata aagaatgagga tgactgtgtc gtcagattcc  2100
agtactatga agattctagt ggaaagtcca tcctgtatgt ggtagaagag ccagagtgtc  2160
ccaagggccc tgacatcctg gtggtcctgc tctcagtgat ggggccatt ctgctcattg  2220 gccttgccgc cctgctcatc tggaaactcc tcatcaccat ccacgaccga aaagaattcg  2280
ctaaatttga ggaagaacgc gccagagcaa atgggacac agccaacaac ccactgtata  2340
```

```
aagaggccac gtctaccttc accaatatca cgtaccgggg cacttaatga taagcagtca    2400
tcctcagatc attatcagcc tgtgccacga ttgcaggagt ccctgccatc atgtttacag    2460
aggacagtat ttgtggggag ggatttgggg ctcagagtgg ggtaggttgg gagaatgtca    2520
gtatgtggaa gtgtgggtct gtgtgtgtgt atgtggggt ctgtgtgttt atgtgtgtgt    2580
gttgtgtgtg ggagtgtgta atttaaaatt gtgatgtgtc ctgataagct gagctcctta    2640
gcctttgtcc cagaatgcct cctgcaggga ttcttcctgc ttagcttgag ggtgactatg    2700
gagctgagca ggtgttcttc attacctcag tgagaagcca gctttcctca tcaggccatt    2760
gtccctgaag agaagggcag ggctgaggcc tctcattcca gaggaaggga caccaagcct    2820
tggctctacc ctgagttcat aaatttatgg ttctcaggcc tgactctcag cagctatggt    2880
aggaactgct gggcttggca gcccgggtca tctgtacctc tgcctccttt cccctccctc    2940
aggccgaagg aggagtcagg gagagctgaa ctattagagc tgcctgtgcc ttttgccatc    3000
ccctcaaccc agctatggtt ctctcgcaag ggaagtcctt gcaagctaat tctttgacct    3060
gttgggagtg aggatgtctg ggccactcag gggtcattca tggcctgggg gatgtaccag    3120
catctcccag ttcataatca caaccttca gatttgcctt attggcagct ctactctgga    3180
ggtttgttta aagaagtgt gtcacccta ggccagcacc atctctttac ctcctaattc    3240
cacaccctca ctgctgtaga catttgctat gagctgggga tgtctctcat gaccaaatgc    3300
ttttcctcaa agggagagag tgctattgta gagccagagg tctggcccta tgcttccggc    3360
ctcctgtccc tcatccatag cacctccaca tacctggccc tgtgccttgg tgtgctgtat    3420
ccatccatgg ggctgattgt atttaccttc tacctcttgg ctgccttgtg aaggaattat    3480
tcccatgagt tggctgggaa taagtgccag gatggaatga tgggtcagtt gtatcagcac    3540
gtgtggcctg ttcttctatg ggttggacaa cctcatttta actcagtctt taatctgaga    3600
ggccacagtg caatttat ttattttct catgatgagg ttttcttaac ttaaaagaac    3660
atgtatataa acatgcttgc attatatttg taaatttatg tgatggcaaa gaaggagagc    3720
ataggaaacc acacagactt gggcagggta cagacactcc cacttggcat cattcacagc    3780
aagtcactgg ccagtggctg gatctgtgag gggctctctc atgatagaag gctatgggga    3840
tagatgtgtg gacacattgg acctttcctg aggaagaggg actgttcttt tgtcccagaa    3900
aagcagtggc tccattggtg ttgacataca tccaacatta aaagccaccc ccaaatgccc    3960
aagaaaaaaa gaaagactta tcaacatttg ttccatgagc agaaaactgg agctctggcc    4020
tcagtgttac agctaaataa tctttaatta aggcaagtca ctttcttctt cttaaagctg    4080
ttttctagtt tgagaaatga tgggatttta gcagccagtc ttgaaggtct ctttcagtat    4140
caacattcta agatgctggg acttactgtg tcatcaaatg tgcggttaag attctctggg    4200
atattgatac tgtttgtgtt tttagttggg agatctgaga gacctggctt tggcaagagc    4260
agatgtcatt ccatatcacc tttctcaatg aaagtctcat tctatcctct ctccaaaccc    4320
gttttccaac atttgttaat agttacgtct ctcctgatgt agcacttaag cttcatttag    4380
ttattatttc tttcttcact ttgcacacat ttgcatccac atattaggga agaggaatcc    4440
ataagtagct gaaatatcta ttctgtatta ttgtgttaac attgagaata agccttggaa    4500
ttagatatgg ggcaatgact gagccctgtc tcacccatgg attactcctt actgtaggga    4560
atggcagtat ggtagaggga taaatagggg gcggggaggg atagtcatgg atccaagaag    4620
tccttagaaa tagtggcagg gaacaggtgt ggaagctcat gcctgtaatt ataaccttca    4680
gctactaaga caggtgtggt ggctcacgcc tgtgattata atcttcagtt actaagacag    4740
```

```
agtccatgag agtgttaatg ggacattttc tttagataag atgttttata tgaagaaact    4800
gtatcaaagg gggaagaaaa tgtatttaac aggtgaatca aatcaggaat cttgtctgag    4860
ctactggaat gaagttcaca ggtcttgaag acca                                4894
```

<210> SEQ ID NO 11
<211> LENGTH: 799
<212> TYPE: PRT
<213> ORGANISM: Homo Sapiens

<400> SEQUENCE: 11

```
Met Pro Arg Ala Pro Ala Pro Leu Tyr Ala Cys Leu Leu Gly Leu Cys
1               5                   10                  15

Ala Leu Leu Pro Arg Leu Ala Gly Leu Asn Ile Cys Thr Ser Gly Ser
                20                  25                  30

Ala Thr Ser Cys Glu Glu Cys Leu Leu Ile His Pro Lys Cys Ala Trp
            35                  40                  45

Cys Ser Lys Glu Asp Phe Gly Ser Pro Arg Ser Ile Thr Ser Arg Cys
        50                  55                  60

Asp Leu Arg Ala Asn Leu Val Lys Asn Gly Cys Gly Gly Glu Ile Glu
65                  70                  75                  80

Ser Pro Ala Ser Ser Phe His Val Leu Arg Ser Leu Pro Leu Ser Ser
                85                  90                  95

Lys Gly Ser Gly Ser Ala Gly Trp Asp Val Ile Gln Met Thr Pro Gln
                100                 105                 110

Glu Ile Ala Val Asn Leu Arg Pro Gly Asp Lys Thr Thr Phe Gln Leu
            115                 120                 125

Gln Val Arg Gln Val Glu Asp Tyr Pro Val Asp Leu Tyr Tyr Leu Met
        130                 135                 140

Asp Leu Ser Leu Ser Met Lys Asp Asp Leu Asp Asn Ile Arg Ser Leu
145                 150                 155                 160

Gly Thr Lys Leu Ala Glu Glu Met Arg Lys Leu Thr Ser Asn Phe Arg
                165                 170                 175

Leu Gly Phe Gly Ser Phe Val Asp Lys Asp Ile Ser Pro Phe Ser Tyr
            180                 185                 190

Thr Ala Pro Arg Tyr Gln Thr Asn Pro Cys Ile Gly Tyr Lys Leu Phe
        195                 200                 205

Pro Asn Cys Val Pro Ser Phe Gly Phe Arg His Leu Leu Pro Leu Thr
    210                 215                 220

Asp Arg Val Asp Ser Phe Asn Glu Glu Val Arg Lys Gln Arg Val Ser
225                 230                 235                 240

Arg Asn Arg Asp Ala Pro Glu Gly Gly Phe Asp Ala Val Leu Gln Ala
                245                 250                 255

Ala Val Cys Lys Glu Lys Ile Gly Trp Arg Lys Asp Ala Leu His Leu
            260                 265                 270

Leu Val Phe Thr Thr Asp Asp Val Pro His Ile Ala Leu Asp Gly Lys
        275                 280                 285

Leu Gly Gly Leu Val Gln Pro His Asp Gly Gln Cys His Leu Asn Glu
    290                 295                 300

Ala Asn Glu Tyr Thr Ala Ser Asn Gln Met Asp Tyr Pro Ser Leu Ala
305                 310                 315                 320

Leu Leu Gly Glu Lys Leu Ala Glu Asn Ile Asn Leu Ile Phe Ala
                325                 330                 335

Val Thr Lys Asn His Tyr Met Leu Tyr Lys Asn Phe Thr Ala Leu Ile
```

-continued

```
                340                 345                 350
Pro Gly Thr Thr Val Glu Ile Leu Asp Gly Asp Ser Lys Asn Ile Ile
            355                 360                 365
Gln Leu Ile Ile Asn Ala Tyr Asn Ser Ile Arg Ser Lys Val Glu Leu
            370                 375                 380
Ser Val Trp Asp Gln Pro Glu Asp Leu Asn Leu Phe Phe Thr Ala Thr
385                 390                 395                 400
Cys Gln Asp Gly Val Ser Tyr Pro Gly Gln Arg Lys Cys Glu Gly Leu
                405                 410                 415
Lys Ile Gly Asp Thr Ala Ser Phe Glu Val Ser Leu Glu Ala Arg Ser
            420                 425                 430
Cys Pro Ser Arg His Thr Glu His Val Phe Ala Leu Arg Pro Val Gly
            435                 440                 445
Phe Arg Asp Ser Leu Glu Val Gly Val Thr Tyr Asn Cys Thr Cys Gly
            450                 455                 460
Cys Ser Val Gly Leu Glu Pro Asn Ser Ala Arg Cys Asn Gly Ser Gly
465                 470                 475                 480
Thr Tyr Val Cys Gly Leu Cys Glu Cys Ser Pro Gly Tyr Leu Gly Thr
                485                 490                 495
Arg Cys Glu Cys Gln Asp Gly Glu Asn Gln Ser Val Tyr Gln Asn Leu
            500                 505                 510
Cys Arg Glu Ala Glu Gly Lys Pro Leu Cys Ser Gly Arg Gly Asp Cys
            515                 520                 525
Ser Cys Asn Gln Cys Ser Cys Phe Glu Ser Glu Phe Gly Lys Ile Tyr
            530                 535                 540
Gly Pro Phe Cys Glu Cys Asp Asn Phe Ser Cys Ala Arg Asn Lys Gly
545                 550                 555                 560
Val Leu Cys Ser Gly His Gly Glu Cys His Cys Gly Glu Cys Lys Cys
                565                 570                 575
His Ala Gly Tyr Ile Gly Asp Asn Cys Asn Cys Ser Thr Asp Ile Ser
            580                 585                 590
Thr Cys Arg Gly Arg Asp Gly Gln Ile Cys Ser Glu Arg Gly His Cys
            595                 600                 605
Leu Cys Gly Gln Cys Gln Cys Thr Glu Pro Gly Ala Phe Gly Glu Met
            610                 615                 620
Cys Glu Lys Cys Pro Thr Cys Pro Asp Ala Cys Ser Thr Lys Arg Asp
625                 630                 635                 640
Cys Val Glu Cys Leu Leu Leu His Ser Gly Lys Pro Asp Asn Gln Thr
                645                 650                 655
Cys His Ser Leu Cys Arg Asp Glu Val Ile Thr Trp Val Asp Thr Ile
            660                 665                 670
Val Lys Asp Asp Gln Glu Ala Val Leu Cys Phe Tyr Lys Thr Ala Lys
            675                 680                 685
Asp Cys Val Met Met Phe Thr Tyr Val Glu Leu Pro Ser Gly Lys Ser
            690                 695                 700
Asn Leu Thr Val Leu Arg Glu Pro Glu Cys Gly Asn Thr Pro Asn Ala
705                 710                 715                 720
Met Thr Ile Leu Leu Ala Val Val Gly Ser Ile Leu Leu Val Gly Leu
                725                 730                 735
Ala Leu Leu Ala Ile Trp Lys Leu Leu Val Thr Ile His Asp Arg Arg
            740                 745                 750
Glu Phe Ala Lys Phe Gln Ser Glu Arg Ser Arg Ala Arg Tyr Glu Met
            755                 760                 765
```

```
Ala Ser Asn Pro Leu Tyr Arg Lys Pro Ile Ser Thr His Thr Val Asp
    770                 775                 780

Phe Thr Phe Asn Lys Phe Asn Lys Ser Tyr Asn Gly Thr Val Asp
785                 790                 795

<210> SEQ ID NO 12
<211> LENGTH: 3392
<212> TYPE: DNA
<213> ORGANISM: Homo Sapiens

<400> SEQUENCE: 12
gcggagccag cccctcccct acccggagca gcccgctggg gccgtcccga gcggcgacac      60
actaggagtc ccggccggcc agccagggca gccgcggtcc cgggactcgg ccgtgagtgc     120
tgcgggacgg atggtggcgg cggggcgcgg gccagcgcgg gcgccgtgag ccggagctgc     180
gcgcggggca tgcggctgcg gcccccggcc ctcggccccc gcgctccggc cccagccccg     240
gccgccggcc cccgcggagt gcagcgaccg cgccgccgct gagggaggcg ccccaccatg     300
ccgcgggccc cggcgccgct gtacgcctgc ctcctggggc tctgcgcgct cctgccccgg     360
ctcgcaggtc tcaacatatg cactagtgga agtgccacct catgtgaaga atgtctgcta     420
atccacccaa aatgtgcctg tgctccaaa gaggacttcg gaagcccacg gtccatcacc     480
tctcggtgtg atctgagggc aaaccttgtc aaaaatggct gtggaggtga datagagagc     540
ccagccagca gcttccatgt cctgaggagc ctgcccctca gcagcaaggg ttcgggctct     600
gcaggctggg acgtcattca gatgacacca caggagattg ccgtgaacct ccggcccggt     660
gacaagacca ccttccagct acaggttcgc caggtggagg actatcctgt ggacctgtac     720
tacctgatgg acctctccct gtccatgaag gatgacttgg acaatatccg gagcctgggc     780
accaaactcg cggaggagat gaggaagctc accagcaact tccggttggg atttgggtct     840
tttgttgata aggacatctc tccttctcc tacacggcac cgaggtacca gaccaatccg     900
tgcattggtt acaagttgtt tccaaattgc gtccctcct ttgggttccg ccatctgctg     960
cctctcacag acagagtgga cagcttcaat gaggaagttc ggaaacagag ggtgtcccgg    1020
aaccgagatg cccctgaggg gggctttgat gcagtactcc aggcagccgt ctgcaaggag    1080
aagattggct ggcgaaagga tgcactgcat ttgctggtgt tcacaacaga tgatgtgccc    1140
cacatcgcat tggatggaaa attgggaggc tggtgcagc acacgatgg ccagtgccac    1200 ctgaacgagg ccaacgagta cactgcatcc aaccagatgg actatccatc ccttgccttg    1260
cttggagaga aattggcaga gaacaacatc aacctcatct ttgcagtgac aaaaaaccat    1320
tatatgctgt acaagaattt tacagccctg atacctggaa caacggtgga gatttagat   1380 ggagactcca aaatattat tcaactgatt attaatgcat acaatagtat ccggtctaaa    1440
gtggagttgt cagtctggga tcagcctgag gatcttaatc tcttctttac tgctacctgc    1500
caagatgggg tatcctatcc tggtcagagg aagtgtgagg gtctgaagat ggggacacg    1560 gcatctttg aagtatcatt ggaggcccga agctgtccca gcagacacac ggagcatgtg    1620
tttgccctgc ggccggtggg attccgggac agcctggagg tggggtcac ctacaactgc    1680 acgtgcggct gcagcgtggg gctggaaccc aacagtgcca ggtgcaacgg gagcgggacc    1740
tatgtctgcg gcctgtgtga gtgcagcccc ggctacctgg caccaggtg cgagtgccag    1800 gatgggagga accagagcgt gtaccagaac ctgtgccgg aggcagaggg caagccactg    1860
tgcagcgggc gtggggactg cagctgcaac cagtgctcct gcttcgagag cgagttcggc    1920
```

```
aagatctatg ggcctttctg tgagtgcgac aacttctcct gtgccaggaa caagggagtc   1980
ctctgctcag gccatggcga gtgtcactgc ggggaatgca agtgccatgc aggttacatc   2040
ggggacaact gtaactgctc gacagacatc agcacatgcc ggggcagaga tggccagatc   2100
tgcagcgagc gtgggcactg tctctgtggg cagtgccaat gcacggagcc gggggccttt   2160
ggggagatgt gtgagaagtg ccccacctgc ccggatgcat gcagcaccaa gagagattgc   2220
gtcgagtgcc tgctgctcca ctctgggaaa cctgacaacc agacctgcca cagcctatgc   2280
agggatgagg tgatcacatg ggtggacacc atcgtgaaag atgaccagga ggctgtgcta   2340
tgtttctaca aaccgccaa ggactgcgtc atgatgttca cctatgtgga gctccccagt   2400
gggaagtcca acctgaccgt cctcagggag ccagagtgtg aaacacccc aacgccatg    2460 accatcctcc tggctgtggt cggtagcatc ctccttgttg ggcttgcact cctggctatc   2520
tggaagctgc ttgtcaccat ccacgaccgg agggagtttg caaagtttca gagcgagcga   2580
tccagggccc gctatgaaat ggcttcaaat ccattataca gaaagccat ctccacgcac    2640 actgtggact tcaccttcaa caagttcaac aaatcctaca atggcactgt ggactgatgt   2700
ttccttctcc gaggggctgg agcggggatc tgatgaaaag gtcagactga acgccttgc    2760 acggctgctc ggcttgatca cagctcccta ggtaggcacc acagaagaa ccttctagtg    2820 agcctgggcc aggagcccac agtgcctgta caggaaggtg cctggccatg tcacctggct   2880
gctaggccag agccatgcca ggctgcgtcc ctccgagctt gggataaagc aaggggacct   2940
tggcactctc agctttccct gccacatcca gcttgttgtc ccaatgaaat actgagatgc   3000
tgggctgtct ctcccttcca ggaatgctgg gcccccagcc tggccagaca agacgactgt   3060
caggaagggt cggagtctgt aaaaccagca tacagtttgg cttttttcac attgatcatt   3120
tttatatgaa ataaaaagat cctgcattta tggtgtagtt ctgagtcctg agacttttcc   3180
gcgtgatggc tatgccttgc acacaggtgt tggtgatggg gctgttgaga tgcctgttga   3240
aggtacatcg tttgcaaatg tcagtttcct ctcctgtccg tgtttgttta gtactttat    3300 aatgaaaaga aacaagattg tttgggattg gaagtaaaga ttaaaaccaa aagaatttgt   3360
gtttgtctga taaaaaaaaaa aaaaaaaaaa aa                                 3392
```

<210> SEQ ID NO 13
<211> LENGTH: 12
<212> TYPE: PRT
<213> ORGANISM: Artificial sequence
<220> FEATURE:
<223> OTHER INFORMATION: Synthetic Construct

<400> SEQUENCE: 13

Gly Arg Gly Asp Ser Val Val Tyr Gly Leu Arg Ser
1               5                   10

<210> SEQ ID NO 14
<211> LENGTH: 25
<212> TYPE: RNA
<213> ORGANISM: Artificial sequence
<220> FEATURE:
<223> OTHER INFORMATION: Synthetic Construct

<400> SEQUENCE: 14
ccacagccac aagcagucca gauua                                          25

<210> SEQ ID NO 15
<211> LENGTH: 25
<212> TYPE: RNA

```
<213> ORGANISM: Artificial sequence
<220> FEATURE:
<223> OTHER INFORMATION: Synthetic Construct

<400> SEQUENCE: 15
ccuaagucag caguaggaac auuau                                              25

<210> SEQ ID NO 16
<211> LENGTH: 25
<212> TYPE: RNA
<213> ORGANISM: Artificial sequence
<220> FEATURE:
<223> OTHER INFORMATION: Synthetic Construct

<400> SEQUENCE: 16
ccuccagcuc auuguugaug cuuau                                              25

<210> SEQ ID NO 17
<211> LENGTH: 25
<212> TYPE: RNA
<213> ORGANISM: Artificial sequence
<220> FEATURE:
<223> OTHER INFORMATION: Synthetic Construct

<400> SEQUENCE: 17
agaaugucug cuaauccacc caaaa                                              25

<210> SEQ ID NO 18
<211> LENGTH: 25
<212> TYPE: RNA
<213> ORGANISM: Artificial sequence
<220> FEATURE:
<223> OTHER INFORMATION: Synthetic Construct

<400> SEQUENCE: 18
cugagggcaa accuugucaa aaaug                                              25

<210> SEQ ID NO 19
<211> LENGTH: 25
<212> TYPE: RNA
<213> ORGANISM: Artificial sequence
<220> FEATURE:
<223> OTHER INFORMATION: Synthetic Construct

<400> SEQUENCE: 19
gaaauggcuu caaauccauu auaca                                              25

<210> SEQ ID NO 20
<211> LENGTH: 25
<212> TYPE: RNA
<213> ORGANISM: Artificial sequence
<220> FEATURE:
<223> OTHER INFORMATION: Synthetic Construct

<400> SEQUENCE: 20
gaacaaggag ucgucagaaa cucca                                              25
```